US012618088B2

(12) United States Patent
Moseley et al.

(10) Patent No.: US 12,618,088 B2
(45) Date of Patent: May 5, 2026

(54) PRODUCTION OF LIPIDS AND TERPENOIDS IN *AUXENOCHLORELLA PROTOTHECOIDES*

(71) Applicants: Phycoil Biotechnology International, Inc., Fremont, CA (US); Phycoilbiotech Korea, Inc., Seoul (KR)

(72) Inventors: Jeffrey Moseley, Fremont, CA (US); Byung-Hee Lee, Seoul (KR); Chung-Soon Im, Seoul (KR); Jane Kim, Fremont, CA (US); Dayoung Kim, Seoul (KR); Riyaz Bhat, Fremont, CA (US)

(73) Assignee: Phycoil Biotechnology International, Inc., Fremont, CA (US)

( * ) Notice: Subject to any disclaimer, the term of this patent is extended or adjusted under 35 U.S.C. 154(b) by 50 days.

(21) Appl. No.: 18/680,175

(22) Filed: May 31, 2024

(65) Prior Publication Data

US 2024/0368646 A1 Nov. 7, 2024

Related U.S. Application Data

(62) Division of application No. 17/519,854, filed on Nov. 5, 2021, now Pat. No. 12,037,630.

(60) Provisional application No. 63/109,901, filed on Nov. 5, 2020.

(51) Int. Cl.
| | |
|---|---|
| *C12N 9/90* | (2006.01) |
| *C12N 9/02* | (2006.01) |
| *C12N 9/16* | (2006.01) |
| *C12N 15/52* | (2006.01) |
| *C12P 7/6472* | (2022.01) |

(52) U.S. Cl.
CPC .......... *C12P 7/6472* (2013.01); *C12N 9/0071* (2013.01); *C12N 9/0083* (2013.01); *C12N 9/16* (2013.01); *C12N 9/90* (2013.01); *C12N 15/52* (2013.01); *C12Y 114/19* (2013.01); *C12Y 114/19002* (2013.01); *C12Y 301/02014* (2013.01); *C12Y 505/01018* (2013.01)

(58) Field of Classification Search
CPC ........... C12P 7/6472; C12N 9/02; C12N 9/16
See application file for complete search history.

(56) References Cited

U.S. PATENT DOCUMENTS

| | | | |
|---|---|---|---|
| 9,932,554 B2 | 4/2018 | Im et al. | |
| 2010/0317735 A1 | 12/2010 | Hong et al. | |
| 2011/0086919 A1 | 4/2011 | Damude et al. | |
| 2011/0293785 A1 * | 12/2011 | Franklin | ................. A23D 9/00 |
| | | | 426/61 |

| | | | |
|---|---|---|---|
| 2014/0178950 A1 | 6/2014 | Solazyme | |
| 2016/0194672 A1 | 7/2016 | Solazyme | |
| 2016/0319218 A1 | 11/2016 | Leininger et al. | |

FOREIGN PATENT DOCUMENTS

| | | |
|---|---|---|
| KR | 1020180028288 | 3/2018 |
| KR | 101946362 B1 | 2/2019 |
| KR | 1020200074047 A | 6/2020 |
| WO | WO 2014/141098 | 9/2014 |

OTHER PUBLICATIONS

Smith et al., Squalene potential chemopreventive agent, 2009, Exp Opin Invest Drugs vol. 9, pp. 1841-1848.
Xiao et al, Industrial fermentation of auxenochlorella prototheoides for prodiction of biodiesel and its application . . . , 2015, Front bioeng biotechnol vol. 3, pp. 164.
Zaimes et al, Environmental sustainability of emerging algal biofuels a comparative life cycle evaluation of algal biodiesel . . . , 2013, Environ Prog Sustain Energy vol. 32.
Aloi et al, Effect of squalene on superoxide anion generation induced by a skin irritant, lauroylsarcosine, 1995, J. Pharmaceut vol. 113, pp. 159-164.
Amarowicz et al, Squalene: a natural antioxidant, 2009, Eur. J. Lipid Sci. vol. 111, pp. 411-412.
Bhujade et al, Algae to economically viable low-carbon-footprint Oil, 2017, Ann. Rev. Chem. Biomol. Eng. vol. 8, pp. 335-357.
Budiyanto et al, Protective effect of topically applied olive oil against photocarcinogenesis following exposure of mice, 2000, Carcinogenesis vol. 21, pp. 2085-2090.
Czaplicki et al, Characteristics of biologically-active substances of amaranth oil obtained by various techniques, 2012, Pol.J. Food Nutr. Sci vol. 62, pp. 235-239.
Del Giudice et al, Vaccines with the MF59 adjuvant do not stimulate antobody responses against squalene, 2006, Clin Vacc Immunol vol. 13, pp. 1010-1013.
Elwan et al, Red yeast (*Phaffia rhodozyme*) as a source of astaxanthin and its impact on productive performance and pysiological responses . . . , 2019, Worlds Poultry Sci J vol. 75.
Gunes et al, Medical use of squalene as a natural antioxidant, 2013, J. Marmara U Inst Health Sci Jan. 2013.
Huang et al, Biological and pharmacological activities of squalene and related compouinds potential uses in cosmetic dermatology, 2009, Molecules vol. 14, pp. 540-554.
Ivanova et al, Surface properties of squalene/melbum films and NMR confirmation of squalene in tears, 2015, Int J Mol Sci vol. 16, pp. 21813-21831.
Kim et al, Biological importance and applications of squalene and squalene, 2012, Adv Food Nutr Res vol. 65, pp. 223-233.
Kopicova et al, Occurrence of squalene and cholesterol in various species of Czech freshwater fish, 2007, Czech J Food Sci vol. 25, pp. 195-201.
Naguib et al, Antioxidant activities of astaxanthin and related carotenoids, 2000, J Agric Food Chem vol. 48, pp. 1150-1154.

(Continued)

*Primary Examiner* — Tekchand Saidha
(74) *Attorney, Agent, or Firm* — HelixIP LLP

(57) ABSTRACT

Methods to produce oils with modified profiles of fatty acid, carotenoids and/or terpenoids in microalgal mutants are provided. Microalgal mutants produce the oil containing fatty acids, carotenoids and/or terpenoids of a modified profile with a disruption or ablation of one or more alleles of an endogenous polynucleotide or comprising an exogenous gene are also provided.

16 Claims, 33 Drawing Sheets

Specification includes a Sequence Listing.

(56)              References Cited

OTHER PUBLICATIONS

Nicolaides et al, Skin lipids their biochemical uniqueness, 1974, Science vol. 186, pp. 29-26.

Pasquale et al, Vaccine adjuvants from 1920 to 2015 and beyond, 2015, Vaccines vol. 3, pp. 320-343.

Popa et al, Methods for obtaining and determination of squalene from natural sources, 2015, Hindawi Publ Corp, BioMed Res Intl, Article ID 367202.

Remize et al, Microalgae n-3 PUFAs production and use in food and feed industries, 2021, Marine Drugs vol. 19, pp. 1-289.

Roslaes-Garcia et al, Squalene extraction biological sources and extraction methods, 2017, Intl J Environ Agric Biotech vol. 2.

Schmidt et al, Biotechnological production of astaxanthin with Phaffia rhodozyma/Xanthophyllomyces dendrorhous, 2011, Appl Microbio Biotech vol. 89, pp. 555-571.

* cited by examiner

【FIG. 1】
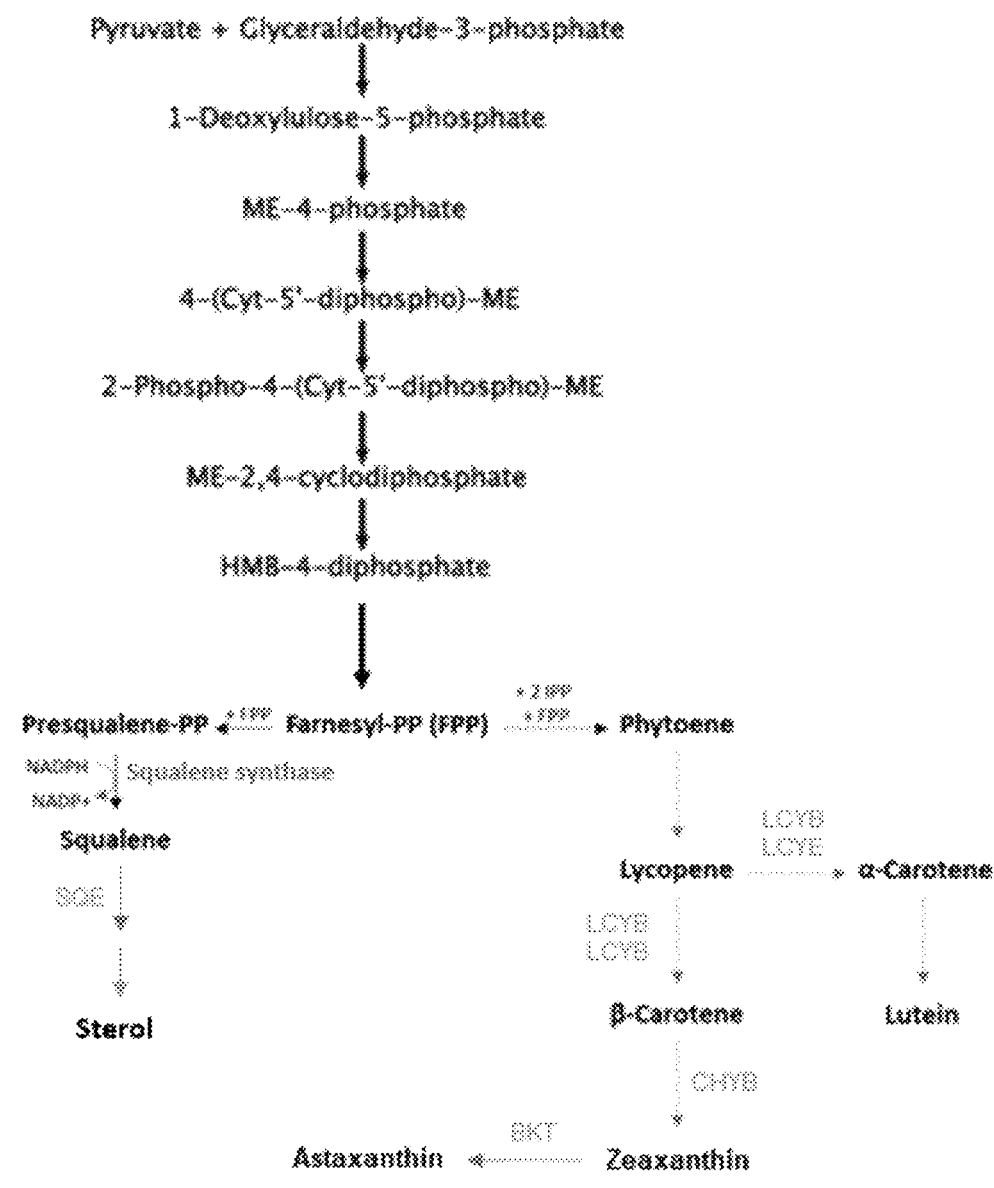

【FIG. 2A】 aagcttCAAGTGCGTGCGTTACAGTGTTACCAACAACAGTCTAACCTACCCCTTTCGGTCATTCTGC

CCTTTGGCAAGAGTTCAGAATGAAGTGTGCTTGCACATCGAGCTAGTGCTGTGAGCGAAGACAA

GGAAGTCCCCACTCACCCACGTGGCCAGATTCTATCTTTTTTCAGATTGCAAGGGCCACGCCCAG

CGAACCCCGCGATGGGGCCGAGCCATGCCCGACATCTCGACATCTTCATATGATAAGGCGCTTCA

AAGTGCAATTTTTGTGCATGGCATCAATTAGGAGAGTGCTTGAACACCAGCCCATCTTCCACCGG

GGAAGGACCGTCGAAATGCCTCTGCAGACGGCCACCGTCTGATCGCTGCCTGTCCCGAGGTGA

CGGCGATGTCGTCCTTATCCCAAACAATCGTTCGAAGACCTTTCTTTTGTTCGCTCAACCCACCG

AGGAGACCGTCTGGATTCCATGCTGCTGTGACGCCTAGCCCCCTGAGACCCTCCAAGTGGGCG

GTCCCCTCCCTAGCCCCCAGCCTCTCTGACGTGGCAGATGCCTCCGCGGAAGCAAATCAGGATC

GCAGGGAGGGCTCCTACGAGCAGCCCCTGGTCCAACGCCAGGTGCCTAGGGGGAAAGGAGGG

CAGAGGGGCTTGAGGCGAGCCTGGCCCAGGCAGGGCTTCCATGGTCAGTCGTGGCAGTGCCAT

GACAGCCGAAGCCCAACGCGACACCGTGGGTGCAGCATGCGTGGACGGAAACATTGGCAATGC

CTTGCCCCATTGGCCCCCCAGGCCCCGGAAACGGGACGATCAGCAGGACCCCTTGTCCAGCCTC

CTCCCCACggtacccttcttgcgctatgacacttccagcaaaaggtagggcgggctgcgagacggcttccggcgctgcatgcaaca ccgatgatgcttcgacccccgaagctccttcggggctgcatgggcgctccgatgccgctccagggcgagcgctgtttaaatagccaggccc ccgattgcaaagacattatagcgagctaccaaagccatattcaaacacctagatcactaccactctacacaggccactcgagcttgtgatcg tactccgctaggggggcgcctcttcctcttcgtttcagtcacaacccgcaaadATGctgctgcaggccttcctgttcctgctggccggcttcgcc gccaagatcagcgcctccatgacgaacgagacgtccgacgcccccctggtgcacttcacccccaacaagggctggatgaacgaccccaa cggcctgtggtacgacgagaaggacgccaagtggcacctgtacttccagtacaacccgaacgacaccgtctgggggacgcccttgttctgg ggccacgccacgtccgacgacctgaccaactgggaggaccagcccatcgccatcgcccgaagcgcaacgactccggcgccttctccgg ctccatggtggtggactacaacaacacctccggcttcttcaacgacaccatcgacccgcgccagcgctgcgtggccatctggacctacaaca ccccgggagtccgaggagcagtacatctcctacagcctggacggcgggctacaccttcaccgagtaccagaagaacccgtgctggccgcca actccacccagttccgcgacccgaaggtcttctggtacgagcccctccagaagtggatcatgaccgcgcgccaagtcccaggactacaagat cgagatctactcctccgacgacctgaagtcctggaagctggagtccgcgttcgccaacgagggcttcctcggctaccagtacgagtgccccg gcctgatcgaggtccccaccgagcaggaccccagcaagtcctactggtgtgatgttcatctccatcaacccggcgccccggccggcggctc cttcaaccagtacttcgtcggcagcttcaacggcaccccacttcgaggccttcgacaaccagtcccgcgtggtggacttcggcaaggactacta cgccctgcagaccttcttcaacaccgaccgacctacgggagcgccctgggcatcgcgtgggcctccaactgggagtactccgccttcgtgc

【FIG. 2B】 ccaccaaccctggcgctcctccatgtccctcgtgcgcaagttctccctcaacaccgagtaccaggccaaccctggagacggagctgatcaa cctgaaggccgagccgatcctgaacatcagcaacgccggccctggagccggttcgccaccaacaccacgttgacgaaggccaacagct acaacgtcgacctgtccaacagcaccggcacctggagttcgagctggtgtacgccgtcaacaccaccagacgatctccaagtccgtgttc gcggacctctccctctggttcaagggcctggaggaccccgaggagtacctccgcatgggcttcgaggtgtccgcgtcctccttcttcctggacc gcgggaacagcaaggtgaagttcgtgaaggagaaccccctacttcaccaaccgcatgagccgtgaacaaccagccctccaagagcgagaa cgacctgtcctactacaaggtgtacggcctgctggaccagaacatcctggagctgtacttcaacgacggcgacgtcgtgtccaccaacaccta cttcatgaccaccgggaacgccctgggctccgtgaacatgacgacgggggtgggacaaccctgttctacatcgacaagttccaggtgcgcgag gtcaagTGATTGATTGGAACTCACAAAGCGGCCCACGGCTTCGAACGTCCCGTGTCAATTGCGCGGGGTGTGCCAGA

GTTTCTGCGCCACCGATGCTCACCCTAGGGGGGGGATGCCCTTTGACATTCATGTGTGCCTGCATGCACGTTTGTATCA

GTCTCACCACACCTTGAAGATTTTTGGGAGGGGGGGGGAAGTCGGAATGGAAACgagctcCGCGATTGTCAGAT

GGTGGAGTGGGTGGATGGCCCTGCTCCGAGGAGCTTTCTAGGGCGCGAACTTGGCCCTTCTCC

CCTCTGATGCAGTGTGGGGGGACGCGGTGTGCTATTTCTCCGAGGGCCGCCCAACTAGGGTGG

GGCGGGCATACGCCCGCGTCGACAGGTGGGTGTGGCCTCGAGGTGTTGAGAGGAGTGTTATGT

CGACAGCCAAAGTGGAGACTGATTGAACCCTACTCCAGGTGCTATCTTGGGAGCACACTGCGCC

CACCGTGGCTGGACTGCCCGAATTCCAACCTTGGTGCCCAGAAACAGGGCAAAGCCGGTCATC

AGTGCAGCATGAGACTCAAGCTCCCTAGCTCATGACCGTTGGCATAGGCAGAAGCTGCGGCAGC

ACCTGGTGGAGGCCTGCCAGGCAAACGGTGTCACCTTCCAGCCGGGGGAGGTAGTGGATGTGG

GCGTGAAGAACGGCACAGCCTCGGTCACCTGCCAAGATGGCTCCGTCCTGACTGCGAGGTGGG

CGCTGTGCATGGCATTTGTTGGCACGAGTCTGCATCTCTGAAGCTGCTGGGTAGCGTCAGAGCA

GTGGAGTCAACAGCACACAGCTCTGGCGGTGCTCAGGGAACATACATCGCACTGTTTCCTGGAG

TTGCTGGCCCTCTGTGGGGCAACCAGGACCCCCCGACGCATGCATGCCCCCCTCGCACATCCCG

CACAGGCTGGTGACCCTGGCCTCCGGCGCGGCGGCGGGGCGCTTCCTCAAGTACGAGAG**aagc
tt**

【FIG. 3A】 aagctt CAAGTGCGTGCGTTACAGTGTTACCAACAACAGTCCAACCTAACCCTTTCGGTCATTCTGT
CCTTTGGCAAGGGCTCAGAATGAAGTGTGCCTGCACATCGAGCTAGTGCTGTGAGCGAAGACAA
GGAAGTCCCCACTCACCCACGTGGCCAGATTTTATCTTTTTTCAGATTGCAAGGGCCACGCCCAG
CGAACCCCGCGATGGGGCCGAGCCATGCCCGACATCTCGACATCTTCATATGACAAGGCGCTTC
AAAGTGCAATTTATGTGCATGGCATCGATTAGGAGAGTGGTTGAACACCAGCCCATCTTCCACCG
GGGAAGGACCGTCGAAATGCCTCTGCAGACGGCCACCGTCTGATCGCTGCCTGTCCCGAGGTG
ACGGCGATGTCGTCCTTATCCCAAACAATCGTTCGAAGACCTTTCTTTTGTTCGCTCAACCCACC
GAGGAGACCGTCTGGATTCCATGCCGCTGTGACGCCTAGCCCCCTGAGACCCTCCAAGTGGGC
GGTCCCCTCCCTAGCCCCCAGCCTCTCTGACGTGGCAGATGCCTCCGCGGAAGCAAATCAGGAT
CGCAGGGAGGGCTCCTACGAGCAGCCCCTGGTCCAACGCCAGGTGCCTAGGGGGAAAGGAGG
GCAGGGGGCCTTGAGGCGAGCCTGGCCCAGGCAGGGCTTCCATGGTCAGTCGTGGCAGTGCC
ATGACAGCCGAAGCCCACCGCGACACCGTGGGTGCAGCATGCGTGGACGGAAACATTGGCAAT
GCCTTGCCCCATTGGACCCCCAGGCCCCGGAAACGGGACGATCAGCAGGACCCCCTGTCCAGCC
TCCTCCCCAC ggtacc cccgctttttaattgagccccttttcgtcgctgaatcagcgaaagcaccgcgaaacaatgcctgtcccgtccat
gcatctcaacagcctcatgcaaggtttgcacaagcaagaccattctgatctgggaacttgtaggtgttgtatggggaggttgtgctcttgaatca
agtggtatcacgtttccggaacacccgaaacgtgcatgggcttaltgcgatgagagcatttcccaccgcgatigtctcacgcgcattcggag
aaggtttgcagaacactccaggacatgaaatgccttgtcacgtatgaaccatctcccacggccttgaaaagatcgctcgacttccattctaga
ggtgcaaaaccctacgactcaagaaggtgccaccgactcaggcattgggcacggcgggcagggagaagagaggagttgatcaaaactg
ctcgatcacgttcccccatggcgatccgagcagcacatgatgcatcgaggtggcgccgttgcaaaggagttgcgcatgggtcgaagcaggg
agaaggaaacggcgaggccgtgccgcgggggtgaattcagagtcaaatctgcgcctgccccggcgctcctgacggggattaacccccacg
actgtatccatcgacactcgtctcggggggaataaaaagcggcgacccagctccagaggcgcaatcctltctcacaatctgtttaactttcaacaaa
gtataagtcaattcaactlgacaca ATG gccgcgtccgtccactgcaccctgatgtccgtggtctgcaacaacaagaaccactccgcccgcc
ccaagctgcccaactcctccctgctgcccggcttcgacgtggtggtccaggccgcgcgccaccgcttcaagaaggagacgacgaccaccc
gcgccacgctgacgttcgacccccccacgaccaactccgagcgcgccaagcagcgcaagcacaccatcgacccctcctccccgacttcc
agcccatccccctccttcgaggagtgcttccccaagtccacgaaggagcacaaggaggtggtgcacgaggagtccggccacgtcctgaagg
tgcccttccgccgcgtgcacctgtccggcgcggcgagccggccttcgacaactacgacacgtccggcccccagaacgtcaacgcccacatcgg
cctggcgaagctgcgcaaggagtggatcgacgccgcgcgagaagctggcacgcccccgctacacgcagatgtactacgcgaagcagggc
atcatcacggaggagatgctgtactgcgcgacgcgcgcgagaagctggaccccgagttcgtccgctccgaggtcgcgcgcgggggccgcgccatc

【FIG. 3B】 atccctccaacaagaagcacctggagctggagcccatgatcgtgggccgcaagttcctggtgaaggtgaacgcgaacatcggcaactcc gccgtggcctcctccatcgaggaggaggtctacaaggtgcagtgggccaccatgtggggcgccgacaccatcatggacctgtccacgggc cgccacatccacgagacgcgcgagtggatcctgcgcaactccgcgcgtcccgtgggcaccgtcccatctaccaggcgctggagaaggtg gacggcatcgcggagaacctgaactgggaggtgttccgcgagacgctgatcgagcaggccgagcagggccgtggactacttcacgatcca cgccgggcgtgctgctgcgctacatccccctgaccgccaagcgcctgacgggcatcgtgtcccgcggcggctccatccacgcgaagtggtgc ctggcctaccacaaggagaacttcgcctacgagcactgggacgacatcctggacatctgcaaccagtacgacgtcgccctgtccatcggcg acggcctgcgcccggctccatctacgacgccaacgacacgcccagttcgccgagctgctgacccaggcgagctgacgcgccgcgcg tgggagaaggacgtgcaggtgatgaacgagggccccggccacgtgcccatgcacaagatccccgagaacatgcagaagcagctggagt ggtgcaacgaggcgcccttctacaccctgggcccccctgacgaccgacatcgcgcccggctacgaccacatcacctccgccatcggcgcgg ccaacatcggcgcccctgggcaccgccctgctgtgctacgtgacgcccaaggagcacctgggcctgcccaaccgcgacgacgtgaaggcg ggcgtcatcgcctacaagatcgccgcccacgcggccgacctggccaagcagcagcaccccacgcccaggcgtgggacgacgcgctgtcca aggcgcgcttcgagttccgctggatggaccagttcgcgctgtccctggacccccatgacggcgatgtccttccacgacgagacgctgcccgcg gacggcgcgaaggtcgcccacttctgctccatgtgcggcccccaagttctgctccatgaagatcacggaggacatccgcaagtacgccgagg agaacggctacggctccgccgaggaggccatccgccagggcatggacgccatgtccgaggagttcaacatcgccaagaagacgatctcc ggcgagcagcacggcgaggtcggccgggcgagatctacctgcccgagtcctacgtcaaggccgcgcagaag*TGAGTCCTGGCGACC*

*CTGCTCCCCTGACCCCTGTTCCCCTGCGCTGCTTCTCCCCGGTGACATCCGACCTGCTGCAAAATTCCCGTTCCTGC*

*ACAACACTTGCCTGACCGAGGGGTCGGGTCGCGAAGTAAAAGCCACAATCAACACCCCAGGCACATTAAGAGTGCACA*

*GCATGACGCAGCATAGGGTTTGTGTCGGAGGAAGGGGGTCGAGTCGCGTTGGCGAGGGGGTGGTCACGATGACCA*

*CATCTGCGGGATAATTGAATCCTCAGGGGAAAATACCAGTCTCTGCTTCCAGGTGCTCCG*gagctc<u>CGCGATTGTC</u>

<u>AGATGGTGGAGTGGGTGGATGGCCCTGCTCCAGAGGAGCGTTCTAGGGCGCAAACTTGGCACT</u>

<u>TTCCCCCCTCTGATGCAGTGTGGGGGGGACGCGGTGTGCTATTTCTCCGAGGGCCGCCCCAACCA</u>

<u>GGGTGGGGCGGGCATATGCCCGCGTCGACAGGTGGGTGTGTGGCCTCGAGGTGTTGAGAGGAGG</u>

<u>GTTATGTCGACAGCCAAAGTGGAGACTGAGTGAACCCTACTCCAGGTGCTGTCGTGGGAGCGCA</u>

<u>CTGCGCCCACCGTGGCTGGACTGCTCGTATTCCAACCTTGGTGCCCAGAAACAGGGCAAAGCC</u>

<u>GGTCATCAGTGCAGCATGAGACTCAAGCTCCCTAACTCATGACCGTTGGCATAGGCAGAAGCTG</u>

<u>CGGCAGCACCTGGTGGAGGCCTGCCAGGCAAACGGTGTCACCTTCCAGCCGGGGGGAGGTAGT</u>

<u>GGATGTGGGCGTGAAGAACGGCACAGCCTCGGTCACCTGCCGAGACGGCTCCGTCCTGACTGC</u>

<u>GAGGTGGGCGCTGTGCATGGCACTTGTTGGCACGAGTCTGCATCCCTGAAGCTGCTGGGTAGC</u>

<u>GTCAGAGCAGTGGCGTCAACAGCACACAGCTCTGGCGGTGCCCAGGGAACATACATCGCTCTG</u>

【FIG. 3C】
TTTCCTGGAGTTGCGGGCCCTCTGTGTGGCAGCCAGGGCCCCCCGACGCATGCATGCCTCCTC
GCACATCCCGCACAGGCTGGTGACCCTGGCCTCCGGCGCGGCGGCGGGGCGCTTCCTCAAGT
ACGAGAGaagctt
【FIG. 4A】
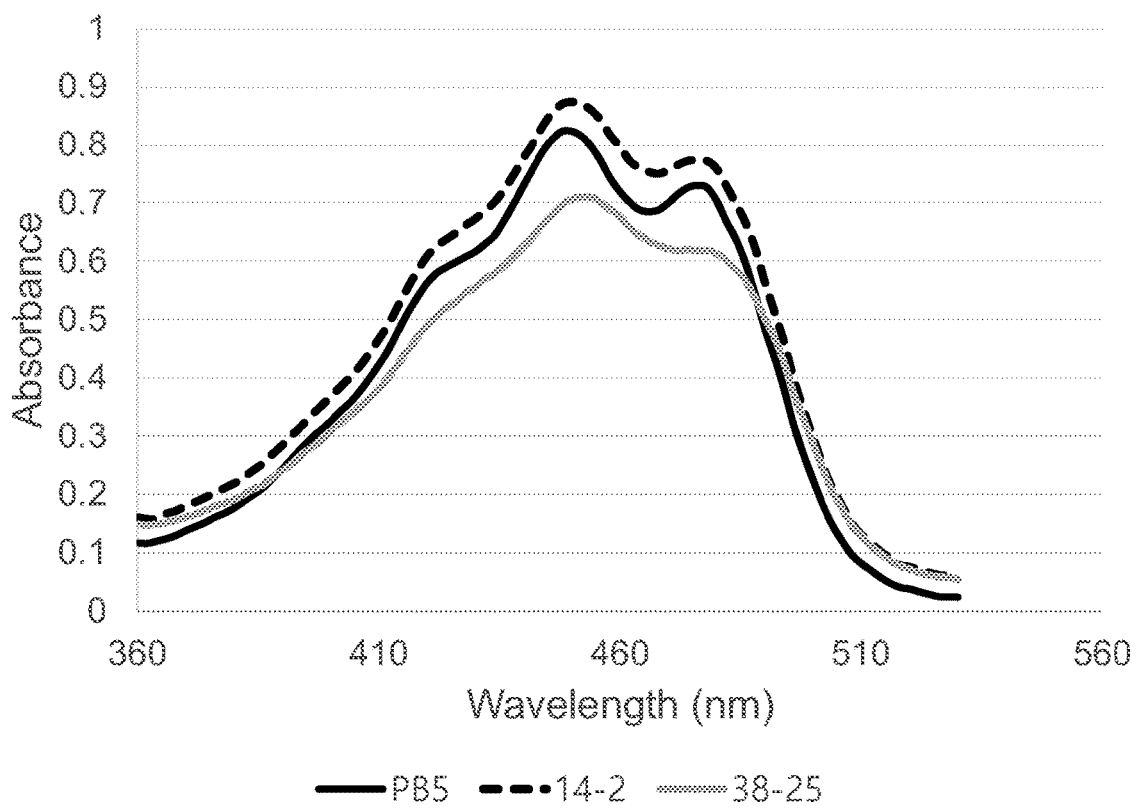

【FIG. 4B】
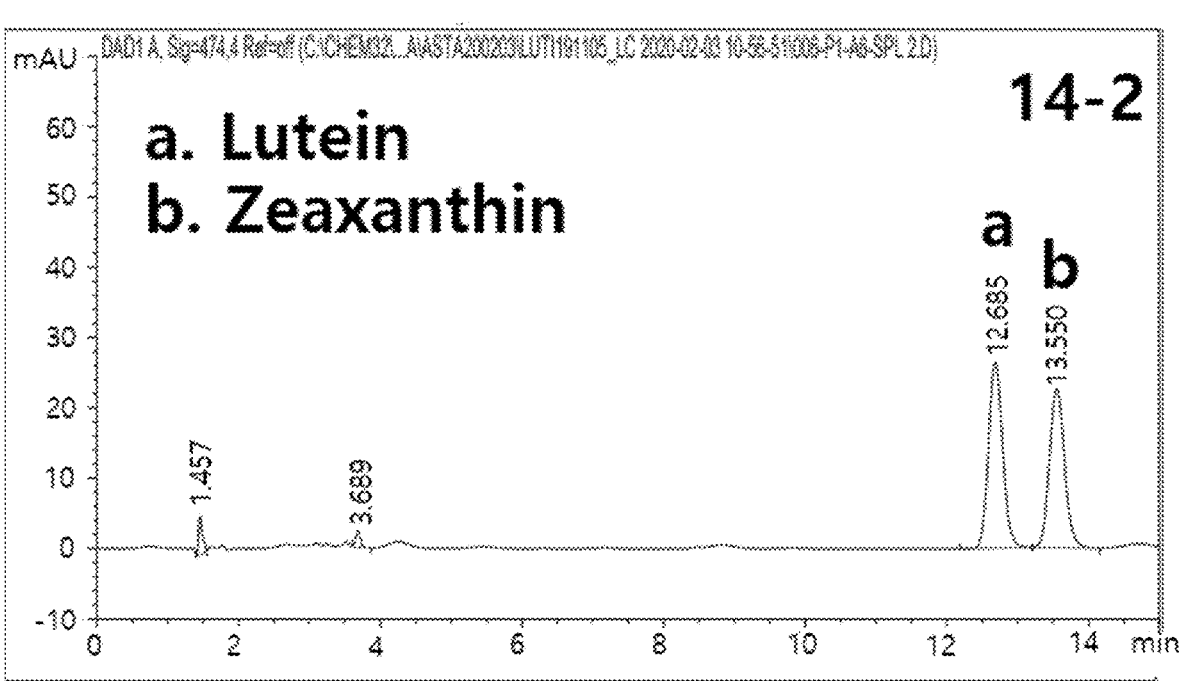

【FIG. 4C】
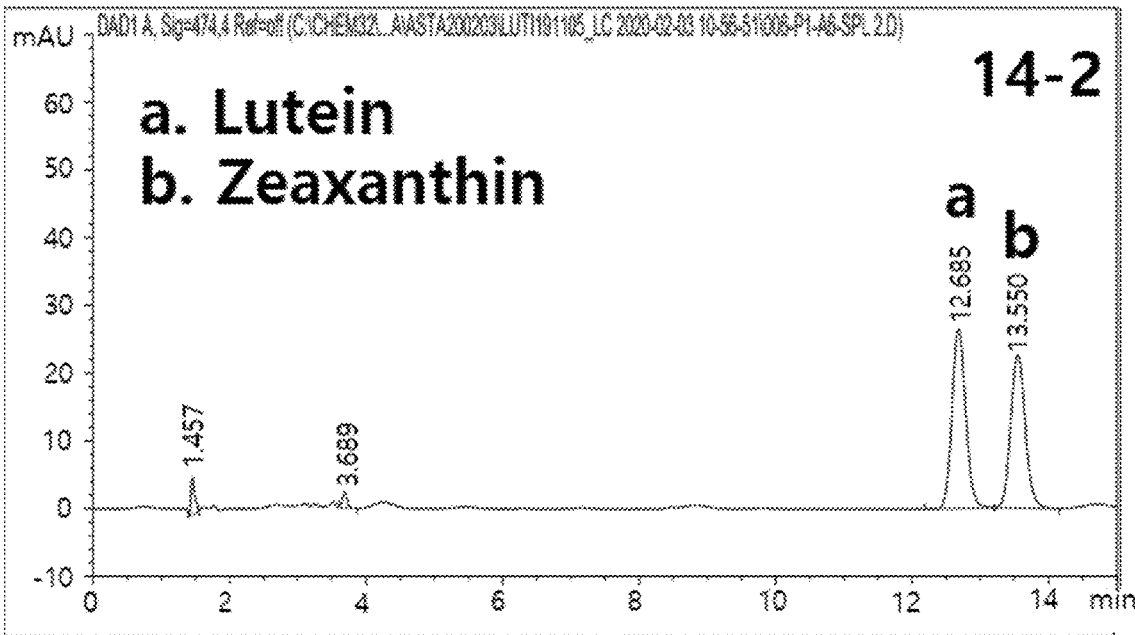
【FIG. 4D】
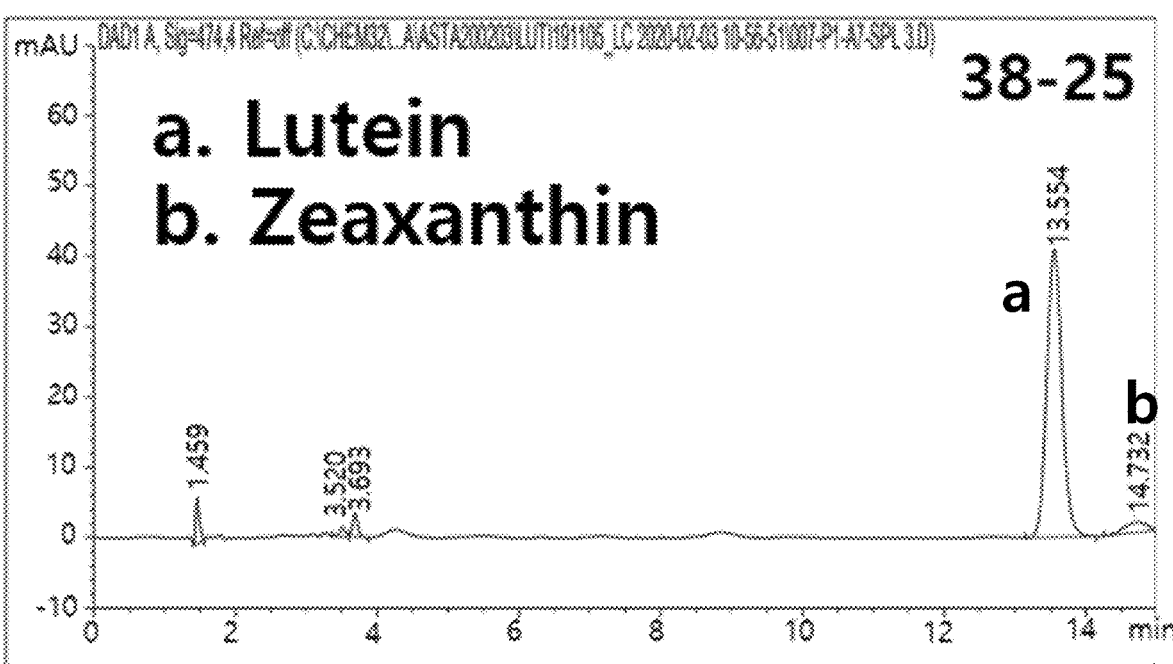

【FIG. 5】 ggtacccttgcagtgccccaaaaaactggctaccacctaacaattctcacgcagttttatcctctgcacttgatgtcagcttttgattcgtctgcgta cattacagcgttgagtggccagcaggaaggagaccgcggtccgagacgagtctgagggcgcgctctcgcaacttggattccggatttcttac cctgcatcgacctcggcctggagtcgatcagaaattgtcattgccagattgcctggcgaggacgggtgatatactcaaggcgttgcatcgccc acaaaacacacacttatctgcaagggagttactgcatcaggctctgctcaacagctcgtgacatcgatcgttcagctcccagcaggtgcgtgt ccgcatggagcacccctcccgagacacctgcgttgggtgtcggaggagctcacatgccagggaggtgcccacattgcaccacgcgaccgc gaaataggcagacttcgggcatcctgtcatcgcatgtccgctggccgggaatcatggcctccccaccaggcgtcacgcgctgcccacctcc tccccttgctgcgcagggcaccgcgttcctgtggagagccgaccad*ATG*ggcccccggcatccagcccacctccgcccgcccctgctcccg

*caccaagcactcccgcttcgccctgctggccgccgccctgaccgcccgccgcgtgaagcagttcaccaagcagttccgctcccgccgcatg*

*gccgaggacatcctgaagctgtggcagcgccagtaccacctgccccgcgaggactccgacaagcgcaccctgcgcgagcgcgtgcacct*

*gtaccgccccccccgctccgacctgggcggcatcgccgtggccgtgaccgtgatcgccctgtgggccacccctgttcgtgtacggcctgtggttc*

*gtgaagctgccctgggccctgaaggtgggcgagaccgccacctcctgggccaccatcgccgccgtgttcttctccctggagttcctgtacacc*

*ggcctgttcatcaccacccacgacgccatgcacggcaccatcgccctgcgcaaccgccgcctgaacgacttcctgggccagctcgcgatctc*

*cctgtacgcctggttcgactactccgtgctgcaccgcaagcactgggagcaccacaaccacaccggcgagccccgcgtggaccccgacttc*

*caccgcgggcaaccccaacctggccgtgtggttcgcccagttcatggtgtcctacatgacccctgtcccagttcctgaagatcgccgtgtggtcca*

*acctgctgctgctggccggcggcgccccccctggccaaccagctgctgttcatgacccgccgcccccatcctgtccgcctccgcctgttctactacggc*

*acctacgtgcccaccacccccgagaagggccacaccggcgccatgccctggcaggtgtcccgcacctcctccgcctccgcctgcagtcct*

*tcctgacctgctaccacttcgacctccactgggagcaccacacgctggccctacgcccctggtgtgagctgcccaagtgccgccagatcgcc*

*cgcggcgcccgcctggcc*TGAGCGGAGGCCTTGGAAATATTCGCGTCACGCGAGGAGTAGGCTCTGCTGGTCGGCCCT

GGATACGCTGACTCTTCAAGCAGTGGGGCACCACACCCACCTTTTGCCAAGGGCAAGGAGTCGGAAGGGGGCGGG

GCTGCCATGCACCCCTGACGGGCATGGCCGTTCCGCGAGGGCGCCAACTGCGGCGGCCTGCCCGCTGGCTCGTGC

CCCCCTACCCCCACCATTGCCTGGAGCGTTTCCATCCCCAAATCACATTCCATCCAAGTTGTATCACTATGCCCCTTTG

GCTCTATACACTCACGGCCTGAGGTCCCTTCTCGGCCGTGGCGGCACACGCCCAACCCCCCACCATACTCTTTCCAT

ACACTGCAATGCTTCGAGCCTGCCTGCCACCTGCTCTGCTTGTCTCCCCTCCCTTCCCTTGAGGTTTTCCAATGCAGT

AAGAGAAGTCGACGTGCATGGACAGATGATTGAGAGATGAGACTAGT

【FIG. 6】

*ATGgccaccgcatccactttctcggcgttcaatgcccgctgcggcgacctgcgtcgctcggcggcgctccggacccccggcgcc*

*cagcgaggcccctccccgtgcgcgctgccatccgctcccgccgcatggccgaggacatcctgaagctgtggcagcgccagt*

*accacctgccccgcgaggactccgacaagcgcaccctgcgcgagcgcgtgcacctgtaccgccccccccgctccgacctg*

*ggcggcatcgccgtggccgtgaccgtgatcgccctgtggccacctgttcgtgtacggcctgtggttcgtgaagctgccctgg*

*gccctgaaggtgggcgagaccgccacctcctgggccaccatcgccgccgtgttcttctccctggagttcctgtacaccggcctg*

*ttcatcaccacccacgacgccatgcacggcaccatcgccctgcgcaaccgccgcctgaacgacttcctgggccagctcgcg*

*atctccctgtacgcctggttcgactactccgtgctgcaccgcaagcactgggagcaccacaaccacaccggcgagccccgcg*

*tggaccccgacttccaccgcggcaaccccaacctggccgtgtggttcgcccagttcatggtgtcctacatgaccctgtcccagtt*

*cctgaagatcgccgtgtggtccaacctgctgctgctggccggcgccccccctggccaaccagctgctgttcatgaccgccgccc*

*ccatcctgtccgccttccgccctgttctactacggcacctacgtgccccaccacccccgagaagggccacaccggcgccatgccc*

*tggcaggtgtcccgcacctcctccgcctcccgcctgcagtccttcctgacctgctaccacttcgacctccactgggagcaccacc*

*gctggccctacgcccccctggtgggagctgcccaagtgccgccagatcgcccgcggcgccgccctggccTGA*

【FIG. 7A】

MGPGIQPTSARPCSRTKHSRFALLAAALTARRVKQFTKQFRSRRMAEDILKLWQRQYHLP
REDSDKRTLRERVHLYRPPRSDLGGIAVAVTVIALWATLFVYGLWFVKLPWALKVGETATS
WATIAAVFFSLEFLYTGLFITTHDAMHGTIALRNRRLNDFLGQLAISLYAWFDYSVLHRKHW
EHHNHTGEPRVDPDFHRGNPNLAVWFAQFMVSYMTLSQFLKIAVWSNLLLLAGAPLANQL
LFMTAAPILSAFRLFYYGTYVPHHPEKGHTGAMPWQVSRTSSASRLQSFLTCYHFDLHWE
HHRWPYAPWWELPKCRQIARGAALA*

【FIG. 7B】

<u>MATASTFSAFNARCGDLRRSAGSGPRRPARPLPVRAA</u>IRSRRMAEDILKLWQRQYHLPRE
DSDKRTLRERVHLYRPPRSDLGGIAVAVTVIALWATLFVYGLWFVKLPWALKVGETATSWA
TIAAVFFSLEFLYTGLFITTHDAMHGTIALRNRRLNDFLGQLAISLYAWFDYSVLHRKHWEH
HNHTGEPRVDPDFHRGNPNLAVWFAQFMVSYMTLSQFLKIAVWSNLLLLAGAPLANQLLF
MTAAPILSAFRLFYYGTYVPHHPEKGHTGAMPWQVSRTSSASRLQSFLTCYHFDLHWEH
HRWPYAPWWELPKCRQIARGAALA*

| parent | - | PBS | 14-2 | PBS | PBS | 14-2 | 14-2 |
| construct | - | pPB0014 | pPB0038 | pPB0120 | pPB0123 | pPB0120 | pPB0123 |
| strain | PBS | 14-2 | 38-25 | 120A-2 | 123A-5 | 120B-5 | 123B-24 |

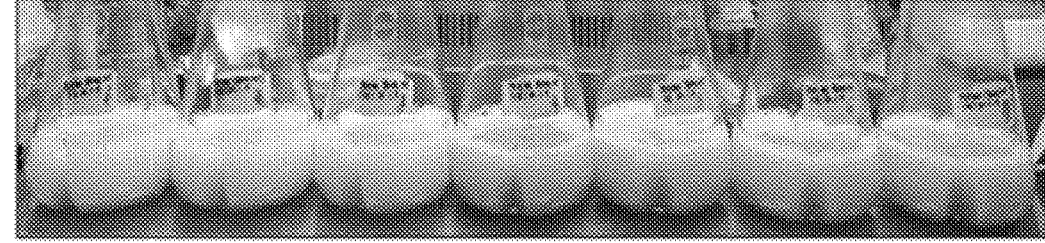

【FIG. 8B】
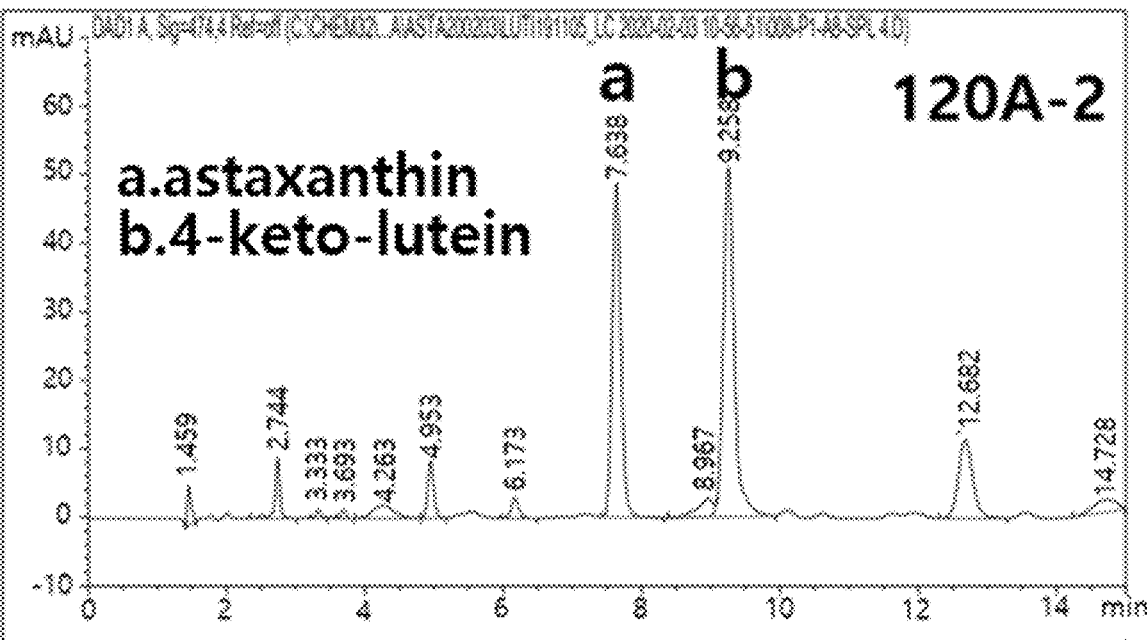
【FIG. 8C】
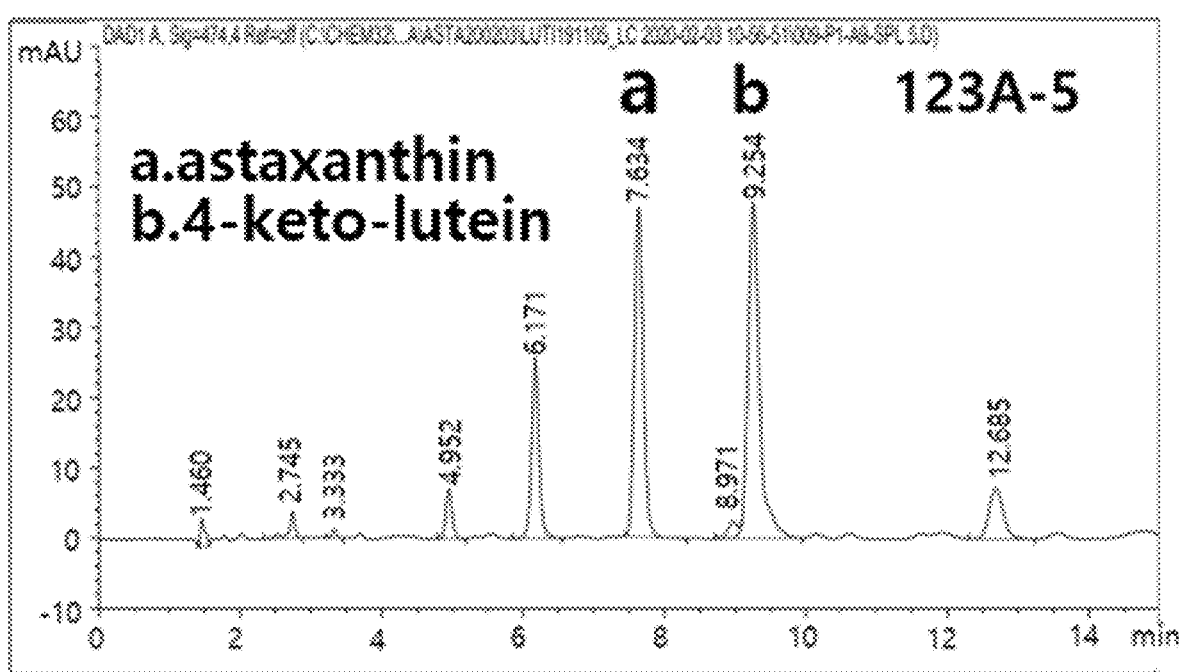

【FIG. 8D】
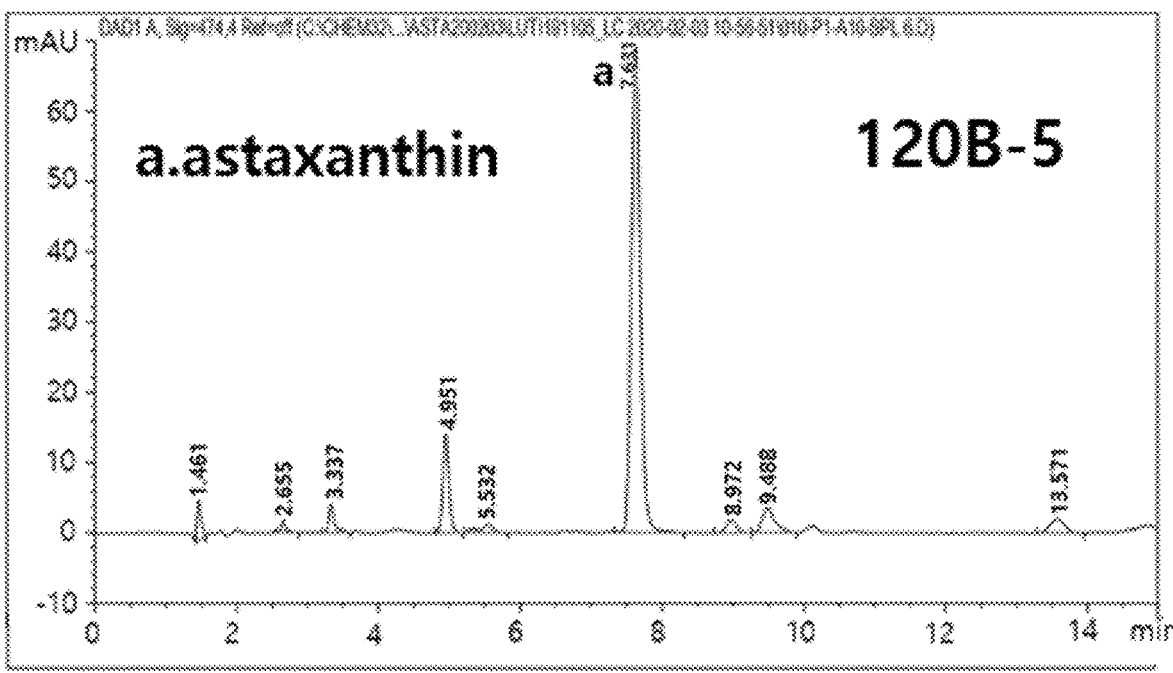
【FIG. 8E】
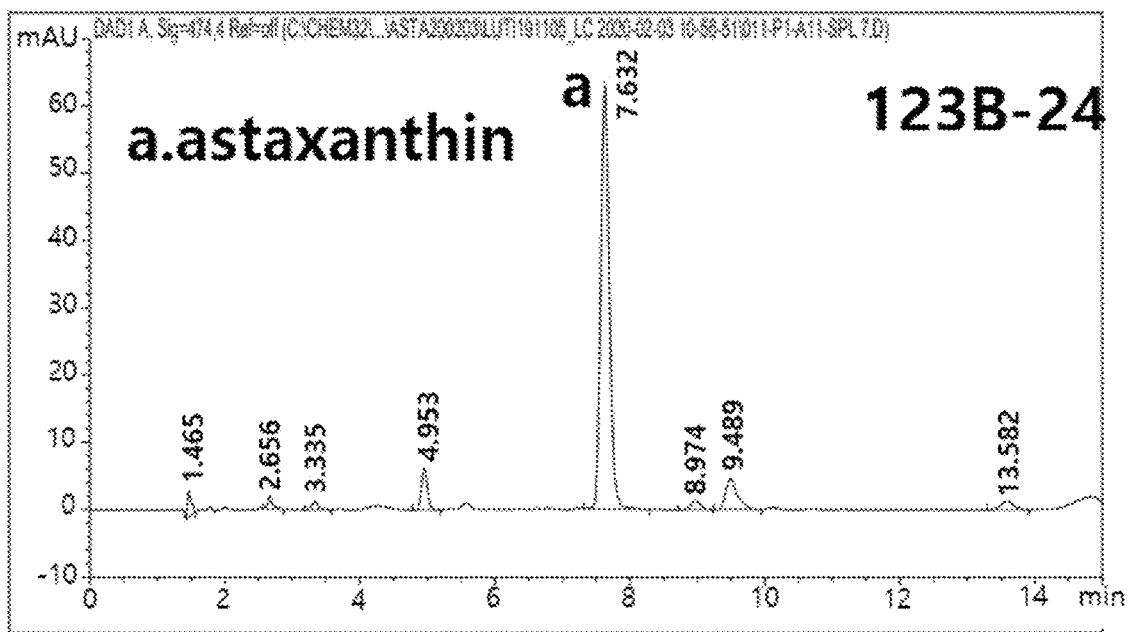

【FIG. 9A】 aagcttTCACTGCTCCATTCACACCCAATTTCCCACCGCCGCACCCGCTCCCAGGTGGGAGGATGG

GAGGGAACCCAGCTGGGAGCCGGAGGAGCATGTGACCCCGGACCTGATCGAGCTATATGCCGC

CAGGGACGCTCGAGCACGGGATGTCAAGGCCGCGGCTGACAAGGCTGGCAAGGGTAGGACAC

CTGCGTTGAGGCAAACGCTGGAGACGGCCGGTCTCAGCATGTGATCCTGTACTTGCTGTGACAA

GGTGGACAATGCAGTACGAGGTGTACCAGGCTAAGTATTCCTAGTATACCGGCACGCCAGATCAT

CTGTACAGGAGTCTGTGCAGGAGTGAAAAGGTAAGAGCCAGAGCCATGACCGGCGACCATCCAT

GTCCCGTCACTCGGATGCACTGGCTGACATCGGCGGCAGGTCATCCAACGGTCCTGAATGATCG

AGAGGAAGCTGCCCGATTTCAAAACGCCCCCCCACGTCGCCCTCCATGGCCGCACAGCATGCT

CAGCACAGGTTGCTGCGTGTCCTCACACAAACTGCTCCTTTAAAGCGATCAACTTTCCAGGGCAT

GGGGCACTCGTACTGACAATCACCCACATTCGTATACCTTTGACGTCATTATTTTTTCGCCCCAAC

GCGGTTGCCATCCCGAGTTGTACCTCCGCGGCTACCATACCCCTGTCTTCTGGCCCTCACCGTC

GCTCGCAGGCGGGATCCAGCGCAGCCAGTCTGAATACTTTTACACAACATAGTACGTAACGCGCA

TTAGGCCCCCAATACCAGCAGCTGGCTCCAGCATGGGCAAGGGTGCGCGGCAGGAGgaattcccc gctttttaattgagcccttcgtcgctgaatcagcgaaagcaccgcgaaacaatgcctgtccgtccatgcatctcaacagcctcatgcaaggt ttgcacaagcaagaccattctgatctgggaacttgtaggtgttgtatggggggaggttgtgctcttgaatcaagtggtatcacgtttccggaacacct ccgaaacgtgcatggggcttattgcgatgagagcatttccaccgcgattgtctcacgcgcatttcggagaaggtttgcagaacactccaggad atgaaatgcctgtcacgtatgaaccatctcccacggccttgaaaagatcgctcgacttccattctagatggtgcaaaaccctacgactcaaga aggtgccaccgactcaggcattgggcacggcgggcagggagaagagaggagttgatcaaaactgctcgatcacgttccccatggcgatc cgagcagcacatgatgcatcgaggtggcgccgttgcaaaggagttgcgcatgggtcgaagcagggagaaggaaacggcgaggcgtgcc gcggggggtgaattcagagtcaaatctgcgcctgccccggcgctcctgacgggggattaaccccacgactgtatccatcgacactcgtctcgg gggaataaaaagcggcgacccagctccagaggcgcaatcctctcacaatctgtttaacttcaacaaagtataagtcaattcaacttgacaca

*ATGgccgcgtccgtccactgcacccgatgtccgtggtctgcaacaacaagaaccactccgccccgccccaagctgcccaactcctcctgc*

*tgcccggcttcgacgtggtggtccaggccgcggccacccgcttcaagaaggagacgacgaccaccccgcgccacgctgacgttcgaccccc*

*ccacgaccaactccgagcgcgccaagcagcgcaagcacacatccgacccctcctccccgacttccagccatccccctccttcgaggagt*

*gcttccccaagtccacgaaggagcacaaggaggtggtgcacgaggagtccggccacgtcctgaaggtgcccttccgccgcgttgcacctgtc*

*cggcggcgagcccgccttcgacaactacgacacgtccggccccccagaacgtcaacgcccacatcggcctggcgaagctgcgcaaggag*

*tggatcgaccgcgcgcgagaagctgggcacgcccgtacacgcagatgtactacgcgaagcagggcatcatcacggaggagatgctgta*

*ctgcgcgacgcgcgcgagaagctggaccccgagttcgtccgctccgaggtcgcgcgcgggccgcgccatcatcccctccaacaagaagcacct*

【FIG. 9B】 ggagctggagcccatgatcgtgggccgcaagttcctggtgaaggtgaacgcgaacatcggcaactccgccgtggcctcctccatcgaggag gaggtctacaaggtgcagtggccaccatgtgcggcgccgacaccatcatggacctgtccacgggccgccacatccacgagacgcgcga gtggatcctgcgcaactccgcggtccccgtggggcacgtccccatctaccaggcgctggagaaggtggacggcatcgcggagaacctgaa ctggaggtgttccgcgagacgctgatcgagcaggccgagcaggggcgtggactacttcacgatccacgcgggcgtgctgctgcgctacatc cccctgaccgccaagcgcctgacgggcatcgtgtcccgcggcggctccatccacgcgaagtggtgcctggcctaccacaaggagaacttc gcctacgagcactgggacgacatcctggacatctgcaaccagtacgacgtcgccctgtccatcggcgacgggcctgcgcccccggctccatcta cgacgccaacgacacggcccagttcgccgagctgctgacccaggggcgagctgacgcgccgcgcgtgggagaaggacgtgcaggtgatg aacgagggccccggccacgtgcccatgcacaagatccccgagaacatgcagaagcagctggagtggtgcaacgaggcgcccttctaca ccctgggcccccctgacgaccgacatcgcgcccggctacgaccacatcacctccgccatcggcgcgcggccaacatcggcgcccctgggcacc gccctgctgtgctacgtgacgcccaaggagcacctgggccctgcccaacccgcgacgacgtgaaggcggggcgtcatcgcctacaagatcgcc gcccacgcggccgacctggccaagcagcacccccacgccaggcgtgggacgacgcgctgtccaaggcgcgcttcgagttccgctggat ggaccagttcgcgctgtccctggacccccatgacggcgatgtccttccacgacgagacgctgcccgcggacggcgcgaaggtcgcccacttc tgctccatgtgcggccccaagttctgctccatgaagatcacggaggacatccgcaagtacgccgaggagaacggctacggctccgccgag gaggccatccgccaggcatggacgccatgtccgaggagttcaacatcgccaagaagacgatctccggcgagcagcacggcgaggtcg gcggcgagatctacctgcccgagtcctacgtcaaggccgcgcgcagaagTGAGTCCTGGCGACCCTGCTCCCCTGACCCCTGTTC

CCCTGCGCTGCTTCTCCCCGGTGACATCCGACCTGCTGCAAAATTCCCGTTCCTGCACAACACTTGCCTGACCGAGG

GTCGGGTCGCGAAGTAAAAGCCACAATCAACACCCCAGGCACATTAAGAGTGCACAGCATGACGCAGCATAGGGTTT

GTGTCGGAGGAAGGGGGTCGAGTCGCGTTGGCGAGGGGGTGGTCACGATGACCACATCTGCGGGATAATTGAATCC

TCAGGGGAAAATACCAGTCTCTGCTTCCAGGTGCTCCGgagctcCCCAGGCGAGTCAATCAGTTGTGTCATG

AGATTGATCTGCCTGTTGCAGATCCCCCGACCCGCTGCCGGCCCCTCTGCCGTGCGACACCCCT

TGCCCTGGGGTGTGCCTCTTGTCCTGCATCGCACACCTCCTCCGCCGGACCTTCACCCCCTCCC

ACCTCGACACAAGCAGGTGTGGGACGTGATAGTGGTGGGCGCGGGCGTGGCCGGCGCGGCGC

TGGCGCATCAGCAGGGCTTGGACGGCCGACGCGTGCTGCTCCTCGAGCGGGATCTGGCCCAG

CCCGACCGCATCGTGGGCGAGCTGCTGCAGCCTGGCGGCGTGCTGGCCCTGGAGCGCCTGGG

CCTGGGCGGCGCCGTGGACGGCATCGACGCGCAGCCCGTGGTCGGGTACTGCATGTTCAAGG

GCGGGCGCGAGGCGTGCATCGCCTACCCCACCCCCGCCGAGCTGGGGGGGTCCAGCGGCTGC

GGCTGCGGCATGCAGGGGCCCCACTGGAAGCGCCAGCGCCGCGCCCGCCGGCGACGCCCCC

GTCACGGGCTTCTCCTTCCACAACGGGCGATTCGTGCAGCGGCTGCGCGCCGCGGCGGCGGC

TGCGCCCGGGGTCACGCTGCGTCGCGGCACGGTGCGCGCGCTGGTGGATGACGCCGGCGCG

【FIG. 9C】

GACTGGGAGGAGGGGCGCGTGGTGACGGGCGTGCGGTACCGCGCGGGCGACGGCGGCGAGC
GCGTGGCACTGGGCCACCTCACCGTGGTCTGCGACGGCATGTACTCGGCCCTGCGGTCCAAGC
TGGCGGTGCCCGACCTGCGCACGCCCTCCCACTTCATCaagctt

【FIG. 10A】 aagcttTCACTGCTCCATTCACACCCAATTTCCCACCGCCCGCACCCGCTCCCAGGTGGGAGGATGG

GAGGGAACCCAGCTGGGAGCCAGAGGAGCATGTGACCCCGGACCTGATCAAGCTATATGCCGC

CAGGGACGCTCGAGCACGGGATGTCAAGGCCGCGGCTGACAAGGCTGGCAAGGGCAGGACAC

CTGCGCCGAGGCAAACGCTGGAGACGGCCGGTCTCAGCATGTGATCCTGTACTTGCTGTGACAA

GGTGGACAATGCAGTACGAGTTGTACCAGGCTAAGTATCCCTAGTATACCGGCACGCCAGATCAT

CTGTACAGGAGTCTGTGCAGGAGTAAAAAGGCAACAGCCAGAGCCATGACCGGCGACTATCCAC

ATCCCGTCACTCCGATGCACTGGCTGACATCGGCGGCAGGTCGTCCAACGGTCCTGAATGATCG

AGAGGAAGCTGCCCGATTTCACCCCCCCCCCCCCACGTCGCCCTCCATGGCCGCACAGCATGCT

CAGCACAGGTTGCTGCGTGTCCTCACACAAACTGCTCCTTTAAAGCGATCAACTTTCCAGGGCAT

GGGGCACTCGTACTGACAATCACCCACATTCGTATACCTTTGACGTCATTTTTTTTTCGCCCCAAC

GCGGTTGCCATCCCGAGTTGTACCTCCGCGGCTACCATACCCCTGTCTTCTGGCCCTCACCGTC

GCTCGCAGGCGGGATCCAGCGCAGCCAGTCTGAATACTTTTACACAACATAGTACGTAACGCGCA

TTAGGCCCCCAATACCAGCAGCTGGCTCCAGCATGGGCAAGGGTGCGCGGCAGGAGgaattcttc tgcgctatgacacttccagcaaaaggtagggcgggctgcgagacggcttccggcgctgcatgcaacaccgatgatgcttcgaccccccga agctccttcggggctgcatgggcgctccgatgccgctccagggcgagcgctgtttaaatagccaggcccccgattgcaaagacattatagcg agctaccaaagccatattcaaacacctagatcactaccacttctacacaggccactcgagcttgtgatcgcactccgctaagggggcgcctct cctcttcgtttcagtcacaaccccgcaaacATGctgctgcaggcctcctgttcctgctggccggcttcgccgccaagatcagcgcctccatgac gaacgagacgtccgaccgccccctggtgcacttcaccccaacaagggctggatgaacgacccccaacggcctgtggtacgacgagaagg acgccaagtggcacctgtacttccagtacaaccccgaacgacacgtctggggggacgcccttgttctgggggccacgccacgtccgacgacct gaccaactgggaggaccagcccatcgccatcgcccccgaagcgcaacgactccggcgcgcctctccggctccatggtggtggactacaacaa caccccggcttcttcaaacgacaccatcgaccccgcgccagcgctgcgtggccatctggacctacaacaccccggagtccgaggagcagtac atctcctacagcctggacggcggctacacccttcaccgagtaccagaagaacccccgtgctggccgccaactccacccagttccgcgacccga aggtcttctggtacgagccctccagaagtggatcatgacccgcggccaagtccaggactacaagatcgagatctactcctccgacgacctg aagtcctggaagctggagtccgccgttcgccaacgagggcttcctcggctaccagtacgagtgccccggcctgatcgaggtccccaccgagc aggaccccagcaagtcctactggtgtgatgttcatctccatcaaacccggcgcccccggccggcggctccttcaaccagtacttcgtcggcagctt caacggcacccacttcgaggccttcgacaaccagtcccgcgtggtggacttcggcaaggactactacgccctgcagaccttcttcaacacccg accccgacctacgggagcgccctgggcatcgcgtgggcctccaactgggagtactccgccttcgtgcccaccaacccctggcgctcctccatg tccctcgtgcgcaagttctcctcaacaccgagtaccaggccaacccggagacggagctgatcaacctgaaggccgagccgatcctgaac

【FIG. 10B】

*atcagcaacgccggccccctggagccggttcgccaccaacaccacgttgacgaaggccaacagctacaacgtcgacctgtccaacagcac*

*cggcacccctggagttcgagctggtgtacgccgtcaacaccacccagacgatctccaagtccgtgttcgccggaccctctccctctggttcaagggg*

*cctggaggaccccgaggagtacctccgcatgggcttcgaggtgtccgcgtcctccttccctggaccgcgggaacagcaaggtgaagttcgt*

*gaaggagaacccctacttcaccaaccgcatgagccgtgaacaaccagcccttcaagagccgagaacgaccctgtcctactacaaggtgtacgg*

*cttgctggaccagaacatcctggagctgtacttcaacgacggccgacgtcgtgtccaccaacacctacttcatgaccaaccgggaacgccctgg*

*gctccgtgaacatgacgacgggggtggacaacctgttctacatcgacaagttccaggtgcgcgaggtcaag*TGATTGATTGGAACTCA

CAAAGCGGCCCACGGCTTCGAACGTCCCGTGTCAATTGCGCGGGGTGTGCCAGAGTTTCTGCGCCACCGATGCTCA

CCCTAGGGGGGGATGCCCTTTGACATTCATGTGTGCCTGCATGCACGTTTGTATCAGTCTCACCACACCTTGAAGATT

TTTGGGAGGGGGGGGGAAGTCGGAATGGAAACgagctcCCCAGGCGAGTCAATCAGTTGTGTCATGAGAT

TGATCTGCCTGTTGCAGATCCCCCGACCCGCTGCCGGCCCCTCTGCCGTGCGACACCCCTTGC

CCTGGGGTGTGCCTCTTGTCCTGCATCGCACACCTCCTCCGCCGGACCTTCACCCCCTCCCACC

TCGACACAAGCAGGTGTGGGACGTGATAGTGGTGGGCGCGGGCGTGGCCGGCGCGGCGCTGG

CGCATCAGCAGGGCTTGGACGGCCGACGCGTGCTGCTCCTCGAGCGGGATCTGGCCCAGCCC

GACCGCATCGTGGGCGAGCTGCTGCAGCCTGGCGGCGTGCTGGCCCTGGAGCGCCTGGGCCT

GGGCGGCGCCGTGGACGGCATCGACGCGCAGCCCGTGGTCGGGTACTGCATGTTCAAGGGGCG

GGCGCGAGGCGTGCATCGCCTACCCCACCCCCGCCGAGCTGGGGGGGTCCAGCGGCTGCGGCT

GCGGCATGCAGGGGCCCCACTGGAAGCGCCAGCGCCGCGCCCGCCGGCGACGCCCCCGTCA

CGGGCTTCTCCTTCCACAACGGGCGATTCGTGCAGCGGCTGCGCGCCGCGGCGGCGGCTGCG

CCCGGGGGTCACGCTGCGTCGCGGCACGGTGCGCGCGCTGGTGGATGACGCCGGCGCGGACT

GGGAGGAGGGGCGCGTGGTGACGGGCGTGCGGTACCGCGCGGGCGACGGCGGCGAGCGCG

TGGCACTGGGCCACCTCACCGTGGTCTGCGACGGCATGTACTCGGCCCTGCGGTCCAAGCTGG

CGGTGCCCGACCTGCGCACGCCCTCCCAC TTCATCaagctt

【FIG. 11】
A
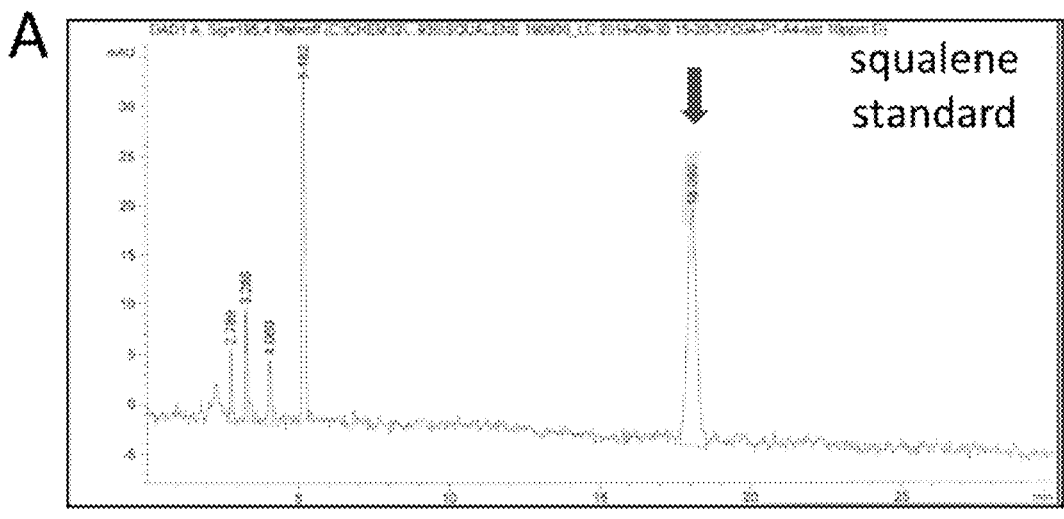
squalene
standard
B
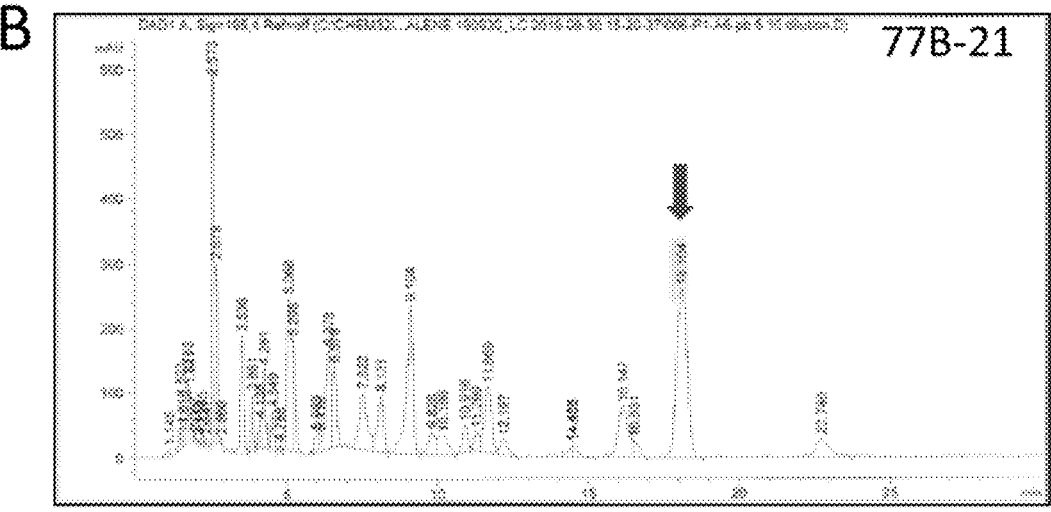
77B-21

【FIG. 12】

MQFSLAGMNTRALQTGARPSLPAARPSRRVRPARRSAPCPVARTMGGGEEQPSSAEGV

AWDKISTDELADWAGAGPPTPLLDTVAFPVHIKNFNSRQLQQLCKELRADLIHTVAKTGGH

LGSSLGVVELTVALHHVFNTPEDRIVWDVGHQAYIHKMLTGRRARMHTIRQQGGLSGFTR

RAESVYDPFGAGHSSTSVSAALGMAVGRDRKGRANNCIAVIGDGAITGGMAYEAMNHAG

FLDTNMIVILNDNQQVSLPTQYNGKNQEPVGALSSALARLQANRQLRELREIAKGVTKQLP

DVIQNATAKIDEYARGMISGTGSTLFEELGFYYIGPVDGHNMQDLVDVLSEIKATETVGPVL

LHVVTQKGRGYTPAETASDRMHGVVQYDTLTGKQKKGSGGPQSYTNYFADALVAEAKRD

ARVLGIHAAMGGGTGMNRFEAAFPDRVFDTGIAEQHAVTFAAGLATEGLVPFVAIYSTFLQ

RGYDQIVHDVSLQSLPVRFALDRAGNVGADGATHAGAFDVTYLACLPNMVVMAPSNEAE

LVHAVATAAAIDDRPSAFRFPRGNGLGVDLAAAGVTDDLKGQPMEVGRGVVRRGGADVA

LLGYGTCVNACLAAADLLAAQGVSATVVDARFCKPLDTALVRRMAAEHPVMITVEEGSIGG

FAAHVMQFLALEGLLDGKLKFRPMTLPDRYIEHGTQAEQMAEAGLTASHIAGTALSVMGV

KRDAPSIFST*

【FIG. 13】

MRCSAQLNTRGPTLPNSARPRTCRVVSASAAPVPSAWPGRVVLPEKSASRTGPKKFSLL

GSTGSIGTQTLDIVAEHPDRFQVVSLAAGGNVALLAEQIARFSPSLVSVRDSGGARALEAA

LDAAGVDRRPEIQIGAAGIDAVAAHPEADACVTGIVGCAGLRPTMAAIEAGKDICLANKETLI

AGGPTVLPAAAKHGVSILPADSEHSAIFQCLQGLPEGGLRRIILTASGGAFRDLPVSELPKV

TVADALKHPNWAMGKKITIDSATLMNKGLEVIEAHYLFGASYDNIDIVIHPQSIVHSMIETQD

SSVLAQLGWPDMRLPILYTMSWPERVPCSEVTWPRLDFVKAGNLTFRQPDHAKYPAMEL

AYSAGRAGGTMTGVMSAANEAAVELFLEEAIGYLDIVPVVEAACEAHRVELVERPSLEEIV

HYDQWARRHVRESVAKRAPAAVPAL*

【FIG. 14】

MAAVVEAGHAASKQKTEAHQTKQEFLAVFEKLRDELLEDSILAGQPESSKDWLRTMLDYN

VPHGKLNRGMAVLDVLLAARGGDVTEKEREAANVLGWCIELLQAYFLVADDIMDSSLTRR

GQPCWYRQPHVGMVAINDGIILESCIYRLLKLHFRAHPAYVHLLELFHDTTHRTAHGQLLDT

TTAPPGGVDLTRYTEGTYLRIVTYKTAFYTIYLPVACGLALAGVTDEASLALAEDLSVRMGR

YFQIQDDVLDAFGEPEVIGKVGTDIQDSKCSWLVVRALAVASAEQREAIKANYGRDDAEAV

EAVKAVYRELDLPAAFAAYEQESYDGLVQAIEGQDKFPPAVFMGILAKIYKRTK

【FIG. 15】

MGKLGELLSHPDEIIPMAAMYLAARRAAVLPHDPDLAFCYSMLNKVSRSFAIVIQQLPEQL

RDAVCVFYLVLRALDTVEDDMAIDQAEKVPILLSFHEKTYEKDWSMKCGHGHYVELMEQY

PVVCAAFQGLEPQYQEVITDICRRMGAGMAEFIVKEVETVKDYDLYCHYVAGLVGVGLSN

LFAGSGLESEDFASLHELSNGMGLFLQKTNIIRDYLEDIMEEPAPRMFWPKEIWGKHGDSL

EDFKDPENAEAAVACLNDMIADALRHVDASLDYMQRLRNRPIFRFCAVPQIMAIGTLAACF

DNPSVFTGVVKMRRGQTAKIMHDVEDYADLLAYFRAFGQALAAKARAARGKGAESVGRA

AERVVAGCSAALADLSRAENARMAAAARRPLSLPARALLLVAALLYLFLAWRAEGVRRWL

GVDSPPAAHKLDYYNQIVASMFLGYSLFAVGTGRRP*

【FIG. 16A】 aagctt<u>GCACAGTCAGTCGTCATCCACGAAGTCGCGCGCCCGTCTGTCCACCGGGGGTCTCCTGAACG</u>

<u>CAGCAATCTCCTCCTGAGTGTATGAGCCCGTGGCCGGGAGTTTGTATGCAGGGCGAGGCAAGGA</u>

<u>CGACCATGCCGGGAGAAACCCAAGGTGACGAAGTGACATTGTGCTCGATCACTCCATGCACTGC</u>

<u>CTCACTCGCCCATGTACCTTGGTCATGTACTCCCCAGTCTGCATCTTGGTGTTCCTGTTCAGCTC</u>

<u>GCGGAGCTCCTCCAGGCGCTGCTCGTCGCGGCGGTCCCGCGAGATGTAAAAGGCAGGGACAC</u>

<u>CCACCCCCAGGGCCACTCCCAGTAGAGCCCCCCCCTACAGCAACCAGGGTGTCCGGATCGCTAA</u>

<u>AGTCGATGTTGATCGCGCGGCACGGTGGCATTATCGGGCGTGGATGGCCCCATGATCGGTGCAA</u>

<u>CGAAGGCGCCCTCATGGCAGGTCCGCATGGTCGTCCATTGCAGGGGATACCCGCTCGCACTTTC</u>

<u>GTTGACAATAACATCCTCGTATAGTTGGAGAAAGGATTTGTGATCTGTCTCTGGAGGCCCTTAAAG</u>

<u>TCCTGCCCCTCCTCTGCTGGAACCTGACCTCTCATGCCCCTGCGCCACGCCCCCCGGATCTGATA</u>

<u>TGGCTCTGATATGGGTGGCTCGTACCTCTTGGCTAGGCGACCCCCCCTAAGCACGCGTGCGGGCC</u>

<u>AGGGCACAACATTATATTTTGCCCTCTCCTTCGTCAACGCTCATTTTTTTGGAATACTAACGTTTAA</u>

<u>AAGCTCTCG</u>ggtacc`cccgcttttaattgagcccccttcgtcgctgaatcagcgaaagcaccgcgaaacaatgcctgtcccgtccatg`

`catctcaacagcctcatgcaaggtttgcacaagcaagaccattctgatctgggaacttgtaggtgttgtatgggggaggttgtgtctctgaatcaa`

`gtggtatcacgtttccggaacacccgaaacgtgcatgggcttattgcgatgagagcatttcccaccgcgattgtctcacgcgcatttcggaga`

`aggtttgcagaacactccaggacatgaaatgccttgtcacgtatgaaccatctcccacggccttgaaaagatcgctcgacttccattctagatg`

`gtgcaaaaccctacgactcaagaaggtgccactgactcaggcattgggcacggcgggcagggagaagagaggagttgatcaaaactgc`

`tcgatcacgttcccccatggcgatccgagcagcacatgatgcatcgaggtggcgccgttgcaaaggagttgcgcatgggtcgaagcaggga`

`gaaggaaacggcgaggcgtgccgcgggggtgaattcagagtcaaatctgcgcctgccccggcgctcctgacggggattaaccccccacga`

`ctgtatccatcgacactcgtctcgggggaataaaaagcggcgacccagctccagaggcgcaatccttctcacaatctgtttaacttcaacaaag`

`ataagtcaattcaactgacaca`*ATGgccgcgtccgtccactgcaccctgatgtccgtggtctgcaacaacaagaaccactccgcccgccc*

*caagctgcccaactcctcctgctgcccggcttcgacgtggtggtccaggccgcggccacccgcttcaagaaggagacgacgaccacccg*

*cgccacgctgacgttcgacccccccacgaccaactccgagcgcgcccaagcagcgcaagcacaccatcgacccctcctcccccgacttcca*

*gcccatcccctccttcgaggagtgcttccccaagtccacgaaggagcacaaggaggtggtgcacgaggagtccggccacgtcctgaaggt*

*gcccttccgccgcgtgcacctgtccggccggcgagcccgccttcgacaactacgacacgtccggcccccagaacgtcaacgcccacatcgg*

*cctggcgaagctgcgcaaggagtggatcgaccgccgcgagaagctgggcacgccccgctacacgcagatgtactacgcgaagcagggc*

*atcatcacggaggagatgctgtactgcgcgacgcgcgagaagctggacccccgagttcgtccgctccgaggtcgcgcggggccgcgccatc*

*atccctccaacaagaagcacctggagctggagcccatgatcgtgggccgcaagttcctggtgaaggtgaacgcgaacatcggcaactcc*

【FIG. 16B】 gccgtggcctcctccatcgaggaggaggtctacaaggtgcagtgggccaccatgtggggcgccgacaccatcatggacctgtccacgggc cgccacatccacgagacgcgcgagtggatcctgcgcaactccgcgcgtcccgtgggcaccgtcccatctaccaggcgctggagaaggtg gacggcatcgcgggagaacctgaactgggaggtgttccgcgagacgctgatcgagcaggccgagcagggccgtggactacttcacgatcca cgcgggcgtgctgctgcgctacatccccctgaccgccaagcgcctgacgggcatcgtgtcccgcggcggctccatccacgcgaagtggtgc ctggcctaccacaaggagaaacttcgcctacgagcactgggacgacatcctggacatctgcaaccagtacgacgtcgccctgtccatcggcg acggcctgcgcccccggctccatctacgacgccaacgacacggcccagttcgccgagctgctgacccagggcgagctgacgcgccgcgcg tgggagaaggacgtgcaggtgatgaacgagggcccccggccacgtgcccatgcacaagatccccgagaacatgcagaagcagctggagt ggtgcaacgaggcgcccttctacaccctgggcccccctgacgacgacatcgcgcccggctacgaccacatcaccttccgccatcggcgcgg ccaacatcggcgcccctgggcaccgccctgctgtgctacgtgacgcccaaggagcacctgggcctgcccaaccgcgacgacgtgaaggcg ggcgtcatcgcctacaagatcgccgcccacgcggccgacctggccaagcagcacccccacgcccaggcgtgggacgacgcgctgtcca aggcgcgcttcgagttccgctggatggaccagttcgcgctgtccctggacccccatgacggcgatgtccttccacgacgagacgctgcccgcg gacggcgcgaaggtcgcccacttctgctccatgtgcggcccccaagttctgctccatgaagatcacggaggacatccgcaagtacgccgagg agaacggctacggcctcgccgaggaggccatccgccagggcatggacgccatgtccgaggagttcaacatcgccaagaagacgatctcc ggcgagcagcacggcgaggtcggccggcgagatctacctgcccgagtcctacgtcaaggccgcgcgcagaag*TGAGTCCTGGCGACC*

*CTGCTCCCCTGACCCCTGTTCCCCTGCGCTGCTTCTCCCCGGTGACATCCGACCTGCTGCAAAATTCCCGTTCCTGC*

*ACAACACTTGCCTGACCGAGGGGTCGGGTCGGCGAAGTAAAAGCCACAATCAACACCCCAGGCACATTAAGAGTGCACA*

*GCATGACGCAGCATAGGGTTTGTGTCGGAGGAAGGGGGTCGAGTCGCGTTGGCGAGGGGGTGGTCACGATGACCA*

*CATCTGCGGGATAATTGAATCCTCAGGGGAAAATACCAGTCTCTGCTTCCAGGTGCTCCG*actagtctgcagtgccccaa aaactggctaccacctaacaattctcacgcagttttatcctctgcactttgatgtcagctttttgattcgtctgcgtacattacagccgttgagtggcca gcaggaaggagaccgcggtccgagacgagtctgagggcgcgctctcgcaacttggattccggatttcttaccctgcatcgacctcggcctgg agtcgatcagaaattgtcattgccagattgcctggcgaggacgggtgatatactcaaggcgttgcatcgcccacaaaacacacacttatctgt aagggagttactgcatcaggctctgctcaacagctcgtgacatcgatcgttcagctccccagcaggtgcgtgtccgcatggagcacccctccc gagacacctgcgttgggtgtcggaggagctcacatgccagggaggtgcccacattgcaccacgcgaccgcgaaataggcagactcggg catcctgtcatcgcatgtccgctggccgggaatcatggcctcccaccaggcgtcacgcgctgcccacctccctcccttgctgcgcagggca ccgcgttcctgtggagagccgaccag*ATGGTCCTGTGCGCTGGTAGTTTGAGCTGCAGGGCGCCGCCTTCA*

*GGCGGTGCTAGGTTGGAGCGGGGGTCCCCCTTCGTGCGCCTGGGCCACCATGCCCGCCCACA*

*AGCTCGCAGACGGATGTCAGACCTCGTAATAAGGTCCATCGCAGCCCCTGCTCCGCCCCCGCTG*

*CGACCTGCATCTCAGCCTCAAGCCCCACCTGCATCAGAGACCTTCACGGTGAGTCATGATCGAG*

【FIG. 16C】

GTCGGCCCCTGCAGCGCTCGTGCTCCGGAAACGACCCGCTACTCAATCCCTGAACCATGAATAC

TTCAGGGGGGGCCGCGAACTGGCCAACCGCCCTCCCTTCTGCCCTCCAAGACATCCGCAACGCCA

TCCCGGCGGAGTGCTGGAAGAAGGACACCTTCAAGTCCTTCGCCTACCTGGCGCTAGATGTAGG

AATCGTTGCTGCCCTGGCCGTGACAGCACATGCCGTCAACTCGCCATGGCTCTGGCCCTTCTAC

TGGCTGGCGCAGGGGACCATGTTCTGGGCCCTGTTTGTCGTCGGCCACGACTGGTGCGGTTGG

AGGGGGTAATCTGGCGACCCTGCAGGGCATGCAGTGGGGACAAGAGCATCGCCAGGCTCCGCC

TTGCCTGCTGATCCCAGCCCGACTTGGCTGGACAATAGATGCTGTCGGGGACATGCCGCAGTGC

ATGCCACAATGGGCCCCTTCAACAACTGACCACCACTATGACCCATATTCCCTGCAGCGGCCACC

AGAGCTTCAGCACAAACAAGCAGCTGAATGACGTGGaagctt

【FIG. 17】

```
ggaatcccgcctccgagatgaagccgtggttggcacggaggaggccgctgcgggccagagtgttcttctgctgcacgtcctcc ggctttggtggctcgctgggcttgggtgcggccatgagctgcagtgcaagtgtacatataggtcaatcttatgacccggcactac caatgatgatcaacaccgagcggccctctgtgttgtgcttgcctctttaccttcactgcgtactgctgcaggagcttcatgaggatc acactgacggtcaggggatcagcacccagtcccggacatcccgatccagtacgaggtcctggctgaccatgatggtaggt gaagttgggccctgggaggagcgctagaggagcctcggggcaaagatcaccctactctgacgtggctggctcaatcaccca tccctcccctttgaagtcggctctcagtttgcgttgtttcgaaatcgagccacaatcgaatatacactacctaaaggctctcaccac ctggcgtacctcggaatgcccatcagcccaaacacatgagaaaaggcgcgcgcggttcgaccccagtccgtcgattgacgc agtggggagctccattctgtcagctcttgggtggccaggtcgctgacagattggcacatacaggaccctgccgacccgttcctc cagcactttgtgaatttaagcagcgcattagatcgtcgatggcttagagaaccccgcgcctgctcccccatctcccttcacacgt ttgaacacccggaccggcc
```

【FIG. 18A】 aagcttAGCATACTCCTATTCTGACAATGTCACAGTCGGTCTGCCAGGCGATAGTGGCTTTGCTGTC

AGACTCGGCCCCGGACTCTCCCCTGAACTGCGACGCCGGGAATCTGTTGAGAGGAGGCGATCT

GCGAGGGTTCGCCTCCATGGCCCGCATGTACACCATCGAGTATGCCATGAAGCGATGATGTCTGT

GAAAATGATGTTCAGAATTCATTATATACTCATGTTTTTGTGTAAATGCTGTGTCGACTTAAGTTACC

GAGCTGGCTGACAGAGACAATCTTCAGGTCAAATGTTGGCACCAATGATCGCGACGATCGTTCA

GGGGTTATCAAGTCAGATCTGAACGAAAACCAGAAATCAAATTTGCCAAAGCGCATGTTTGTATGT

CGAGAATTATCATGCGGGTGACTGGCTCGCTAATTCTGGCATGGAAGGATGCCACATCGAATTGA

TCCGGGGAGACTAACACTTGTCAGAATTGCAATGTGCCATATTCCAGATATCCCAGCCGGCCCTT

CTATAAACCACCTGCGGGCTCAGATACCTACGAAGAGGCTCAGATAACTCAAGGACGTGCATTCG

AATTATCCCTGCCGCGCGGAAACATCAGACCAGGTGCGGATGCTGAGCGTCGAGTTGGGTGCTT

GATAGACCTTCACCTTGATCTGAGGTTCCCGTCCCCAGAGCACTCGAATCTCCGGCATCTTACAG

GCAAACCGCAAACAGTAAATAATGGCGAGCACCATCACCATGggtaccctgcagtgccccaaaaactggctad cacctaacaattctcacgcagtttatcctctgcactttgatgtcagcttttgattcgtctgcgtacattacagcgttgagtggccagcaggaagga gaccgcggtccgagacgagtctgagggcgcgctctcgcaacttggattccggatttcttaccctgcatcgacctcggcctggagtcgatcaga aattgtcattgccagattgcctggcgaggacgggtgatatactcaaggcgttgcatcgcccacaaaacacacacttatctgcaagggagttacd gcatcaggctctgctcaacagctcgtgacatcgatcgttcagctccccagcaggtgcgtgtccgcatggagcacccctcccgagacacctgd gttgggtgtcggaggagctcacatgccagggaggtgcccacattgcaccacgcgaccgcgaaataggcagacttcgggcatcctgtcatcg catgtccgctggccgggaatcatggcctcccaccaggcgtcacgcgctgcccacctccctcccttgctgcgcagggcaccgcgttcctgtd gagagccgaccacATGtccgccgccgccgccgagaccgacgtgtccctgcgccgccgctccaactccctgaacggcaaccacaccaa cggcgtggccatcgacggcaccctggacaacaacaaccgccgcgtgggcgacaccaacacccacatggacatctccgccaagaagac cgacaacggctacgccaacggcgtgggcggcggcggcgctggcgctccaaggcctccttcaccacctggaccgccgcgacatcgtgtacgt ggtgcgctaccactggatccctgcatgttcgccgccggcctgctgttcttcatgggcgtggagtacaccctgcagatgatccccgccgcctccg agcccttcgacctgggcttcgtggtgaccgcctccctgaaccgcgtgctggcctcctccccgacctgaacaccgtgctggccgccctgaaca ccgtgttcgtgggcatgcagaccacctacatcgtgtggaccctggctggtggagaggccgcgccgcgccaccatcgccgccctgttcatgttca cctgccgcgcatcctgggctactccacccagctgccccctgcccagggacttcctgggctccgcgtggacttcccccgtgggcaacgtgtcctt cttcctgttcttctccggccacgtggccggctccatgatcgcctccctggacatgcgccgcatgcagcgcctgcgcctggccatggtgttcgacat cctgaacgtgctgctgcagtccatccgcctgctgggcacccgcggccactacaccatcgacctgccgtgggcgtgggcgccggcatcctgttcg actccctggccggcaagtacgaggagatgatgtccaagcgccacctgggcaccggcttctccctgatctccaaggactccctggtgaacTG

【FIG. 18B】

AGCGGAGGCCTTGGAAATATTCGCGTCACGCGAGGAGTAGGCTCTGCTGGTCGGCCCTGGATACGCTGACTCTTCAA

GCAGTGGGGCACCACACCCACCTTTTGCCAAGGGCAAGGAGTCGGAAGGGGGCGGGGCTGCCATGCACCCCTGAC

GGGCATGGCCGTTCCGCGAGGGCGCCAACTGCGGCGGCCTGCCCGCTGGCTCGTGCCCCCCTACCCCCACCATTG

CCTGGAGCGTTTCCATCCCCAAATCACATTCCATCCAAGTTGTATCACTATGCCCCTTTGGCTCTATACACTCACGGCC

TGAGGTCCCTTCTCGGCCGTGGCGGCACACGCCCAACCCCCCACCATACTCTTTCCATACACTGCAATGCTTCGAGC

CTGCCTGCCACCTGCTCTGCTTGTCTCCCCTCCCTTCCCTTGAGGTTTTCCAATGCAGTAAGAGAAGTCGACGTGCAT

GGACAGATGATTGAGAGATGAGactagtctttcttgcgctatgacacttccagcaaaaggtaggggcgggctgcgagacggcttccgg cgctgcatgcaacaccgatgatgcttcgaccccccgaagctccttcggggctgcatgggcgctccgatgccgctccagggcgagcgctgttta aatagccaggcccccgattgcaaagacattatagcgagctaccaaagccatattcaaacacctagatcactaccacttctacacaggccact cgagcttgtgatcgcactccgctaagggggcgcctcttcctcttcgtttcagtcacaacccgcaaadATGctgctgcaggccttcctgttcctgct ggccggcttcgccgccaagatcagcgcctccatgacgaacgagacgtccgaccgcccccctggtgcacttcacccccaacaagggctggat gaacgaccccaacggcctgtggtacgacgagaaggacgccaagtggcacctgtacttccagtacaacccgaacgacacacgtctgggga cgccctgttctggggcacgccacgtccgacgacctgaccaactgggaggaccagcccatcgccatcgcccgaagcgcaacgactccg gcgccttctccggctccatggtggtggactacaacaacaccctccggcttcttcaacgacaccatcgaccgcgccagcgctgcgtggccatct ggacctacaacacccgggagtccgaggagcagtacatctcctacagcctggacggcggctacaccttcaccgagtaccagaagaacccc gtgctggccgccaactccacccagttccgcgcgacccgaaggtcttctggtacgagcccctccagaagtggatcatgaccgcggccaagtccc aggactacaagatcgagatctactcctccgacgacctgaagtcctggaagctggagtccgcgttcgccaacgagggcttcctcggctaccag tacgagtgccccggcctgatcgaggtcccaccgagcaggacccagcaagtcctactgggtgatgttcatctccatcaacccccggcgcccc ggccggcgggctccttcaaccagtacttcgtcggcagcttcaacggcacccacttcgaggccttcgacaaccagtccgcgcgtggtgacttcgg caaggactactacgccctgcagaccttcttcaacaccgacccgacctacgggagcgccctgggcatcgcgtgggcctccaactgggagtac tccgccttcgtgcccaccaacccctggcgcctcctccatgtccctcgtgcgcaagttctccctcaacaccgagtaccaggccaaccccggagacg gagctgatcaacctgaaggccgagcgcgatcctgaacatcagcaacgccggcccctggagccggttcgccaccaacaccacgttgacgaa ggccaacagctacaacgtcgaccctgtccaacagcaccggcaccctggagttcgagctggtgtacgccgtcaacaccacccagacgatctc caagtccgtgttcgcggaccctctccctctggttcaagggcctggaggaccccgaggagtacctccgcatgggcttcgaggtgtccgcgtcctcc ttcttcctggaccgcgggaacagcaaggtgaagttcgtgaaggagaaccccctacttcaccaaccgcatgagcgtgaacaaccagcccttca agagcgagaacgacctgtcctactacaagtgtgtacggcttgctggaccagaacatcctggagctgtacttcaacgacggcgacgtcgtgtcc accaacacctacttcatgaccacgggaacgccctgggctccgtgaacatgacgacgggggtggacaacctgttctacatcgacaagttcc aggtgcgcgaggtcaagTGATTGATTGGAACTCACAAAGCGGCCCACGGCTTCGAACGTCCCGTGTCAATTGCGCGGG

GTGTGCCAGAGTTTCTGCGCCCACCGATGCTCACCCTAGGGGGGGGATGCCCTTTGACATTCATGTGTGCCTGCATGCA

【FIG. 18C】

CGTTTGTATCAGTCTCACCACACCTTGAAGATTTTTGGGAGGGGGGGGGAAGTCGGAATGGAAACctcgagCAACG

CTACGCAACTCCCTTCGATGGCTTCAAGTACGGAGATGTGGGCATCCAGGATTCGCATGTGCTGC

TTCAGCCCTCCTCATGCCACTAGCACTCATTTTTCGACTCCCGGATTGCCAGGTTCAAGGGCATC

AAGGAGTCGGAGATCAGCCGCGCCATGACCTCCCGCTACTTCGAGGACCTAAACGTCAATGCCG

AGGTGCTTTTGCATATATTTACAGCTAATTATGATGGGTGTGGTGCGCGATATGCTTGCAAGGTCTC

CGGTGAGCTAATGATCGGCACATCCCTTCCGCGCATCCGCAGGTCGATGTCGTCATTGTTGGGG

CTGGGTCTGCGGGCCTCTCGTGCGCCTATGAGCTGAGCAAGCACCCGGATGTCAAGGTATGGG

CTGAGCAGGGCACATCCTCAGATGATGTTGCTGTAATTGCAATTGAAACTTGCGGTTGTTCCCAG

CACAGCCTCAATCAATCATGTGTGCTGCGTTGGAAACGCTATGATACCCCAGCCTTCAACATGGG

GCAGGGATATCGTTTACACCTGCTTGAACCCCCCGCAACAGGTGGCCATCATCGAGCAGGGCGT

CGCCCCTGGGGGTGGAGCGTGGCTGGGGGGTCAGCTCTTCTCGGCTATGTGTGTGAGTCTAGG

CACGGGGACGGGTGGACTGAAGCAAGGGTTGGGCGCAGGGTGTTGATATCCATGTGTTGGACA

TTCTCGTTGGGAAAACAAGATGTGTGTATTTAGTGCTATCTCGGTGGCTGCATTCCaagctt

【FIG. 19A】 aagcttAGCATACTCCTATTCTGACAATGTCACAGTCGGTCTGCCAGGCGATAGTGGCTTTGCTGTC

AGACTCGGCCCCGGACTCTCCCCTGAACTGCGACGCCGGGAATCTGTTGAGAGGAGGCGATCT

GCGAGGGTTCGCCTCCATGGCCCGCATGTACACCATCGAGTATGCCATGAAGCGATGATGTCTGT

GAAAATGATGTTCAGAATTCATTATATACTCATGTTTTTGTGTAAATGCTGTGTCGACTTAAGTTACC

GAGCTGGCTGACAGAGACAATCTTCAGGTCAAATGTTGGCACCAATGATCGCGACGATCGTTCA

GGGGTTATCAAGTCAGATCTGAACGAAAACCAGAAATCAAATTTGCCAAAGCGCATGTTTGTATGT

CGAGAATTATCATGCGGGTGACTGGCTCGCTAATTCTGGCATGGAAGGATGCCACATCGAATTGA

TCCGGGGAGACTAACACTTGTCAGAATTGCAATGTGCCATATTCCAGATATCCCAGCCGGCCCTT

CTATAAACCACCTGCGGGCTCAGATACCTACGAAGAGGCTCAGATAACTCAAGGACGTGCATTCG

AATTATCCCTGCCGCGCGGAAACATCAGACCAGGTGCGGATGCTGAGCGTCGAGTTGGGTGCTT

GATAGACCTTCACCTTGATCTGAGGTTCCCGTCCCCAGAGCACTCGAATCTCCGGCATCTTACAG

GCAAACCGCAAACAGTAAATAATGGCGAGCACCATCACCATGggtaccctgcagtgccccaaaaactggctact caacctaacaattctcacgcagtttatcctctgcactttgatgtcagcttttgattcgtctgcgtacattacagcgttgagtggccagcaggaagga gaccgcggtccgagacgagtctgagggcgcgctctcgcaactggattccggatttcttaccctgcatcgacctcggcctggagtcgatcaga aattgtcattgccagattgcctggcgaggacgggtgatatactcaaggcgttgcatcgcccacaaaacacacacttatctgcaagggagttact gcatcaggctctgctcaacagctcgtgacatcgatcgttcagctccccagcaggtgcgtgtccgcatggagcacccctcccgagacacctgc gttgggtgtcggaggagctcacatgccagggaggtgcccacattgcaccacgcgaccgcgaaataggcagacttcgggcatcctgtcatcg catgtccgctggccgggaatcatggcctccccaccaggcgtcacgcgctgcccacctcctccccttgctgcgcagggcacgcgcgttcctgtc gagagccgaccacATGtcccccccccaactccatgtccccccgccaccaacggctccaccaacggcgtggccatcaacggcgccaagaa gctgctggacttcgacccctccgccgccccccccttcaagatcgccgacatccgcgcccgccatccccccccactgctgggtgaagaacccct ggcgctccctgtcctacgtgctgcgcgcgaccctgctggtgatcctgtccttcgccgtggccgccaccaagctggactcctggaccccgtgtggccccctg tactggatcgcccagggcaccatgttctgggccgtgttcgtgctggccaacgactgcggccacggctccttctccgactcctggctgctgaaca acgtgatgggccacatcctgcactcctccatcctggtgccctaccacggctggcgcatctcccacaagaccccaccaccagaaccacggcaa cgtggagaaggacgagtcctgggtgcccctgccgagaaggtgtacaagtccctggacaccggcaccaagttcatgcgcttcaccatcccc ctgcccatgttcgcctaccccatctacctgtggcgcgcgctcccccggcaagaagggctcccacttcaaccccctactccgacctgttcgccccca acgagcgcacctccgtgatgatctccaccctgtgctggaccgccatggccctgctgctgtgctactcctccttcatctacggcttcctgcccgtgtt caagatctacggccgtgccctacctgatcttcgtggcctggctggacatggtgacctacctgcaccaccacggctacgagcagaagctgccctg gtacaggggcaaggagtggtcctacctgcgcggcggcctgaccaccgtggaccgcgactacggcgtgatcaacaacatccaccacgaca

【FIG. 19B】

*tcggcacccacgtgatccaccaccctgttcccccagatgccccactaccacctggtggaggccacccaggccgccaagcacgtgctgggca*

*agtactaccgcgagcccaagaagtccggccccttcccccttccacctgttcggctacctggtgcgctccctgggcgaggaccactacgtgtccg*

*acacccggccgacgtggtgttctaccagtccgacccccacatccccaagttccccacctccgccaccaccaagtccaagtcctcctgag*TGAT

CCGGGAGGAGGGAGTGAGCGGGGGAAGGGGGCAGCCCACACGGGGCCCGTCTCGACCTGCCACCCCTCCCCTCGTC

GAGCCCTGCCCAGGGGGCGCCGCAACGAGCCATGCGTGTGCATGTGTCTGGAGGGCCCTTCCACCGGGCGATGTG

CGAGCCATCCTCGCCTATTTCAACACACCGCTGCCGGCATGCGCTCCACTCCCCCCAAAACCACCTCGACCCTCCCA

GGGCTCCTCCCCCGCCCCACCCTGCCTGCTGATATAGAAACCAGTGTTCTGTGAACGTTTGACATGCTCAACGAGGG

TACAGGGGTGCACCAACAGAGGAGGAGTGGTTCACACAGTCGGATACactagtcctcctgtcccacaatgcttggtgaatgca gtgggttgatcaccgcggaggagctgtggcttactcgttctgatcaagggagcctctgcaccttaaccctgccaggatcgaaaccaaccttgtc agtcccgtggtgggcaacatcatcctcgtgaagctgattgaccaggaaaacatgatgagtcggtatgaggacgagcatgagtggcccaaca tcgatatgacacatcttggagtttacggcaaatgtatcacactccatcctggcttgcaccacaatattagtggacccctcctgcagtggcacggt gagaagctagtttgtagtaatcttcttaattgacgaaccagacgtgtgtaatggcctcctttgagtgatggaaggatggaacctacccccccccctc cccagtactctgcggtacatccgagtaacccttccattgatcagcccaaacgcaatatgcaacgactcacatacggccaccgagtgcttattc cttcgctatcaccgcacaaaaatcccatccgcgaactcatccgaggtgatagattgcgatcggggttattcgggtaaggtgcgactagggatc cctgaatcttttggggatttccccgggtctcgtcctgcatgcttatcatcagtctcgtgggttatttggatcgctgcgcatgccataacagagcgctca taatatttgctgcggcggtggtgctggcaaaatcccctgcgtaccgggcgcctgtcaagccaacccccgccgtgcggcactccctgcagatcc atcacc*ATGatcgagcaggacggcctccacgccggctccccgccgcctgggtggagcgcctgttcggctacgactgggcccagcagac*

*catcggctgctccgacgccgccgtgttccgcctgtccgcccagggccgccccgtgctgttcgtgaagaccgacctgtccggcgcctgaacg*

*agctgcaggacgaggccgccgcctgtcctggctggccaccacggcgtgccctgcgccgccgtgctggacgtggtgaccgaggccggcc*

*gcgactggctgctgctgggcgaggtgcccggccaggacctgctgtcctcccacctggcccccgccgagaaggtgtccatcatggccgacgc*

*catgcgccgcctgcacaccctggaccccgccacctgccccttcgaccaccaggccaagcaccgcatcgagcgcgcccgcacccgcatgg*

*aggccggcctggtggaccaggacgacctggacgaggagcaccagggcctggccccccgccgagctgttcgccgcctgaaggccccgcat*

*gcccgacggcgaggacctggtggtgacccacggcgacgcctgcctgcccaacatcatggtggagaacggccgcttctccggcttcatcgac*

*tgcggccgcctgggccgtggccgacccctaccaggacatcgcctggccaccgcgacatcgccgaggagctggcgcggcgagtgggccg*

*accgcttcctggtgctgtacggcatcgccgcccccgactcccagcgcatcgccttctaccgcctgctggacgagttcttc*TGAGCTGTTCCT

AGGAACGTGGAGGAGGTGCAAGGAGGGTGATCTCACCCTGGTGTGTGTCTCTTCATGGAGCTCAGATCTTGAAAACTGT

GAGGTGCTTATCCGATACCTGCTTCGTGCATGGCTTGTGCGATATGTACACGCATTTGCAGATTGGTGGGAGCAGCAG

ATTGGTGGGAGCAGCATAGAGCTTTAGAAGGGGCTTAGGAGCGGGAATGTGAAACTCAGGCGGTTGGGCCAGATGA

GAGCGCAAAGggatccCAACGCTACGCAACTCCCTTCGATGGCTTCAAGTACGGAGATGTGGGCATC

【FIG. 19C】

CAGGATTCGCATGTGCTGCTTCAGCCCTCCTCATGCCACTAGCACTCATTTTTCGACTCCCGGAT

TGCCAGGTTCAAGGGCATCAAGGAGTCGGAGATCAGCCGCGCCATGACCTCCCGCTACTTCGAG

GACCTAAACGTCAATGCCGAGGTGCTTTTGCATATATTTACAGCTAATTATGATGGGTGTGGTGCG

CGATATGCTTGCAAGGTCTCCGGTGAGCTAATGATCGGCACATCCCTTCCGCGCATCCGCAGGTC

GATGTCGTCATTGTTGGGGCTGGGTCTGCGGGCCTCTCGTGCGCCTATGAGCTGAGCAAGCACC

CGGATGTCAAGGTATGGGCTGAGCAGGGCACATCCTCAGATGATGTTGCTGTAATTGCAATTGAA

ACTTGCGGTTGTTCCCAGCACAGCCTCAATCAATCATGTGTGCTGCGTTGGAAACGCTATGATAC

CCCAGCCTTCAACATGGGGCAGGGATATCGTTTACACCTGCTTGAACCCCCCGCAACAGGTGGC

CATCATCGAGCAGGGCGTCGCCCCTGGGGGTGGAGCGTGGCTGGGGGGTCAGCTCTTCTCGG

CTATGTGTGTGAGTCTAGGCACGGGGACGGGTGGACTGAAGCAAGGGTTGGGCGCAGGGTGTT

GATATCCATGTGTTGGACATTCTCGTTGGGAAAACAAGATGTGTGTATTTAGTGCTATCTCGGTGG

CTGCATTCCaagctt

【FIG. 20】

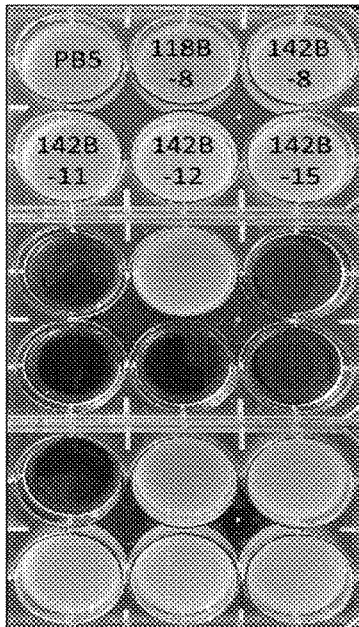

【FIG. 21】

ATGgccaccgcctccctgcccgtgcaggtggccgtgacctccacccactgcttcggcctgcgcgagccccgccgcaagcg ccagtgggcccgccagacccgctgccacgcctccgccgccggcaagcccaagcgccgcgtggtggtgaccggccagggc gtggtgacctccctgggccagtccacccagcagttctacgaccagctgctggccggcgcctccggcatcacccacatcgagg gcttcgacacctccgactactccaccaagatcgccggcgaggtgaagtccgtggacgccgcccccctacgtggccgcaagt gggtgaagcgcatggacgaggtgatgaagttcatgttcgtggccggcaagcaggccctggaggacgccggcctgcccttcg agggcccggcctggaggacctggaccgcaagctgtgcggcatcctgatcggcaccgccatgggcggcatgaccaccttcg cctccggcgtggaggccctgaccctgtccggccaccgcaagatgaaccccttctgcatcccctctccatcggcaacatgggc ggcgccatgctggccatggacctgggcttcatgggccccaactactccatctccaccgcctgcgccaccggcaactactgcat catctccgccgccgaccacatccgcaacggcgacgccgtgctgatgctggcgggcggcgccgacgccgccgtgatcccctc cggcatcggcggcttcatcgcctgcaaggccctgtcccgccgcaacgacgcccccgagcgcgcctcccgcccctgggacgc cggccgcgacggcttcgtgatgggcgagggcgccggccgtgctggtgctggaggagctggagcacgcccgcgcccgcggc gccaccatcctggccgagttcatcggcggcgcggccacctgcgacgcccaccacatgaccgagcccgagccctccggccg cggccgtgcgcctgtgcctggagcgcgcggcctggccgccgccggcgtggccccccgaggaggtgacctacgtgaacgcccacg gcacctccacccccgccggcgacgtggccgagttccgcgccatccgcgccgtgctgggccacgacggcctgcgcatcaact cctccaagggcgccatcggccacctgctgggcgcgcggcgggcgccgtggaggccgtggccaccatccaggccctgcgcacc ggctggctgcaccccaacctgaacctggacgagcccgacaagggcgtggacgcctccgtgctggtgggcggcgtgaagga gcaggccgacgtgaaggtggccctgtccaactccttcggcttcggcggccacaactcctgcgtgctgttccgcaagttcgagg agTGA

【FIG. 22】

MATASLPVQVAVTSTHCFGLREPRRKRQWARQTRCHASAAGKPKRRVVVTGQGVVTSL

GQSTQQFYDQLLAGASGITHIEGFDTSDYSTKIAGEVKSVDAAPYVARKWVKRMDEVMKF

MFVAGKQALEDAGLPFEGPGLEDLDRKLCGILIGTAMGGMTTFASGVEALTLSGHRKMNP

FCIPFSIGNMGGAMLAMDLGFMGPNYSISTACATGNYCIISAADHIRNGDAVLMLAGGADA

AVIPSGIGGFIACKALSRRNDAPERASRPWDAGRDGFVMGEGAGVLVLEELEHARARGAT

ILAEFIGGAATCDAHHMTEPEPSGRGVRLCLERGLAAAGVAPEEVTYVNAHGTSTPAGDV

AEFRAIRAVLGHDGLRINSSKGAIGHLLGAAGAVEAVATIQALRTGWLHPNLNLDEPDKGV

DASVLVGGVKEQADVKVALSNSFGFGGHNSCVLFRKFEE

SEQUENCE LISTING

```
Sequence total quantity: 18
SEQ ID NO: 1          moltype = DNA   length = 3739
FEATURE               Location/Qualifiers
misc_feature          1..3739
                      note = Nucleotide sequence of the transforming DNA from
                      pPB0014
source                1..3739
```

-continued

```
                        mol_type = other DNA
                        organism = synthetic construct
SEQUENCE: 1
aagcttcaag tgcgtgcgtt acagtgttac caacaacagt ctaacctacc cctttcggtc   60
attctgccct ttggcaagag ttcagaatga agtgtgcttg cacatcgagc tagtgctgtg  120
agcgaagaca aggaagtccc cactcaccca cgtggccaga ttctatcttt tttcagattg  180
caagggccac gcccagcgaa ccccgcgatg gggccgagcc atgcccgaca tctcgacatc  240
ttcatatgat aaggcgcttc aaagtgcaat ttttgtgcat ggcatcaatt aggagagtgc  300
ttgaacacca gcccatcttc caccggggaa ggaccgtcga aatgcctctg cagacggcca  360
ccgtctgatc gctgcctgtc ccgaggtgac ggcgatgtcg tccttatccc aaacaatcgt  420
tcgaagacct ttcttttgtt cgctcaaccc accgaggaga ccgtctggat tccatgctgc  480
tgtgacgcct agcccctga gaccctccaa gtgggcggtc ccctccctag cccccagcct  540
ctctgacgtg gcagatgcct ccgcggaagc aaatcaggat cgcagggagg gctcctacga  600
gcagcccctg gtccaacgcc aggtgcctag ggggaaagga gggcagaggg gcttgaggcg  660
agcctggccc aggcagggct tccatggtca gtcgtggcag tgccatgaca gccgaagccc  720
aacgcgacac cgtgggtgca gcatgcgtgg acggaaacat tggcaatgcc ttgccccatt  780
ggcccccag gcccggaaac gggacgatca gcaggacccc ttgtccagcc tcctcatcc   840
ggtaccctt cttgcgctat gacacttcca gcaaaaggta gggcgggctg cgagacggct  900
tcccggcgct gcatgcaaca ccgatgatgc ttcgaccccc cgaagctcct tcggggctgc  960
atgggcgctc cgatgccgct ccagggcgag cgctgtttaa atagccaggc ccccgattgc 1020
aaagacatta tagcgagcta ccaaagccat attcaaacac ctagatcact accacttcta 1080
cacaggccac tcgagcttgt gatcgcactc cgctaagggg gcgcctcttc ctcttcgttt 1140
cagtcacaac ccgcaaacat gctgctgcag gccttcctgt tcctgctggc cggcttcgcc 1200
gccaagatca gcgcctccat gacgaacgag acgtccgacc gcccctggt gcacttcacc 1260
cccaacaagg gctggatgaa cgaccccaac ggcctgtggt acgacgagaa ggacgccaag 1320
tggcacctgt acttccagta caacccgaac gacaccgtct gggggacgcc cttgttctgg 1380
ggccacgcca cgtccgacga cctgaccaac tgggaggacc agcccatcgc catcgccccg 1440
aagcgcaacg actccggcgc cttctccggc tccatggtgg tggactacaa caacacctcc 1500
ggcttcttca cgacaccat cgacccgcgc cagcgctgcg tggccatctg gacctacaac 1560
accccggagt ccgaggagca gtacatctcc tacagcctgg acggcggcta cacctcaac 1620
gagtaccaga agaaccccgt gctggccgcc aactccaccc agttccgcga cccgaaggtc 1680
ttctggtacg agccctccca gaagtggatc atgaccgcgg ccaagtccca ggactacaag 1740
atcgagatct actcctccga cgacctgaag tcctggaagc tggagtccgc gttcgccaac 1800
gagggcttcc tcggctacca gtacgagtgc cccggcctga tcgaggtccc caccgagcag 1860
gaccccagca gtcctactg ggtgatgttc atctccatca accccggcgc cccggccgagc 1920
ggctccttca accagtactt cgtcggcagc ttcaacggca cccacttcga ggccttcgac 1980
aaccagtccc gcgtggtgga cttcggcaag gactactacg ccctgcagac cttcttcaac 2040
accgacccga cctacgggag cgccctgggc atcgcgtggg cctccaactg ggagtactac 2100
gccttcgtgc ccaccaaccc ctggcgctcc tccatgtccc tcgtgcgcaa gttctccctc 2160
aacaccgagt accaggccaa cccggagacg gagctgatca acctgaaggc cgagccgatc 2220
ctgaacatca gcaacgccgg cccctggagc cggttcgcca ccaacaccac gttgacgaag 2280
gccaacagct acaacgtcga cctgtccaac agcaccggca ccctggagtt cgagctggtg 2340
tacgccgtca acaccacccca gacgatctcc aagtccgtgt tcgcggacct ctccctctgg 2400
ttcaagggcc tggaggaccc cgaggagtac ctccgcatgg gcttcgaggt gtccgcgtcc 2460
tccttcttcc tggaccgcgg gaacagcaag gtgaagttcg tgaaggagaa cccctacttc 2520
accaaccgca tgagcgtgaa caaccagccc ttcaagagcg agaacgacct gtcctactac 2580
aaggtgtacg gcttgctgga ccagaacatc ctggagctgt acttcaacga cggcgacgtc 2640
gtgtccacca acacctactt catgaccacc gggaacgccc tgggctccgt gaacatgacg 2700
acgggggtgg acaacctgtt ctacatcgac aagttccagg tgcgcgaggt caagtgattg 2760
attggaactc acaaagcggc ccacggcttc gaacgtcccg tgtcaattgc gcggggtgtg 2820
ccagagtttc tgcgccaccg atgctcaccc taggggggga tgccctttga cattcatgtg 2880
tgcctgcatg cacgtttgta tcagtctcac cacaccttga agattttggg agggggggg  2940
gaagtcggaa tggaaacgag ctccgcgatt gtcagatggt ggagtgggtg gatggccctg 3000
ctccgaggag ctttctaggg cgcgaacttg gcccttctcc cctctgatgc agtgtggggg 3060
gacgcggtgt gctatttctc cgagggccgc ccaactaggg tggggcgggc atacgcccgc 3120
gtcgacaggt gggtgtggcc tcgaggtgtt gagaggagtg ttatgtcgac agccaaagtg 3180
gagactgatt gaaccctact ccaggtgcta tcttgggagc acactgcgcc caccgtggct 3240
ggactgcccg aattccaacc ttggtgccca gaaacagggc aaagccggtc atcagtgcag 3300
catgagactc aagctcccta gctcatgacc gttggcatag gcagaagctg cggcagcacc 3360
tggtggaggc ctgccaggca aacggtgtca ccttccagcc gggggaggta gtggatgtgg 3420
gcgtgaagaa cggcacagcc tcggtcacct gccaagatgg ctccgtcctg actgcgaggt 3480
gggcgctgtg catggcattt gttggcacga gtctgcatct ctgaagctgc tgggtagcgt 3540
cagagcagtg gagtcaacag cacacagctc tggcggtgct cagggaacat acatcgcact 3600
gtttcctgga gttgctggcc ctctgtgggg caaccaggac cccccgacgc atgcatgccc 3660
cctcgcacat cccgcacagg ctggtgaccc tggcctccgg cgcggcggcg gggcgcttcc 3720
tcaagtacga gagaagctt                                               3739

SEQ ID NO: 2        moltype = DNA   length = 4611
FEATURE             Location/Qualifiers
misc_feature        1..4611
                    note = Nucleotide sequence of the transforming DNA from
                    pPB0038
source              1..4611
                    mol_type = other DNA
                    organism = synthetic construct
SEQUENCE: 2
aagcttcaag tgcgtgcgtt acagtgttac caacaacagt ccaacctaac cctttcggtc   60
attctgtcct ttggcaaggg ctcagaatga agtgtgcctg cacatcgagc tagtgctgtg  120
agcgaagaca aggaagtccc cactcaccca cgtggccaga ttttatcttt tttcagattg  180
```

```
caagggccac gcccagcgaa ccccgcgatg gggccgagcc atgcccgaca tctcgacatc   240
ttcatatgac aaggcgcttc aaagtgcaat ttatgtgcat ggcatcgatt aggagagtgg   300
ttgaacacca gcccatcttc caccggggaa ggaccgtcga aatgcctctg cagacggcca   360
ccgtctgatc gctgcctgtc ccgaggtgac ggcgatgtcg tccttatccc aaacaatcgt   420
tcgaagacct ttcttttgtt cgctcaaccc accgaggaga ccgtctggat tccatgccgc   480
tgtgacgcct agccccctga gaccctccaa gtgggcggtc ccctccctag ccccagcct   540
ctctgacgtg gcagatgcct ccgcggaagc aaatcaggat cgcagggagg gctcctacga   600
gcagcccctg gtccaacgcc aggtgcctag ggggaaagga gggcagggg ccttgaggcg   660
agcctggccc aggcagggct tccatggtca gtcgtgcag tgccatgaca gccgaagccc   720
accgcgacac cgtgggtgca gcatgcgtgg acggaaacat tggcaatgcc ttgcccatt   780
ggaccccag gcccggaaac gggacgatca gcaggacccc ctgtccagcc tcctccccac   840
ggtacctccc gcttttaat tgagcccctt tcgtcgctga atcagcgaaa gcaccgcgaa   900
acaatgcctg tcccgtccat gcatctcaac agcctcatgc aaggtttgca caagcaagac   960
cattctgatc tgggaacttg taggtgttgt atgggggagg ttgtgctctt gaatcaagtg  1020
gtatcacgtt tccggaacac cccgaaacgt gcatgggctt attgcgatga gagcatttcc  1080
caccgcgatt gtctcacgcg catttcggag aaggtttgca gaacactcca ggacatgaaa  1140
tgccttgtca cgtatgaacc atctcccacg gccttgaaaa gatcgctcga cttccattct  1200
agatgtgca aaaccctacg actcaagaag gtgccaccga ctcaggcatt gggcacggcg  1260
ggcagggaga agagaggagt tgatcaaaac tgctcgatca cgttcccca tggcgatccg  1320
agcagcacat gatgcatcga ggtggcgccg ttgcaaagga gttgcgcatg ggtcgaagca  1380
gggagaagga aacggcgagg cgtgccgcgg gggtgaattc agagtcaaat ctgcgcctgc  1440
cccggcgctc ctgacggggta ttaaccccca cgactgtatc catcgacact cgtctcgggg  1500
gaataaaagc ggcgacccag ctccagaggc gcaatccttc tcacaatctg tttaactttc  1560
aacaaagtat aagtcaattc aacttgcacac aatggccgcg tccgtccact gcaccctgat  1620
gtccgtggtc tgcaacaaca agaaccactc cgcccgcccc aagctgccca actcctcct  1680
gctgcccggc ttcgacgtgg tggtccaggc cgcggccacc cgcttcaaga aggagacgac  1740
gaccaccgcc gccacgctga cgttcgaccc ccccacgacc aactccgagc gcgccaagca  1800
gcgcaagcac accatcgacc cctcctcccc cgacttccag cccatccct ccttcgagga  1860
gtgcttcccc aagtccacga aggagcacaa ggaggtggtg cacgaggagt ccggccacgt  1920
cctgaaggtg cccttccgcc gcgtgcacct gtccggcgga gagcccgcct tcgacaacta  1980
cgacacgtcc ggcccccaga acgtcaacgc ccacatcggc ctggcgaagc tgcgcaagga  2040
gtggatcgac cgccgcgaga agctgggcac gccccgctac acgcagatgt actacgcgaa  2100
gcagggcatc atcacggagg agatgctgta ctgcgcgacg cgcgagaagc tggaccccga  2160
gttcgtccgc tccgaggtcg cgcggggccg cgccatcatc ccctccaaca agaagcacct  2220
ggagctggag cccatgatcg tgggccgcaa gttcctggtg aaggtgaacg cgaacatcgt  2280
caactccgcc gtggcctcct ccatcgagga ggaggtctac aaggtgcagt gggccaccat  2340
gtggggcgcc gacaccatca tggacctgtc cacgggccgc cacatccacg agacgcgcga  2400
gtggatcctg cgcaactccg cggtccccgt gggcaccgtc cccatctacc aggcgctgga  2460
gaaggtggac ggcatcgcgg agaacctgaa ctgggaggtg ttccgcgaga cgctgatcga  2520
gcaggccgag cagggcgtgg actacttcac gatccacgcg ggcgtgctgc tgcgctacat  2580
ccccctgacc gccaagcgcc tgacgggcat cgtgtcccgc ggcggctcca tccacgcgaa  2640
gtggtgcctg gcctaccaca aggagaactt cgcctacgag cactgggacg acatcctgga  2700
catctgcaac cagtacgacg tcgccctgtc catcggcgac ggcctgcgcc tggctccaa  2760
ctacgacgcc aacgacacgg cccagttcgc cgagctgctg acccagggcg agctgacgcg  2820
ccgcgcgtgg gagaaggacg tgcaggtgat gaacgagggc cccggccacg tgcccatgca  2880
caagatcccc gagaacatgc agaagcagct ggagtggtgc aacgaggcgc ccttctacac  2940
cctgggcccc ctgacgaccg acatcgcgcc cggctacgac cacatcacct ccgccatcgg  3000
cgcggccaac atcggcgcgcc tgggcaccgc cctgctgtgc tacgtgacgc ccaaggagca  3060
cctgggcctg cccaaccgcg acgacgtgaa ggcgggcgtc atcgcctaca agatcgccgc  3120
ccacgcggcc gacctggcca agcagcaccc ccacgcccag gcgtgggacg acgcgctgtc  3180
caaggcgcgc ttcgagttcc gctgatgga ccagttcgcg ctgtccctgg accccatgac  3240
ggcgatgtcc ttccacgacg agacgctgcc cgcggacggc gcgaaggtcg cccacttctg  3300
ctccatgtgc ggccccaagt tctgctccat gaagatcacg gaggacatcc gcaagtacgc  3360
cgaggagaac ggctacggct ccgccgagga ggccatccgc cagggcatgg acgccatgtc  3420
cgaggagttc aacatcgcca agaagacgat ctccggcgag cagcacggcg aggtcggcgg  3480
cgagatctac ctgcccgagt cctacgtcaa ggccgcgcag aagtgagtcc tggcgaccct  3540
gctccctgac cccctgttcc cctgcgctgc ttctcccgg tgacatccga cctgctgcaa  3600
aattcccgtt cctgcacaac acttgcctga ccgagggtcg ggtcgcgaag taaaagccac  3660
aatcaacacc ccaggcacat taagagtgca cagcatgacg cagcataggg tttgtgtcgg  3720
aggaaggggg tcgagtcgcg ttggcgaggg ggtggtcacg atgaccacat ctgcgggata  3780
attgaatcct caggggaaaa taccagtctc tgcttccagg tgctccggag ctccgcgatt  3840
gtcagatggt ggagtgggtg gatggcccctg ctccagagga gcgttctagg gcgcaaactt  3900
ggcactttcc cccctctgat gcagtgtggg gggacgcggt gtgctatttc tccgagggcc  3960
gcccaaccag ggtggggcgg gcatatgccc gcgtcgacag gtgggtgtgg ccctcgaggtg  4020
ttgagaggag ggttatgtcg acagccaaag tggagactga gtgaaccta ctccaggtgc  4080
tgtcgtggga gcgcactgcg cccaccgtgg ctggactgct cgtattccaa ccttggtgcc  4140
cagaaacagg gcaaagccgg tcatcagtgc agcatgagac tcaagctccc taactcatga  4200
ccgttggcat aggcagaagc tgcggcagca cctggtggag gcctgccagg caaacggtgt  4260
caccttccag ccgggggaag tagtggatgt gggcgtgaag aacggcacag cctcggtcac  4320
ctgccgagac ggctccgtcc tgactgcgag gtgggcgctg tgcatggcac ttgttggcac  4380
gagtctgcat ccctcgaagct gctgggtagc gtcagacag tggcgtcaac agcacacagc  4440
tctggcggtg cccagggaac atacatcgct ctgtttcctg gagttgcggg ccctctgtgt  4500
ggcagccagg gccccccgac gcatgcatgc ctcctcgcac atcccgcaca ggctggtgac  4560
cctggcctcc ggcgcggcgg cggggcgctt cctcaagtac gagagaagct t          4611
```

```
SEQ ID NO: 3            moltype = DNA  length = 2081
FEATURE                 Location/Qualifiers
misc_feature            1..2081
                        note = Nucleotide sequence of the CrBKT1 expression module
```

```
                             from pPB0120
source                       1..2081
                             mol_type = other DNA
                             organism = synthetic construct
SEQUENCE: 3
ggtaccttg cagtgcccca aaaactggct accacctaac aattctcacg cagtttttatc   60
ctctgcactt tgatgtcagc tttttgattc gtctgcgtac attacagcgt tgagtggcca  120
gcaggaagga gaccgcggtc cgagacgagt ctgagggcgc gctctcgcaa cttggattcc  180
ggatttctta ccctgcatcg acctcggcct ggagtcgatc agaaattgtc attgccagat  240
tgcctggcga ggacgggtga tatactcaag gcgttgcatc gcccacaaaa cacacactta  300
tctgcaaggg agttactgca tcaggctctg ctcaacagct cgtgacatcg atcgttcagc  360
tccccagcag gtgcgtgtcc gcatggagca cccctcccga gacacctgcg ttgggtgtcg  420
gaggagctca catgccaggg aggtgcccac attgcaccac gcgaccgcga aataggcaga  480
cttcgggcat cctgtcatcg catgtccgct ggccgggaat catggcctcc ccaccaggcg  540
tcacgcgctg cccacctccc tcccccttgct gcgcagggca ccgcgttcct gtggagagcc  600
gaccacatgg gccccggcat ccagcccacc tccgcccgcc cctgctcccg caccaagcac  660
tcccgcttcg ccctgctggc cgccgccctg accgcccgcc gcgtgaagca gttcaccaag  720
cagttccgct cccgcccgcat ggccgaggac atcctgaagc tgtggcagcg ccagtaccac  780
ctgcccccgcg aggactccga caagcgcacc ctgcgcgagc gcgtgcacct gtaccgcccc  840
ccccgctccg acctgggcgg catcgccgtg gccgtgaccg tgatcgccct gtgggccacc  900
ctgttcgtgt acggcctgtg gttcgtgaag ctgcctgggg ccctgaaggt gggcgagacc  960
gccacctcct gggccaccat cgccgccgtg ttcttctccc tggagttcct gtacaccggc 1020
ctgttcatca ccacccacga cgccatgcac ggcaccatcg ccctgcgcaa ccgccgcctg 1080
aacgacttcc tgggccagct cgcgatctcc ctgtacgcct ggttcgacta ctccgtgctg 1140
caccgcaagc actgggagca ccacaaccac accggcgagc ccgcgtgga ccccgacttc 1200
caccgcggca accccaacct ggccgtgtgg ttcgcccagt tcatggtgtc ctacatgacc 1260
ctgtcccagt tcctgaagat cgccgtgtgg tccaacctgc tgctgctggc cggcgccccc 1320
ctggccaacc agctgctgtt catgaccgcc gcccccatcc tgtccgcctt ccgcctgttc 1380
tactacggca cctacgtgcc ccaccacccc gagaagggcc acaccggcgc catgcccctgg 1440
caggtgtccc gcacctcctc cgcctcccgc ctgcagtcct tcctgacctg ctaccacttc 1500
gacctccact gggagcacca ccgctggccc tacgcccct ggtgggagct gcccaagtgc 1560
cgccagatcg cccgcggcgc cgccctggcc tgagcggagg ccttggaaat attcgcgtca 1620
cgcgaggagt aggctctgct ggtcggccct ggatacgctg actcttcaag cagtggggca 1680
ccacacccac cttttgccaa gggcaaggag tcggaagggg gcgggggctgc cgtgcacccc 1740
tgacgggcat ggccgttccg cgagggcgcc aactgcggcg gcctgcccgc tggctcgtgc 1800
ccccctaccc ccaccattgc ctggagcgtt tccatcccca aatcacattc catccaagtt 1860
gtatcactat gccccctttgg ctctatacac tcacggcctg aggtccttc tcggccgtgg 1920
cggcacacgc ccaaccccc accatactct ttccatacac tgcaatgctt cgagcctgcc 1980
tgccacctgc tctgcttgtc tcccctccct tcccttgagg ttttccaatg cagtaagaga 2040
agtcgacgtg catggacaga tgattgagag atgagactag t                       2081

SEQ ID NO: 4                 moltype = DNA   length = 981
FEATURE                      Location/Qualifiers
misc_feature                 1..981
                             note = Nucleotide sequence of the ApSAD2tp_CrBKT1
                              expression module from pPB0123
source                       1..981
                             mol_type = other DNA
                             organism = synthetic construct
SEQUENCE: 4
atggccaccg catccacttt ctcggcgttc aatgcccgct gcggcgacct gcgtcgctcg   60
gcgggctccg ggcccccggcg cccagcgagg cccctccccg tgcgcgctgc catccgctcc  120
cgccgcatgg ccgaggacat cctgaagctg tggcagcgcc agtaccacct gccccgcgag  180
gactccgaca agcgcaccct gcgcgagcgc gtgcacctgt accgcccccc ccgctccgac  240
ctgggcggca tcgccgtggc cgtgaccgtg atcgccctgt gggccaccct gttcgtgtac  300
ggcctgtggt tcgtgaagct gcccctgggg cctgaaggtgg gcgagaccgc cacctcctgg  360
gccaccatcg ccgccgtgtt cttctccctg gagttcctgt acaccggcct gttcatcacc  420
acccacgacg ccatgcacgg caccatcgcc ctgcgcaacc gccgcctgaa cgacttcctg  480
ggccagctcg cgatctccct gtacgcctgg ttcgactact ccgtgctgca ccgcaagcac  540
tgggagcacc acaaccacac cggcgagccc gcgtggacc cgacttcca ccgcggcaac  600
cccaacctgg ccgtgtggtt cgcccagttc atggtgtcct acatgaccct gtcccagttc  660
ctgaagatcg ccgtgtggtc caacctgctg ctgctggccg gcgcccccct ggccaaccag  720
ctgctgttca tgaccgccgc ccccatcctg tccgccttcc gcctgttcta ctacggcacc  780
tacgtgcccc accaccccga gaagggccac accggcgcca tgcccctggc agctcctccg  840
acctcctccg cctcccgcct gcagtccttc ctgacctgct accacttcga cctccactgg  900
gagcaccacc gctggcccta cgcccctgg tgggagctgc caagtgccg ccagatcgcc  960
cgcggcgccg ccctggcctg a                                             981

SEQ ID NO: 5                 moltype = AA   length = 328
FEATURE                      Location/Qualifiers
REGION                       1..328
                             note = Amino acid sequence of native CrBKT1
source                       1..328
                             mol_type = protein
                             organism = synthetic construct
SEQUENCE: 5
MGPGIQPTSA RPCSRTKHSR FALLAAALTA RRVKQFTKQF RSRRMAEDIL KLWQRQYHLP   60
REDSDKRTLR ERVHLYRPPR SDLGGIAVAV TVIALWATLF VYGLWFVKLP WALKVGETAT  120
SWATIAAVFF SLEFLYTGLF ITTHDAMHGT IALRNRRLND FLGQLAISLY AWFDYSVLHR  180
```

```
KHWEHHNHTG EPRVDPDFHR GNPNLAVWFA QFMVSYMTLS QFLKIAVWSN LLLLAGAPLA   240
NQLLFMTAAP ILSAFRLFYY GTYVPHHPEK GHTGAMPWQV SRTSSASRLQ SFLTCYHFDL   300
HWEHHRWPYA PWWELPKCRQ IARGAALA                                      328
```

```
SEQ ID NO: 6              moltype = AA   length = 326
FEATURE                   Location/Qualifiers
REGION                    1..326
                          note = Amino acid sequence of chimeric ApSAD2tp_CrBKT1
source                    1..326
                          mol_type = protein
                          organism = synthetic construct
SEQUENCE: 6
MATASTFSAF NARCGDLRRS AGSGPRRPAR PLPVRAAIRS RRMAEDILKL WQRQYHLPRE   60
DSDKRTLRER VHLYRPPRSD LGGIAVAVTV IALWATLFVY GLWFVKLPWA LKVGETATSW   120
ATIAAVFFSL EFLYTGLFIT THDAMHGTIA LRNRRLNDFL GQLAISLYAW FDYSVLHRKH   180
WEHHNHTGEP RVDPDFHRGN PNLAVWFAQF MVSYMTLSQF LKIAVWSNLL LLAGAPLANQ   240
LLFMTAAPIL SAFRLFYYGT YVPHHPEKGH TGAMPWQVSR TSSASRLQSF LTCYHFDLHW   300
EHHRWPYAPW WELPKCRQIA RGAALA                                        326
```

```
SEQ ID NO: 7              moltype = DNA   length = 4637
FEATURE                   Location/Qualifiers
misc_feature              1..4637
                          note = Nucleotide sequence of the transforming DNA from
                          pPB0065
source                    1..4637
                          mol_type = other DNA
                          organism = synthetic construct
SEQUENCE: 7
aagctttcac tgctccattc acacccaatt tcccaccgcc gcacccgctc ccaggtggga   60
ggatgggagg gaacccagct gggagccgga ggagcatgtg accccggacc tgatcgagct   120
atatgccgcc agggacgctc gagcacggga tgtcaaggcc gcggctgaca aggctggcaa   180
gggtaggaca cctgcgttga ggcaaacgct ggagacggcc ggtctcagca tgtgatcctg   240
tacttgctgt gacaaggtgg acaatgcagt acgaggtgta ccaggctaag tattcctagt   300
ataccggcac gccagatcat ctgtacagga gtctgtgcag gagtgaaaag gtaagagcca   360
gagccatgac cggcgaccat ccatgtcccg tcactcggat gcactggctg acatcggcgg   420
caggtcatcc aacggtcctg aatgatcgag aggaagctgc ccgatttcaa aacgcccccc   480
cacgtcgccc tccatggccg cacagcatgc tcagcacagg ttgctgcgtg tcctcacaca   540
aactgctcct ttaaagcgat caactttcca gggcatgggg cactcgtact gacaatcacc   600
cacattcgta taccttgac gtcattattt tttcgcccca acgcggttgc catcccgagt   660
tgtacctccg cggctaccat accctgtct tctggccctc accgtcgctc gcaggcggga   720
tccagcgcag ccagtctgaa tactttaca caacatagta cgtaacgcgc attaggcccc   780
caataccagc agctggctcc agcatgggca agggtcgcgc gcaggaggaa ttctcccgct   840
ttttaattga gcccctttcg tcgctgaatc agcgaaagca ccgcgaaaca atgcctgtcc   900
cgtccatgca tctcaacagc ctcatgcaag gtttgcacaa gcaagaccat tctgatctgg   960
gaacttgtag gtgttgtatg ggggaggttg tgctcttgaa tcaagtggta tcacgtttcc   1020
ggaacacccc gaaacgtgca tgggcttatt gcgatgagag catttcccac cgcgattgtc   1080
tcacgcgcat ttcggagaag gtttgcagaa cactccagga catgaaatgc cttgtcacgt   1140
atgaaccatc tcccacggcc ttgaaaagat cgctcgactt ccattctaga tggtgcaaaa   1200
ccctacgact caagaaggtg ccaccgactc aggcattggg cacggcgggc agggagaaga   1260
gaggagttga tcaaaactgc tcgatcacgt tcccccatgg cgatccgagc agcacatgat   1320
gcatcgaggt ggcgccgttg caaaggagtt gcgcatgggt cgaagcaggg agaaggaaac   1380
ggcgaggcgt gccgcggggg tgaattcaga gtcaaatctg cgcctgcccc ggcgctcctg   1440
acggggatta accccacga ctgtatccat cgacactcgt ctcgggggaa taaaagcggc   1500
gacccagctc cagaggcgca atccttctca caatctgttt aactttcaac aaagtataag   1560
tcaattcaac ttgacacaat ggccgcgtcc gtccactgca ccctgatgtc cgtggtctgc   1620
aacaacaaga accactccgc ccgcccaag ctgcccaact cctccctgct gcccggcttc   1680
gacgtggtgg tccaggccgc ggccacccgc ttcaagaagg agacgacgac cacccgcgcc   1740
acgctgacgt cgacccccc cacgaccaac tccgagcgcg ccaagcagcg caagcacacc   1800
atcgacccct cctccccga cttccagccc atcccctcct tcgaggagtg cttccccaag   1860
tccacgaagg agcacaagga ggtggtgcac gaggagtccg gccacgtcct gaaggtgccc   1920
ttccgccgcg tgcacctgtc cggcggcgag cccgccttcg acaactacga cacgtccggc   1980
ccccagaacg tcaacgccca catcggcctg gcgaagctgc gcaaggagtg gatcgaccgc   2040
cgcgagaagc tgggcacgcc ccgctacacg cagatgtact acgcgaagca gggcatcatc   2100
acggaggaga tgctgtactg cgcgacgcgc gagaagctgg acccgagtt cgtccgctcc   2160
gaggtcgcgc ggggccgcgc catcatcccc tccaacaaga gcacctgga gctggagccc   2220
atgatcgtgg gccgcaagtt cctggtgaag gtgaacgcga acatcggcaa ctccgccgtg   2280
gcctcctcca tcgaggagga ggtctacaag gtgcagtggg gccaccatgt ggggcgccgac   2340
accatcatgg acctgtccac gggccgccac atccacgaga cgcgcgagtg gatcctgcgc   2400
aactccggac tccccgtggg caccgtcccc atctaccagg cgctggagaa ggtggacggc   2460
atcgcggaga acctgaactg ggaggtgttc cgcgagacgc tgatcgagca ggccgagcag   2520
ggcgtggact acttcacgat ccacgcgggc gtgctgctgc gctacatccc cctgaccgcc   2580
aagcgcctga cgggcatcgt gtcccgcggc ggctccatcc acgcgaagtg gtgcctggcc   2640
taccacaagg agaacttcgc ctacgagcac tgggacgaca tcctggacat ctgcaaccag   2700
tacgacgtgc ccctgtccat cggcgacggc ctgcgcccca tcctccatcta ctgcgccaac   2760
gacacggccc agttcgccga gctgctgacc cagggccagc tgacgcgccg cgcgtgggag   2820
aaggacgtgc aggtgatgaa cgagggcccc ggccacgtgc ccatgcacaa gatccccgag   2880
aacatgcaga agcagctgga gtggtgcaac gaggcgccct ctacaccct gggccccctg   2940
acgaccgaca tcgcgcccgg ctacgaccac atcacctccg ccatcggcgc ggccaacatc   3000
ggcgccctgg gcaccgccct gctgtgctac gtgacgcgcca aggagcacct gggcctgccc   3060
```

-continued

```
aaccgcgacg acgtgaaggc gggcgtcatc gcctacaaga tcgccgccca cgcggccgac 3120
ctggccaagc agcaccccca cgcccaggcg tgggacgacg cgctgtccaa ggcgcgcttc 3180
gagttccgct ggatggacca gttcgcgctg tccctggacc ccatgacggc gatgtccttc 3240
cacgacgaga cgctgcccgc ggacggcgcg aaggtcgccc acttctgctc catgtgcggc 3300
cccaagttct gctccatgaa gatcacggag gacatccgca agtacgccga ggagaacggc 3360
tacggctccg ccgaggaggc catccgccag ggcatggacg ccatgtccga ggagttcaac 3420
atcgccaaga agacgatctc cggcgagcag cacggcgagg tcggcggcga gatctacctg 3480
cccgagtcct acgtcaaggc cgcgcagaag tgagtcctgg cgaccctgct ccctgaccc 3540
ctgttcccct gcgctgcttc tccccggtga catccgacct gctgcaaaat tcccgttcct 3600
gcacaacact tgcctgaccg agggtcgggt cgcgaagtaa aagccacaat caacacccca 3660
ggcacattaa gagtgcacag catgacgcag cataggggttt gtgtcggagg aagggggtcg 3720
agtcgcgttg gcgagggggt ggtcacgatg accacatctg cgggataatt gaatcctcag 3780
gggaaaatac cagtctctgc ttccaggtgc tccggagctc cccaggcgag tcaatcagtt 3840
gtgtcatgag attgatctgc ctgttgcaga tcccccgacc cgctgccggc ccctctgccg 3900
tgcgacaccc cttgccctgg ggtgtgcctc ttgtcctgca tcgcacacct cctccgccgg 3960
accttcaccc cctcccacct cgacacaagc aggtgtggga cgtgatagtg gtgggcgcgg 4020
gcgtggccgg cgcggcgctg gcgcatcagc agggcttgga cggccgacgc gtgctgctcc 4080
tcgagcggga tctggcccag cccgaccgca tcgtgggcga gctgctgcag cctggcgggg 4140
tgctggccct ggagcgcctg ggcctggggcg cgcgccgtgga cggcatcgac gcgcagcccg 4200
tggtcgggta ctgcatgttc aagggcgggc gcgaggcgtg catcgcctac cccacccccg 4260
ccgagctggg gggtccagcg gctgcggctg cggcatgcag gggccccact ggaagcgcca 4320
gcgccgcgcc cgccggcgac gcccccgtca cgggcttctc cttccacaac gggcgattcg 4380
tgcagcggct gcgcgccgcg cggcggcgctg cgcccggggt cacgcgcgt cgcggcacgg 4440
tgcgcgcgct ggtggatgac gccggcgcgg actgggagga ggggcgcgtg gtgacgggcg 4500
tgcggtaccg cgcgggcgac ggcggcgagc gcgtggcact gggccacctc accgtggtct 4560
gcgacggcat gtactcggcc ctgcggtcca agctggcggt gcccgacctg cgcacgccct 4620
cccacttcat caagctt                                                  4637
```

```
SEQ ID NO: 8              moltype = DNA   length = 3767
FEATURE                   Location/Qualifiers
misc_feature             1..3767
                          note = Nucleotide sequence of the transforming DNA from
                            pPB0077
source                   1..3767
                          mol_type = other DNA
                          organism = synthetic construct
SEQUENCE: 8
aagctttcac tgctccattc acacccaatt tcccaccgcc gcacccgctc ccaggtggga 60
ggatgggagg gaacccagct gggagccaga ggagcatgtg accccggacc tgatcaagct 120
atatgccgcc agggacgctc gagcacggga tgtcaaggcc gcggctgaca aggctggcaa 180
gggcaggaca cctgcgccga ggcaaacgct ggagacggcc ggtctcagca tgtgatcctg 240
tacttgctgt gacaaggtgg acaatgcagt acgagttgta ccaggctaag tatccctagt 300
ataccggcac gccagatcat ctgtacagga gtctgtgcag gagtaaaaag gcaacagcca 360
gagccatgac cggcgactat ccacatcccg tcactccgat gcactggctg acatcggcgg 420
caggtcgtcc aacggtcctg aatgatcgag aggaagctgc ccgatttcac cccccccccc 480
cacgtcgccc tccatggccg cacagcatgc tcagcacagg ttgctgcgtg tcctcacaca 540
aactgctcct ttaaagcgat caactttcca gggcatgggg cactcgtact gacaatcacc 600
cacattcgta taccctttgac gtcattttttt tttcgcccca acgcggttgc catcccgagt 660
tgtacctccg cggctaccat accctgtct tctggccctc accgtcgctc gcaggcggga 720
tccagcgcag ccagtctgaa tactttaca caacatagta cgtaacgcgc attaggcccc 780
caataccagc agctggctcc agcatgggca agggtgcgcg gcaggaggaa ttcctttctt 840
gcgctatgac acttccagca aaaggtaggg cgggctgcga gacggcttcc cggcgctgca 900
tgcaacaccg atgatgcttc gacccccccga agctccttcg gggctgcatg ggcgctccga 960
tgccgctcca gggcgagcgc tgtttaaata gccaggcccc cgattgcaaa gacattatag 1020
cgagctacca aagccatatt caaacaccta gatcactacc acttctacac aggccactcg 1080
agcttgtgat cgcactccgc taagggggcg cctcttcctc ttcgtttcag tcacaacccg 1140
caaacatgct gctgcaggcc ttcctgttcc tgctggccgg cttcgccgcc aagatcagcg 1200
cctccatgac gaacgagacg tccgaccgcc ccctggtgca cttcacccccc aacaagggct 1260
ggatgaacga ccccaacggc ctgtggtacg acgagaagga cgccaagtgg cacctgtact 1320
tccagtacaa cccgaacgac accgtctggg ggacgccctt gttctggggc cacgccacgt 1380
ccgacgacct gaccaactgg gaggaccagc ccatcgccat cgccccgaag cgcaacgact 1440
ccggcgcctt ctccggctcc atggtggtgg actacaacaa cacctccggc ttcttcaacg 1500
acaccatcga cccgcgccag cgctgcgtgg ccatctggac ctacaacacc ccggagtccg 1560
aggagcagta catctcctac agcctggacg gcggctacac cttcaccgag taccagaaga 1620
accccgtgct ggccgccaac tccacccagt tccgcgaccc gaaggtcttc tggtacgagc 1680
cctcccagaa gtggatcatg accgcggcca agtcccagga ctacaagatc gagatctact 1740
cctccgacga cctgaagtcc tggaagctgg agtccgcgtt cgccaacgag ggcttcctcg 1800
gctaccagta cgagtgcccc ggcctgatcg aggtccccac cgagcaggac cccagcaagt 1860
cctactgggt gatgttcatc tccatcaacc ccggccgccc ggccggcggc tccttcaacc 1920
agtacttcgt cggcagcttc aacggcaccc acttcgaggc cttcgacaac cagtcccgcg 1980
tggtggactt cggcaaggac tactacgccc tgcagacctt cttcaacacc gacccgacct 2040
acgggagcgc cctgggcatc gcgtgggcct ccaactggga gtactccgcc ttcgtgccca 2100
ccaaccctg gcgctcctcc atgtccctcg tgcgcaagt ctccctcaac accgagtacc 2160
aggccaaccc ggagacggag ctgatcaacc tgaaggccga gatcctg aacatcagca 2220
acgccggcc ctggagccgg ttcgccacca acaccacgtt gacgaaggcc aacagctaca 2280
acgtcgacct gtccaacagc accggcaccc tggagttcga gctggtgtac gccgtcaaca 2340
ccacccagac gatctccaag tccgtgttcg cggacctctc cctctggttc aagggcctgg 2400
aggaccccga ggagtacctc cgcatggggct tcgaggtgtc cgcgtcctcc ttcttcctgg 2460
accgcgggaa cagcaaggtg aagttcgtga aggagaaccc ctacttcacc aaccgcatga 2520
```

```
gcgtgaacaa ccagcccttc aagagcgaga acgacctgtc ctactacaag gtgtacggct  2580
tgctggacca gaacatcctg gagctgtact tcaacgacgg cgacgtcgtg tccaccaaca  2640
cctacttcat gaccaccggg aacgccctgg gctccgtgaa catgacgacg ggggtggaca  2700
acctgttcta catcgacaag ttccaggtgc gcgaggtcaa gtgattgatt ggaactcaca  2760
aagcggccca cggcttcgaa cgtcccgtgt caattgcgac gggtgtgcca gagtttctgc  2820
gccaccgatg ctcaccctag gggggatgc cctttgacat tcatgtgtgc ctgcatgcac  2880
gtttgtatca gtctcaccac accttgaaga tttttgggag ggggggggaa gtcggaatgg  2940
aaacgagctc cccaggcgag tcaatcagtt gtgtcatgag attgatctgc ctgttgcaga  3000
tcccccgacc cgctgccggc ccctctgccg tgcgacaccc cttgccctgg ggtgtgcacc  3060
ttgtcctgca tcgcacacct cctccgccgg accttcaccc cctcccacct cgacacaagc  3120
aggtgtggga cgtgatagtg gtgggcgcgg gcgtggccgg cgcggcgctg gcgcatcagc  3180
agggcttgga cggccgacgc gtgctgctcc tcgagcggga tctggcccag cccgaccgca  3240
tcgtgggcga gctgctgcag cctggcggcg tgctggccct ggagcgcctg ggcctgggcg  3300
gcgccgtgga cggcatcgac gcgcagcccg tggtcgggta ctgcatgttc aagggcgtgg  3360
gcgaggcgtg catcgcctac cccacccccg ccgagctcgg gggtccagcg gctgcggctg  3420
cggcatgcag gggccccact ggaagcgcca gcgccgcgcc cgccggcgac gccccgtca  3480
cgggcttctc cttccacaac gggcgattcg tgcagcggct gcgcgccgcg gcggcggctg  3540
cgcccggggt cacgctgcgt cgcggcacgg tgcgcgcgct ggtggatgac gccgcgcgag  3600
actgggagga ggggcgcgtg gtgacgggcg tgcggtaccg cgccggcgac ggcggcgagc  3660
gcgtggcact gggccacctc accgtggtct gcgacggcat gtactcggcc ctgcggtcca  3720
agctggcggt gcccgacctg cgcacgccct cccacttcat caagctt               3767
```

SEQ ID NO: 9                 moltype = AA  length = 730
FEATURE                      Location/Qualifiers
REGION                       1..730
                             note = Amino acid sequence of A. prototthecoides
                             1-deoxy-D-xylulose 5-phosphate synthase (DXS)
source                       1..730
                             mol_type = protein
                             organism = synthetic construct
SEQUENCE: 9
```
MQFSLAGMNT RALQTGARPS LPAARPSRRV RPARRSAPCP VARTMGGGEE QPSSAEGVAW  60
DKISTDELAD WAGAGPPTPL LDTVAFPVHI KNFNSRQLQQ LCKELRADLI HTVAKTGGHL  120
GSSLGVVELT VALHHVFNTP EDRIVWDVGH QAYIHKMLTG RRARMHTIRQ QGGLSGFTRR  180
AESVYDPFGA GHSSTSVSAA LGMAVGRDRK GRANNCIAVI GDGAITGGMA YEAMNHAGFL  240
DTNMIVILND NQQVSLPTQY NGKNQEPVGA LSSALARLQA NRQLRELREI AKGVTKQLPD  300
VIQNATAKID EYARGMISGT GSTLFEELGF YYIGPVDGHN MQDLVDVLSE IKATETVGPV  360
LLHVVTQKGR GYTPAETASD RMHGVVQYDT LTGKQKKGSG GPQSYTNYFA DALVAEAKRD  420
ARVLGIHAAM GGGTGMNRFE AAFPDRVFDT GIAEQHAVTF AAGLATEGLV PFVAIYSTFL  480
QRGYDQIVHD VSLQSLPVRF ALDRAGNVGA DGATHAGAFD VTYLACLPNM VVMAPSNEAE  540
LVHAVATAAA IDDRPSAFRF PRGNGLGVDL AAAGVTDDLK GQPMEVGRGV VRRGGADVAL  600
LGYGTCVNAC LAAADLLAAQ GVSATVVDAR FCKPLDTALV RRMAAEHPVM ITVEEGSIGG  660
FAAHVMQFLA LEGLLDGKLK FRPMTLPDRY IEHGTQAEQM AEAGLTASHI AGTALSVMGV  720
KRDAPSIFST                                                         730
```

SEQ ID NO: 10                moltype = AA  length = 453
FEATURE                      Location/Qualifiers
REGION                       1..453
                             note = Amino acid sequence of A. prototthecoides
                             1-deoxy-D-xylulose 5-phosphate reductoisomerase (DXR)
source                       1..453
                             mol_type = protein
                             organism = synthetic construct
SEQUENCE: 10
```
MRCSAQLNTR GPTLPNSARP RTCRVVSASA APVPSAWPGR VVLPEKSASR TGPKKFSLLG  60
STGSIGTQTL DIVAEHPDRF QVVSLAAGGN VALLAEQIAR FSPSLVSVRD SGGARALEAA  120
LDAAGVDRRP EIQIGAAGID AVAAHPEADA CVTGIVGCAG LRPTMAAIEA GKDICLANKE  180
TLIAGGPTVL PAAAKHGVSI LPADSEHSAI FQCLQGLPEG GLRRIILTAS GGAFRDLPVS  240
ELPKVTVADA LKHPNWAMGK KITIDSATLM NKGLEVIEAH YLFGASYDNI DIVIHPQSIV  300
HSMIETQDSS VLAQLGWPDM RLPILYTMSW PERVPCSEVT WPRLDFVKAG NLTFRQPDHA  360
KYPAMELAYS AGRAGGTMTG VMSAANEAAV ELFLEEAIGY LDIVPVVEAA CEAHRVELVE  420
RPSLEEIVHY DQWARRHVRE SVAKRAPAAV PAL                                453
```

SEQ ID NO: 11                moltype = AA  length = 359
FEATURE                      Location/Qualifiers
REGION                       1..359
                             note = Amino acid sequence of A. prototthecoides farnesyl
                             diphosphate synthase (FDPS)
source                       1..359
                             mol_type = protein
                             organism = synthetic construct
SEQUENCE: 11
```
MAAVVEAGHA ASKQKTEAHQ TKQEFLAVFE KLRDELLEDS ILAGQPESSK DWLRTMLDYN  60
VPHGKLNRGM AVLDVLLAAR GGDVTEKERE AANVLGWCIE LLQAYFLVAD DIMDSSLTRR  120
GQPCWYRQPH VGMVAINDGI ILESCIYRLL KLHFRAHPAY VHLLELFHDT THRTAHGQLL  180
DTTTAPPGGV DLTRYTEGTY LRIVTYKTAF YTIYLPVACG LALAGVTDEA SLALAEDLSV  240
RMGRYFQIQD DVLDAFGEPE VIGKVGTDIQ DSKCSWLVVR ALAVASAEQR EAIKANYGRD  300
DAEAVEAVKA VYRELDLPAA FAAYEQESYD GLVQAIEGQD KFPPAVFMGI LAKIYKRTK   359
```

```
SEQ ID NO: 12         moltype = AA   length = 458
FEATURE               Location/Qualifiers
REGION                1..458
                      note = Amino acid sequence of A. protothecoides squalene
                      synthase (SQS)
source                1..458
                      mol_type = protein
                      organism = synthetic construct
SEQUENCE: 12
MGKLGELLSH PDEIIPMAAM YLAARRAAVL PHDPDLAFCY SMLNKVSRSF AIVIQQLPEQ   60
LRDAVCVFYL VLRALDTVED DMAIDQAEKV PILLSFHEKT YEKDWSMKCG HGHYVELMEQ  120
YPVVCAAFQG LEPQYQEVIT DICRRMGAGM AEFIVKEVET VKDYDLYCHY VAGLVGVGLS  180
NLFAGSGLES EDFASLHELS NGMGLFLQKT NIIRDYLEDI MEEPAPRMFW PKEIWGKHGD  240
SLEDFKDPEN AEAAVACLND MIADALRHVD ASLDYMQRLR NRPIFRFCAV PQIMAIGTLA  300
ACFDNPSVFT GVVKMRRGQT AKIMHDVEDY ADLLAYFRAF GQALAAKARA ARGKGAESVG  360
RAAERVVAGC SAALADLSRA ENARMAAAAR RPLSLPARAL LLVAALLYLF LAWRAEGVRR  420
WLGVDSPPAA HKLDYYNQIV ASMFLGYSLF AVGTGRRP                         458

SEQ ID NO: 13         moltype = DNA   length = 5161
FEATURE               Location/Qualifiers
misc_feature          1..5161
                      note = Nucleotide sequence of the transforming DNA from
                      pPB0039
source                1..5161
                      mol_type = other DNA
                      organism = synthetic construct
SEQUENCE: 13
aagcttgcac agtcagtcgt catccacgaa gtcgcgcccg tctgtccacc ggggtctcct   60
gaacgcagca atctcctcct gagtgtatga gcccgtggcc gggagtttgt atgcagggcg  120
aggcaaggac gaccatgccg ggagaaaccc aaggtgacga agtgacattg tgctcgatca  180
ctccatgcac tgcctcactc gcccatgtac cttggtcatg tactccccag tctgcatctt  240
ggtgttcctg ttcagctcgc ggagctcctc caggcgctgc tcgtcgcggc ggtcccgcga  300
gatgtaaaag gcagggacac ccaccccag ggccactccc agtagagccc ccctacagc    360
aaccagggtg tccggatcgc taaagtcgat gttgatcgcg cggcacggtg gcattatcgg  420
gcgtggatgg ccccatgatc ggtgcaacga aggcgccctc atggcaggtc cgcatggtcg  480
tccattgcag gggataccg ctcgcacttt cgttgacaat aacatcctcg tatagttgga   540
gaaaggattt gtgatctgtc tctggaggcc cttaaagtcc tgccctcct ctgctggaac   600
ctgacctctc atgccctgc gccacgcccc cggatctgat atggctctga tatgggtggc   660
tcgtacctct tggctaggcg accccctaa gcacgcgtgc gggccagggc acaacattat    720
attttgccct ctccttcgtc aacgctcatt tttttggaat actaacgttt aaaagctctc  780
gggtacctcc cgctttttaa ttgagcccct ttcgtcgctg aatcagcgaa agcaccgcga  840
aacaatgcct gtcccgtcca tgcatctcaa cagcctcatg caaggtttgc acaagcaaga  900
ccattctgat ctgggaactt gtaggtgttg tatgggggag gttgtgctct tgaatcaagt  960
ggtatcacgt ttccggaaca ccccgaaacg tgcatgggct tattgcgatg agagcatttc 1020
ccaccgcgat tgtctcacgc gcatttcgga gaaggtttgc agaacactcc aggacatgaa 1080
atgccttgtc acgtatgaac catctcccac ggccttgaaa agatcgctcg acttccattc 1140
tagatggtac aaaaccctac gactcaagaa ggtgccaccg actcaggcat tgggcacggc 1200
gggcagggag aagagaggag ttgatcaaaa ctgctcgatc acgttccccc atggcgatcc 1260
gagcagcaca tgatgcatcg aggtggcgcc gttgcaaagg agttgcgcat gggtcgaagc 1320
agggagaagg aaacgcgag gcgtgccgcg ggggtgaatt cagagtcaaa tctgcgcctg  1380
ccccgggct cctgacgggg attaacccce acgactgtat ccatcgacac tcgtctcggg   1440
ggaataaaag cggcgaccca gctccagagg cgcaatcctt ctcacaatct gtttaacttt 1500
caacaaagta taagtcaatt caacttgaca caatggccgc gtccgtccac tgcaccctga 1560
tgtccgtggt ctgcaacaac aagaaccact ccgcccgccc caagctgccc aactcctccc 1620
tgctgcccgg cttcgacgtg gtggtccagg ccgcggccac ccgcttcaag aaggagacga 1680
cgaccacccg cgccacgctg acgttcgacc cccccacgac caactccgag cgcgccaagc 1740
agcgcaagca caccatcgac ccctcctccc ccgacttcca gcccatcccc tccttcgagg 1800
agtgcttccc caagtccacg aaggagcaca aggaggtggt gcacgaggag tccggccacg 1860
tcctgaaggt gcccttccgc cgcgtgcacc tgtccggcgg cgagcccgac ttcgacaact 1920
acgacacgtc cggcccccag aacgtcaacg cccacatcgg cctggcgaag ctgcgcaagg 1980
agtggatcga ccgccgcgag aagctgggca cgccccgcta cacgcagatg tactacgcga 2040
agcagggcat catcacggag gagatgctgt actgcgcgac gcgcgagaag ctggaccccg 2100
agttcgtccg ctccgaggtc gcgcggggcc gcgccatcat cccctccaac aagaagcacc 2160
tggagctgga gcccatgatc gtgggccgca agttcctggt gaaggtgaac gccgacatcc 2220
gcaactccgc cgtggcctcc tccatcgagg aggaggtcta caaggtgcag tgggccacca 2280
tgtggggcgc cgacaccatc atggacctgt ccacgggccg ccacatccac gagacgcgcg 2340
agtggatcct cgcgcaactcc gcggtccccg tgggcaccgt ccccatctac caggcgctgg 2400
agaaggtgga cggcatcgcg gagaacctga actgggaggt gttccgcgag acgctgatcg 2460
agcaggccgt gcaggcgtg gactacttca cgatccacg gggcgtgctg ctgcgctaca   2520
tcccctgac cgccaagcgc ctgacgggca tcgtgtcccg cggcggctcc atccacgcga   2580
agtggtgcct ggcctaccac aaggagaact tcgcctacga gcactgggac gacatcctgg 2640
acatctgcaa ccagtacgac gtcgcccgt ccatcggcga cggcctgcgc cccggctcca   2700
tctacgacgc caacgacacg gcccagtccg ccgagctgct gacccagggc gagctgacgc 2760
gccgcgtg ggagaaggac gtgcaggtga tgaacgaggc cccgtgccg gtgcccatgc    2820
acaagatccc cgagaacatg cagaagcagc tggagtggtg caacgaggcg cccttctaca 2880
ccctgggccc cctgacgacc gacatcgcgc ccggctacga ccacatcacc tccgccatcg 2940
gcgcggccaa catcggcgcc ctgggcaccg ccctgctgtg ctacgtgacg cccaaggagc 3000
acctgggcct gcccaaccgc gacgacgtga ggcggcgcgt catcgcctac aagatcgccg 3060
cccacgcggc cgacctggcc aagcagcacc cccacgccca ggcgtgggac gacgcgctgt 3120
```

-continued

```
ccaaggcgcg cttcgagttc cgctggatgg accagttcgc gctgtccctg gaccccatga   3180
cggcgatgtc cttccacgac gagacgctgc ccgcggacgg cgcgaaggtc gcccacttct   3240
gctccatgtg cggccccaag ttctgctcca tgaagatcac ggaggacatc cgcaagtacg   3300
ccgaggagaa cggctacggc tccgccgagg aggccatccg ccaggcatg gacgccatgt   3360
ccgaggagtt caacatcgcc aagaagacga tctccggcacg gcagcacggc gaggtcggcg   3420
gcgagatcta cctgcccgag tcctacgtca aggccgcgca gaagtgagtc ctggcgaccg   3480
tgctcccctg acccctgttc ccctgcgctg cttctccccg gtgacatccg acctgctgca   3540
aaattcccgt tcctgcacaa cacttgcctg accgagggtc gggtcgcgaa gtaaaagcca   3600
caatcaacac cccaggcaca ttaagagtgc acagcatgac gcagcatagg gtttgtgtcg   3660
gaggaagggg gtcgagtcgc gttggcgagg gggtggtcac gatgaccaca tctgcgggat   3720
aattgaatcc tcaggggaaa ataccagtct ctgcttccag gtgctccgac tagtcttgca   3780
gtgccccaaa aactggctac cacctaacaa ttctcacgca gttttatcct ctgcactttg   3840
atgtcagctt tttgattcgt ctgcgtacat tacagcgttg agtggccagc aggaaggaga   3900
ccgcggtccg agacgagtct gagggcgcgc tctcgcaact tggattccgg atttcttacc   3960
ctgcatcgac ctcggcctgg agtcgatcag aaattgtcat tgccagattg cctggcgagg   4020
acgggtgata tactcaaggc gttcgatcgc ccacaaaaca cacacttatc tgcaagggag   4080
ttactgcatc aggctctgct caacagctcg tgacatcgat cgttcagctc cccagcaggt   4140
gcgtgtccgc atggagcacc ctcccgaga cacctgcgtt gggtgtcgga ggagctcaca   4200
tgccagggag gtgcccacat tgcaccacgc gaccgcgaaa taggcagact tcgggcatcc   4260
tgtcatcgca tgtccgctgg ccgggaatca tggcctcccc accaggcgtc acgcgctgcc   4320
cacctccctc cccttgctgc gcagggcacc gcgttcctgt ggagagccga ccacatggtc   4380
ctgtgcgctg gtagtttgag ctgcagggcg ccgccttcag ggtgtgctag gttggagcgg   4440
gggtccccct tcgtgcgcct gggccaccat gcccgcccac aagctcgcag acggatgtca   4500
gacctcgtaa taaggtccat cgcagcccct gctccgcccc cgctgcgacc tgcatctcag   4560
cctcaagccc cacctgcatc agagaccttc acggtgagtc atgatcgagg tcggcccctg   4620
cagcgctcgt gctccggaaa cgacccgcta ctcaatccct gaaccatgaa tacttcaggg   4680
gggccgcgaa ctggccaacc gccctcctt ctccctccaa gacatccgca acgccatccc   4740
ggcggagtgc tggaagaagg acaccttcaa gtccttcgcc tacctggcgc tagatgtagg   4800
aatcgttgct gccctggccg tgacagcaca tgccgtcaac tcgccatggc tctggccctt   4860
ctactggcg gcgcagggga ccatgttctg ggccctgttt gtcgtcggcc acgactggtg   4920
cggttggagg gggtaatctg gcgaccctgc agggcatgca gtggggacaa gagcatcgcc   4980
aggctccgcc ttgcctgctg atcccagccc gacttggctg gacaatagat gctgtcgggg   5040
acatgccgca gtgcatgcca caatgggccc cttcaacaac tgaccaccac tatgacccat   5100
attccctgca gcggccacca gagcttcagc acaaacaagc agctgaatga cgtggaagct   5160
t                                                                  5161
```

```
SEQ ID NO: 14          moltype = DNA  length = 774
FEATURE                Location/Qualifiers
misc_feature          1..774
                       note = Nucleotide sequence of the ApFATA promoter in pPB0041
source                 1..774
                       mol_type = other DNA
                       organism = synthetic construct
SEQUENCE: 14
ggaatcccgc ctccgagatg aagccgtggt tggcacggag gaggccgctg cgggccagag   60
tgttcttctg ctgcacgtcc tccggctttg gtggctcgct gggcttgggt gcggccatga   120
gctgcagtgc aagtgtacat ataggtcaat cttatgccc ggcactacca atgatgatca   180
acaccgagcg gccctctgtg ttgtgcttgc ctctttacct tcactgcgta ctgctgcagg   240
agcttcatga ggatcacact gacggtcagg gggatcagca cccagtcccg gacatcccga   300
tccagtacga ggtcctggct gaccatgatg gtaggtgaag ttgggccctg ggaggagcgc   360
tagaggagcc tcggggcaaa gatcacccta ctctgacgtg gctggctcaa tcacccatcc   420
ctcccctttg aagtcggctc tcagtttgcg ttgtttcgaa atcgagccac aatcgaatat   480
acactaccta aaggctctca ccacctggcg tacctcggaa tgcccatcag cccaaacaca   540
tgagaaaagg cgcgcgcggt tcgacccag tccgtcgatt gacgcagtgg ggagctccat   600
tctgtcagct cttgggtggc caggtcgctg acagattgga cataacagga ccctgccgac   660
ccgttcctcc agcactttgt gaatttaagc agcgcattag atcgtcgatg gcttagagaa   720
ccccgcgcct gctccccat ctcccttca cacgtttgaa cacccggacc ggcc           774
```

```
SEQ ID NO: 15          moltype = DNA  length = 5651
FEATURE                Location/Qualifiers
misc_feature          1..5651
                       note = Nucleotide sequence of the transforming DNA from
                       pPB0118
source                 1..5651
                       mol_type = other DNA
                       organism = synthetic construct
SEQUENCE: 15
aagcttagca tactcctatt ctgacaatgt cacagtcggt ctgccaggcg atagtggctt   60
tgctgtcaga ctcggccccg gactctcccc tgaactgcga cgccggggaat ctgttgagag   120
gaggcgatct gcgagggttc gcctccatgg cccgcatgta caccatcgag tatgccatga   180
agcgatgatg tctgtgaaaa tgatgttcag aattcattat atactcatgt ttttgtgtaa   240
atgctgtgtc gacttaagtt accgagctgg ctgacagaga caatcttcag gtcaaatgtt   300
ggcaccaatg atcgcgacga tcgttcaggg gttatcaagt cagatctgaa cgaaaaccag   360
aaatcaaatt tgccaaagcg catgtttgta tgtcgagaat tatcatgcgg gtgactggct   420
cgctaattct ggcatggaag gatgccacat cgaattgatc cgggggagact aacacttgtc   480
agaattgcaa tgtgccatat tccagatatc ccagccggcc cttctataaa ccacctgcgg   540
gctcagatac ctacgaagag gctcagataa ctcaaggacg tgcattcgaa ttatccctgc   600
cgcgcggaaa catcagacca ggtgcggatg ctgacgtcg agttgggtgc ttgatagacc   660
ttcaccttga tctgaggttc ccgtccccag agcactcgaa tctccggcat cttacaggca   720
```

-continued

```
aaccgcaaac agtaaataat ggcgagcacc atcaccatgg gtaccccttgc agtgccccaa    780
aaactggcta ccacctaaca attctcacgc agttttatcc tctgcacttt gatgtcagct    840
ttttgattcg tctgcgtaca ttacagcgtt gagtggccag caggaaggag accgcggtcc    900
gagacgagtc tgagggcgcg ctctcgcaac ttggattccg gatttcttac cctgcatcga    960
cctcggcctg gagtcgatca gaaattgtca ttgccagatt gcctggcgag gacgggtgat   1020
atactcaagg cgttgcatcg cccacaaaac acacacttat ctgcaaggga gttactgcat   1080
caggctctgc tcaacagctc gtgacatcga tcgttcagct ccccagcagg tgcgtgtccg   1140
catggagcac ccctcccgag acacctgcgt tgggtgtcgg aggagctcac atgccaggga   1200
ggtgcccaca ttgcaccacg cgaccgcgaa ataggcagac ttcgggcatc ctgtcatcgc   1260
atgtccgctg gccgggaatc atggcctccc caccaggcgt cacgcgctgc ccacctccct   1320
cccccttgctg cgcagggcac cgcgttcctg tggagagccg accacatgtc cgccgccgcc   1380
gccgagaccg acgtgtccct cgcgccgccgc tccaactccc tgaacggcaa ccacaccaac   1440
ggcgtggcca tcgacggcac cctggacaac aacaaccgcg cgtgggcga caccaacacc   1500
cacatggaca tctccgccaa gaagaccgac aacggctacg ccaacggcct gggcggcggc   1560
ggctggcgct ccaaggcctc cttcaccacc tggaccgccc gcgacatcgt gtacgtggtg   1620
cgctaccact ggatccctg catgttcgcc gccggcctgc tgttcttcat gggcgtggag   1680
tacaccctgc agatgatccc cgcccgctcc gagcccttcg acctgggctt cgtggtgacc   1740
cgctccctga accgcgtgct ggcctcctcc cccgacctga acaccgtgct ggccgccctg   1800
aacaccgtgt tcgtgggcat gcagaccacc tacatcgtgt ggacctggct ggtggagggc   1860
cgcgcccgcg ccaccatcgc cgccctgttc atgttcacct gccgcggcat cctgggctac   1920
tccacccagc tgccctgcc ccaggacttc ctgggctccg gcgtggactt ccccgtgggc   1980
aacgtgtcct tcttcctgtt cttctccggc cacgtgggcg gctccatgat cgcctccctg   2040
gacatgcgcc gcatgcagcg cctgcgcctg gccatggtgt tcgacatcct gaacgtgctg   2100
cagtccatcc gcctgctggg caccccgcggc cactacacca tcgacctggc cgtgggcgtg   2160
ggcgccggca tcctgttcga ctccctggcc ggcaagtacg aggagatgat gtccaagcgc   2220
cacctgggca ccggcttctc cctgatcctc aaggactccc tggtgaactg agcgaggcc   2280
ttggaaatat tcgcgtcacg cgaggagtag gctctgctgg tcggccctgg atacgctgac   2340
tcttcaagca gtggggcacc acacccacct tttgccaagg gcaaggagtc ggaagggggc   2400
ggggctgcca tgcaccccctg acgggcatgg ccgttccgcg agggcgccaa ctgcggcggc   2460
ctgcccgctg gctcgtgccc ccctaccccc accattgcct ggagcgtttc catccccaaa   2520
tcacattcca tccaagttgt atcactatgc ccctttggct ctatacactc acggcctgag   2580
gtcccttctc ggccgtggcg gcacacgccc aacccccac catactcttt ccatacactg   2640
caatgcttcg agcctgcctg ccacctgctc tgcttgtctc ccctccttc ccttgaggtt   2700
ttccaatgca gtaagagaag tcgacgtgca tggacagatg attgagagat gagactagtc   2760
tttcttgcgc tatgacactt ccagcaaaag gtagggcggg ctgcgagacg gcttcccggc   2820
gctgcatgca acaccgatga tgcttcgacc ccccgaagct ccttcggggc tgcatgggcg   2880
ctccgatgcc gctccagggc gagcgctgtt taaatagcca ggcccccgat tgcaaagaca   2940
ttatagcgag ctaccaaagc catattcaaa cacctagatc actaccactt ctacacaggc   3000
cactcgagct tgtgatcgca ctccgctaag ggggcgcctc ttcctcttcg tttcagtcac   3060
aacccgcaaa catgctgctg caggccttcc tgttcctgct ggccggcttc gccgccaaga   3120
tcagcgcctc catgacgaac gagacgtccg accgccccct ggtgcacttc accccccaaca   3180
agggctggat gaacgacccc aacggcctgt ggtacgacga gaaggacgcc aagtggcacc   3240
tgtacttcca gtacaacccg aacgacacacc tctggggagc gccccttgttc tggggccacg   3300
ccacgtccga cgacctgacc aactgggagg accagcccat cgccatcgcc ccgaagcgca   3360
acgactccgg cgccttctcc ggctccatgg tggtggacta caacaacacc tccggcttct   3420
tcaacgacac catcgacccg cgccagcgct gcgtggccat ctggacctac aacacccccg   3480
agtccgagga gcagtacatc tcctacagcc tggacgacgg ctacaccttc accggagtacc   3540
agaagaaccc cgtgctggcc gccaactcca cccagttccg cgacccgaag gtcttctggt   3600
acgagccctc ccagaagtgg atcatgaccg cggccaagtc ccaggactac aagatcgaga   3660
tctactcctc cgacgacctg aagtcctgga agctggagtc cgcgttcgcc aacgagggct   3720
tcctcgacta ccagtacgag tgccccggcc tgatcgaggt ccccaccgag caggacccca   3780
gcaagtccta ctgggtgatg ttcatctcca tcaacccccgg cgcccccggcc ggcggctcct   3840
tcaaccagta cttcgtcggc agcttcaacg gcacccactt cgaggccttc gacaaccagt   3900
cccgcgtggt ggacttcggc aaggactact acgccctgca gaccttcttc aacaccgacc   3960
cgacctcggg gagcgccctg ggcatcgcgt gggcctccaa ctgggagtac tccgccttcg   4020
tgcccaccaa ccccctggcgc tcctccatgt ccctcgtgcg caagttctcc ctcaacaccg   4080
agtaccaggc caacccggag acggagctga tcaacctgaa ggccgagccg atcctgaaca   4140
tcagcaacgc cggccctgg agccggttcg ccaccaacac cacgttgacg aaggccaaca   4200
gctacaacgt cgacctgtcc aacagcaccg gcaccctgga gttcgagctg gtgtacgccg   4260
tcaacaccac ccagacgatc tccaagtccg tgttcggga cctctccctc tggttcaagg   4320
gcctggagga ccccgaggag tacctccgca tgggcttcga ggtgtccgcg tcctccttct   4380
tcctggaccg cgggaacagc aaggtgaagt tcgtgaagga gaaccccctac ttcaccaacc   4440
gcatgagcgt gaacaaccag cccttcaaga gcgagaacga cctgtcctac tacaaggtgt   4500
acggcttgct ggaccagaac atcctggagc tgtacttcaa ggagcggcac gtcgtgtcca   4560
ccaacaccta cttcatgacc accgggaacg ccctgggctc cgtgaacatg acgacggggg   4620
tggacaacct gttctacatc gacaagttcc aggtgcgcga ggtcaagtga ttgattggaa   4680
ctcacaaagc ggcccacggc ttcgaacgtc ccgtgtcaat tgcgcgggt gtgccagagt   4740
ttctgcgcca ccgatgctca ccctagggg ggatgccctt tgacattcat gtgtgcctgc   4800
atgcacgttt gtatcagtct caccacacct tgaagatttt tgggagggg gggaagtcg   4860
gaatgggaaac ctcgagcaac gctacgcaac tcccttcgat ggcttcaagt acggagatgt   4920
gggcatccag gattcgcatg tgctgcttca gccctcctca tgccactagc actcatttt   4980
cgactcccgg attgccaggt tcaagggcat caaggagtcg gagatcagcc gcgccatgac   5040
ctcccgctac ttcgaggacc taaacgtcaa tgccgaggtc cttttgcata tatttacagc   5100
taattatgat gggtgtggtg ccgcgatatgc ttgcaaggtc ttgcaggtgagc taatgatcgg   5160
cacatccctt ccgcgcatcc gcaggtcgat gtcgtcattg ttggggctgg gtctgcgggc   5220
ctctcgtgcg cctatgagct gagcaagcac ccggatgtca aggtatgggc tgagcagggc   5280
acatcctcag atgatgttgc tgtaattgca attgaaactt gcggttgttc ccagcacagc   5340
ctcaatcaat catgtgtgct gcgttggaaa cgctatgata ccccagcctt caacatgggg   5400
cagggatatc gtttacacct gcttgaaccc cccgcaacag gtggccatca tcgagcaggg   5460
```

-continued

```
cgtcgcccct gggggtggag cgtggctggg gggtcagctc ttctcggcta tgtgtgtgag   5520
tctaggcacg gggacgggtg gactgaagca agggttgggc gcagggtgtt gatatccatg   5580
tgttggacat tctcgttggg aaaacaagat gtgtgtattt agtgctatct cggtggctgc   5640
attccaagct t                                                        5651

SEQ ID NO: 16          moltype = DNA   length = 5526
FEATURE                Location/Qualifiers
misc_feature           1..5526
                       note = Nucleotide sequence of the transforming DNA from
                        pPB0142
source                 1..5526
                       mol_type = other DNA
                       organism = synthetic construct
SEQUENCE: 16
aagcttagca tactcctatt ctgacaatgt cacagtcggt ctgccaggcg atagtggctt   60
tgctgtcaga ctcggccccg gactctcccc tgaactgcga cgccgggaat ctgttgagag   120
gaggcgatct gcgagggttc gcctccatgg cccgcatgta caccatcgag tatgccgatga   180
agcgatgatg tctgtgaaaa tgatgttcag aattcattat atactcatgt ttttgtgtaa   240
atgctgtgtc gacttaagtt accgagctgg ctgacagaga caatcttcag gtcaaatgtt   300
ggcaccaatg atcgcgacga tcgttcaggg gttatcaagt cagatctgaa cgaaaaccag   360
aaatcaaatt tgccaaagcg catgtttgta tgtcgagaat tatcatgcgg gtgactggct   420
cgctaattct ggcatggaag gatgccacat cgaattgatc tggggagact aacacttgtc   480
agaattgcaa tgtgccatat tccagatatc ccagccggcc cttctataaa ccacctgcgg   540
gctcagatac ctacgaagag gctcagataa ctcaaggacg tgcattcgaa ttatccctgc   600
cgcgcggaaa catcagacca ggtgcggatg ctgagcgtcg agttgggtgc ttgatagacc   660
ttcaccttga tctgaggttc ccgtccccag agcactcgat tctccggcat cttacaggca   720
aaccgcaaac agtaaataat ggcgagcacc atcaccatgg gtaccccttgc agtgcccaa   780
aaactggcta ccacctaaca attctcacgc agtttttatcc tctgcacttt gatgtcagct   840
tttttgattcg tctgcgtaca ttacagcgtt gagtggccag caggaaggag accgcggtcc   900
gagacgagtc tgagggcgcg ctctcgcaac ttggattccg gatttcttac cctgcatcga   960
cctcggcctg gagtcgatca gaaattgtca ttgccagatt gcctggcgag gacgggtgat   1020
atactcaagg cgttgcatcg cccacaaaac acacacttat ctgcaaggga gttactgcat   1080
caggctctgc tcaacagctc gtgacatcga tcgttcagct ccccagcagg tgcgtgtccg   1140
catggagcac ccctcccgag acacctgcgt tgggtgtcgg aggagctcac atgccaggga   1200
ggtgcccaca ttgcaccacg cgaccgcgaa ataggcagac ttcgggcatc ctgtcatcgc   1260
atgtccgctg gccgggaatc atggcctccc caccaggcgt cacgcgctgc ccacctccct   1320
cccccttgctg cgcagggcac cgcgttcctg tggagagccg accacatgtc cccccccaac   1380
tccatgtccc ccgccaccaa cggctccacc aacggcgtgg ccatcaacgg cgccaagaag   1440
ctgctggact tcgacccctc cgccgccccc cccttcaaga tcgccgacat ccgcgccgcc   1500
atccccccccc actgctgggt gaagaacccc tggcgctccc tgtcctacgt gctgcgcgac   1560
ctgctggtga tcctgtcctt cgccgtggcc gccaccaagc tggactcctg gaccgtgtgg   1620
cccctgtact ggatcgccca gggcaccatg ttctgggccg tgttcgtgct gggccacgac   1680
tgcggccacg gctccttctc cgactcctgg ctgctgaaca acgtgatggg ccacatcctg   1740
cactcctcca tcctggtgcc ctaccacggc tggcgcatct cccacaagac ccaccaccag   1800
aaccacggca acgtggagaa ggacgagtcc tgggtgcccc tgcccgagaa ggtgtacaag   1860
tccctggaca ccggcaccaa gttcatgcgc ttcaccatcc ccctgccatt gttcgcctac   1920
cccatctacc tgtggcgccg ctcccccggc aagaaggcct cccacttcaa ccccctactcc   1980
gacctgttcg cccccaacga gcgcacctcc gtgatgatct ccaccctgtg ctggaccgcc   2040
atggccctgc tgctgctcta ctcctccttc atctacggct tcctgcccgt gttcaagatc   2100
tacggcgtgc cctacctgat cttcgtggcc tggctggaca tggtgaccta cctgcaccac   2160
cacggctacg agcagaagct gcccctggtac aggggcctcta cctgcgcggc   2220
ggcctgacca ccgtgaccg cgactacggc gtgatcaaca acatccacca cgacatcggc   2280
acccacgtga tccaccacct gttccccccag atgcccccact accacctggt ggaggccacc   2340
caggccgcca agcacgtgct gggcaagtac taccgcgagc ccaagaagtc cggcccccttc   2400
cccttccacc tgttcggcta cctggtgcgc tccctggacg aggaccacta cgtgtccgac   2460
accggcgacg tggtgttcta ccagtccgac ccccacatcc ccaagttccc cacctccgcc   2520
accaccaagt ccaagtcctc ctgagtgatc cgggaggagg gagtgagcgg ggaaggggc   2580
agccacacgg ggcccgtctc gacctgccac ccctcccctc gtcgagccct gcccaggggg   2640
cgccgcaacg agccatgcgt gtgcatgtgt ctggagggcc cttccaccgg gcgatgtgcg   2700
agccatcctc gcctatttca acacaccgct gccggcatgc gctccactcc ccccaaaacc   2760
acctcgaccc tccagggct cctccccgc cccaccctgc ctgctgatat agaaaccagt   2820
gttctgtgaa cgtttgacat gctcaacgag ggtacagggg tgcaccaaca gaggaggagt   2880
ggttcacaca gtcggataca ctagtccttc ctgtcccaca atgcttggtg aatgcagtgg   2940
gttgatcacc gcggaggagc tgtggcttac tcgttctgat caagggagcc tctgcacctt   3000
aaccctgcca ggatcgaaac caaccttgtc agtcccgtgg tgggcaacat catcctcgtg   3060
aagctgattg accaggaaaa catgatgagt cggtatgagg acgagcatga gtggcccaac   3120
atcgatatga cacatcttgg agtttacggc aaatgtatca cacttccatc ctggcttgca   3180
ccacaatatt agtggacccc tccttgcagt ggcacggtga gaagctagtt tgtagtaatc   3240
ttcttaattg acgaaccaga cgtgtgtaat ggcctccttt gagtgatgga aggatggaac   3300
ctaccccccc cctccccagt actctgcggt acatccgagt aacccttcca ttgatcagcc   3360
caaacgcaat atgcaacgac tctacatacg gccaccgagt gcttattcct tcgctatcac   3420
cgcacaaaaa tcccatccgc gaactcatcc gaggtgatag attgcgatcg gggttattcg   3480
ggttaaggtg cgactaggga tccctgaatc ttttggggat ttccccgggt ctcgtcctgc   3540
atgcttatca tcagtctcgt gggttatttg gatcgctgcg actgccataa cagagcgctc   3600
ataatatttg ctgcgcggt ggtgctggca aaatcccctg cgtaccgggc gcctgtcaag   3660
ccaaccccgc cgtgcggcac tccccctgcag atccatcacc atgatcgagc aggacggcct   3720
ccacgccggc tccccccgccg cctgggtgga gcgcctgttc ggctacgact gggcccagca   3780
gaccatcggc tgctccgacg ccgccgtgtt ccgcctgtcc gcccagggcc gccccgtgct   3840
gttcgtgaag accgacctgt ccggcgccct gaacgagctg caggacgagg ccgccgcct   3900
```

```
gtcctggctg gccaccaccg gcgtgccctg cgccgccgtg ctggacgtgg tgaccgaggc   3960
cggccgcgac tggctgctgc tgggcgaggt gcccggccag gacctgctgt cctcccacct   4020
ggcccccgcc gagaaggtgt ccatcatggc cgacgccatg cgccgcctgc acaccctgga   4080
ccccgccacc tgccccttcg accaccaggc caagcaccgc atcgagcgcg cccgcacccg   4140
catggaggcc ggcctggtgg accaggacga cctggacgag gagcaccagg gcctggcccc   4200
cgccgagctg ttcgcccgcc tgaaggcccg catgcccgac ggcgaggacc tggtggtgac   4260
ccacggcgac gcctgcctgc caacatcat ggtggagaac ggccgcttct ccggcttcat   4320
cgactgcggc cgcctgggcg tggccgaccg ctaccaggac atcgccctgg ccacccgcga   4380
catcgccgag gagctgggcg gcgagtgggc cgaccgcttc ctggtgctgt acggcatcgc   4440
cgcccccgac tcccagcgca tcgccttcta ccgcctgctg gacgagttct tctgagctgt   4500
tcctaggaac gtgggaggag tgcaaggagg gtgatctcac cctggtgtgt ctcttcatgg   4560
agctcagatc ttgaaaactg tgaggtgctt atccgatacc tgcttcgtgc atggcttgtg   4620
cgatatgtac acgcatttgc agattggtgg gagcagcaga ttggtgggag cagcatagag   4680
ctttagaagg ggcttaggag cgggaatgtg aaactcaggc ggttgggcca gatgagagcg   4740
caaagggatc ccaacgctac gcaactccct tcgatggctt caagtacgga gatgtgggca   4800
tccaggattc gcatgtgctg cttcagccct cctcatgcca ctagcactca tttttcgact   4860
cccggattgc caggttcaag ggcatcaagg agtcggagat cagccgcgcc atgacctccc   4920
gctacttcga ggacctaaac gtcaatgccg aggtgctttt gcatatattt acagctaatt   4980
atgatggggtg tggtgcgcga tatgcttgca aggtctccgt gtagctaatg atcggacact   5040
cccttccgcg catccgcagg tcgatgtcgt cattgttggg gctgggtctg cgggcctctc   5100
gtgcgcctat gagctgagca agcaccggga tgtcaaggta tgggctgagc agggcacatc   5160
ctcagatgat gttgctgtaa ttgcaattga aacttgcggt tgttcccagc acagcctcaa   5220
tcaatcatgt gtgctgcgtt ggaaacgcta tgatacccca gccttcaaca tggggcaggg   5280
atatcgttta cacctgcttg aacccccgc aacaggtgc catcatcgag cagggcgtcg   5340
cccctggggg tggagcgtgg ctgggggggtc agctcttctc ggctatgtgt gtgagtctag   5400
gcacggggac gggtggactg aagcaaggg tgggcgcagg gtgttgatat ccatgtgttg   5460
gacattctcg ttgggaaaac aagatgtgtg tatttagtgc tatctcggtg gctgcattcc   5520
aagctt                                                               5526
```

```
SEQ ID NO: 17          moltype = DNA   length = 1380
FEATURE                Location/Qualifiers
misc_feature           1..1380
                       note = Coding sequence of KASII from A. protothecoides,
                        optimized for translation
source                 1..1380
                       mol_type = other DNA
                       organism = synthetic construct SEQUENCE: 17
atggccaccg cctccctgcc cgtgcaggtg gccgtgacct ccacccactg cttcggcctg   60
cgcgagcccc gccgcaagcg ccagtgggcc cgccagaccc gctgccacgc ctccgccgcc   120
ggcaagccca gcgccgcgt ggtggtgacc ggccagggcg tggtgacctc cctgggccag   180
tccacccagc agttctacga ccagctgctg gccggcgcct ccggcatcac ccacatcgag   240
ggcttcgaca cctccgacta ctccaccaag atcgccggcg aggtgaagtc cgtggacgcc   300
gcccctacg tggcccgcaa gtgggtgaag cgcatggacg aggtgatgaa gttcatgttc   360
gtggccggca agcaggccct ggaggacgcc ggcctgcccc tcgagggccc cggcctggag   420
gacctggacc gcaagctgtg cggcatcctg atcggcaccg ccatgggcgg catgaccacc   480
ttcgcctccg gcgtggaggc cctgaccctg tccggccacc gcaagatgaa ccccttctgc   540
atccccttct ccatcggcaa catgggcggc gccatgctgg ccatggacct gggcttcatg   600
ggccccaact actccatctc caccgcctgc gccaccggca actactgcat catctccgcc   660
gccgaccaca tccgcaacgg cgacgccgtg ctgatgctgg cgggcggcgc cgacgccgcc   720
gtgatcccct ccggcatcgg cggcttcatc gcctgcaagg ccctgtcccg ccgcaacgac   780
gcccccgagc gcgcctcccg cccctgggac gccggccgcg acggcttcgt gatgggcgag   840
ggcgccggcg tgctggtgct ggaggagctg gagcacgccc gcgcccgcgg cgccaccatc   900
ctggccgagt tcatcggcgg cgcggccacc tgcgacgccc accacatgac cgagcccgag   960
cctccggcc gcggcgtgcg cctgtgcctg gagcgcggcc tggccgccgcg cggcctggag   1020
cccgaggagg tgacctacgt gaacgcccac ggcacctcca ccccccgcgg cgacgtggcc   1080
gagttccgcg ccatccgcgc cgtgctgggc cacgacggcc tgcgcatcaa ctcctccaag   1140
ggcgccatcg gccacctgct gggcgcggcg ggcgccgtgg aggccgtggc caccatccag   1200
gccctgcgca ccggctggct gcaccccaac ctgaacctgg acgagcccga caagggcgtg   1260
gacgcctccg tgctggtggg cggcgtgaag gagcaggccg acgtgaaggt ggccctgtcc   1320
aactccttcg gcttcggcgg ccacaactcc tgcgtgctgt ccgcaagtt cgaggagtga   1380
```

```
SEQ ID NO: 18          moltype = AA   length = 459
FEATURE                Location/Qualifiers
REGION                 1..459
                       note = Amino acid sequence of A. protothecoides
                        beta-ketoacyl-ACP synthase II
source                 1..459
                       mol_type = protein
                       organism = synthetic construct SEQUENCE: 18
MATASLPVQV AVTSTHCFGL REPRRKRQWA RQTRCHASAA GKPKRRVVVT GQGVVTSLGQ   60
STQQFYDQLL AGASGITHIE GFDTSDYSTK IAGEVKSVDA APYVARKVVK RMDEVMKFMF   120
VAGKQALEDA GLPFEGPGLE DLDRKLCGIL IGTAMGGMTT FASGVEALTL SGHRKMNPFC   180
IPFSIGNMGG AMLAMDLGFM GPNYSISTAC ATGNYCIISA ADHIRNGDAV LMLAGGADAA   240
VIPSGIGGFI ACKALSRRND APERASRPWD AGRDGFVMGE GAGVLVLEEL EHARARGATI   300
```

-continued

```
LAEFIGGAAT CDAHHMTEPE PSGRGVRLCL ERGLAAAGVA PEEVTYVNAH GTSTPAGDVA  360
EFRAIRAVLG HDGLRINSSK GAIGHLLGAA GAVEAVATIQ ALRTGWLHPN LNLDEPDKGV  420
DASVLVGGVK EQADVKVALS NSFGFGGHNS CVLFRKFEE               459
```

PRODUCTION OF LIPIDS AND TERPENOIDS IN *AUXENOCHLORELLA PROTOTHECOIDES*

CROSS-REFERENCE TO RELATED APPLICATIONS

This application is a divisional of U.S. patent application Ser. No. 17/519,854, filed on Nov. 5, 2021, which claims the benefit of U.S. Provisional Patent Application No. 63/109, 901 filed Nov. 5, 2020, the entire disclosure of each of which is hereby incorporated by reference in its entirety for all purposes.

REFERENCE TO SEQUENCE LISTING, TABLE OR COMPUTER PROGRAM

The official copy of the Sequence Listing is submitted concurrently with the specification as an xml file, made with WIPO Sequence Version 2.1.0, via EFS-Web, with a file name of "PBI009.xml", a creation date of May 24, 2024, and a size of 66 kilobytes. The Sequence Listing filed via EFS-Web is part of the specification and is incorporated in its entirety by reference herein.

TECHNICAL FIELD

The present invention describes microalgae having a functional oil-producing ability comprising an altered profile of fatty acids, carotenoids and/or terpenoids and a method of extracting oil using the microalgae. More specifically, it relates to a method for producing oil having modified fatty acids, carotenoids and/or terpenoids content compared to wild-type microalgae, such as *Auxenochlorella protothecoides* with inhouse strain designation as PB5.

BACKGROUND ART

Industrial production of lipids and fats from oleaginous microorganisms has been investigated since the late 19th century, but the promise of these "single cell oils" has only been realized in the last 20-30 years[1]. Oleaginous microorganisms trigger biosynthesis of storage lipids in response to imbalances between carbon (C) supply and other major nutrients such as nitrogen (N) or phosphorus (P) that are required for growth. This response allows accumulation of excess C under conditions where limitation for other nutrients prevents cell growth and division. Microbial storage lipids are largely composed of triacylglycerides (TAGs), which can be mobilized and used for rapid growth when the limiting nutrient or nutrients become available. Subsets of yeasts, fungi, and algae, but very few bacteria are oleaginous[1]. In the case of some algae, oil production can be stimulated by photosynthesis or by heterotrophic fermentation of sugars, but there is little economic incentive to make lipids which have similar composition or properties to commodity plant oils. In the early 2000s there was a flurry of interest and investment in photosynthetic production of biofuels from algae, but this has now largely faded due to the unfavorable energy return and economics of fuel production from aquatic microbes[2,3]. Heterotrophic oil productivity is substantially higher than is the case for photoautotrophic production, but the price of common sugar feedstocks is seldom any less that one quarter of the price of typical commodity oils, and the lipid yield for most heterotrophic processes is less than 25%. The economics can improve if the carbon source comes from a low value waste stream (e.g., lactose from cheese production, cellulosic sugars from agricultural waste).

On the other hand, heterotrophic production of very long chain polyunsaturated fatty acids (VLCPUFAs) from algae, thraustochytrids and yeasts provides a roadmap for successful commercialization of microbial oils. Docosahexaenoic acid (DHA) from the dinoflagellate algae *Cryptheco dinium cohnii* and arachidonic acid (ARA) from the yeast *Mortierella alpina* are both important components of infant formula[1]. These fatty acids are important components of human breast milk and are vital for brain and nervous system development[4]. The microbial oils address a particular market need for which there are no appropriate substitutes, since the only other significant sources of VLCPUFAs come from fish oils which are subject to contamination with toxins and heavy metals.

Other successful commodity products from aquatic microalgae follow the VLCPUFA model. Astaxanthin and beta-carotene are key carotenoids for human nutrition; the former is one of the most powerful antioxidants known, while beta-carotene also has strong antioxidant activity and is a pro-vitamin A supporting vision[5]. Synthetic astaxanthin derived from petrochemicals is used extensively as a colorant in fish farming but is not approved for human consumption in food or supplements. The major natural source of astaxanthin is the chlorophyte *Haematococcus lacustris* (also *H. pluvalis*), which is grown photoautotrophically in ponds or bioreactors. Haematococcus cultures can produce up to 5% of their biomass as astaxanthin when they are subjected to nutrient and high light stress. Astaxanthin is also produced commercially by the heterotrophic fermentation of the yeast *Phaffia rhodozyma*, but the carotenoid content of the biomass is much lower than *Haematococcus*[6, 7]. Natural beta-carotene is extracted from another chlorophyte, the halophile *Dunaliella salina*, which is grown photoautotrophically in large salt ponds. Both *Haematococcus* and *Dunaliella* fetch high prices for the biomass, but photoautotrophic cell densities are too low and the production costs for harvesting and extraction are too high for the natural sources to reach the scale where they can compete with synthetic carotenoids.

Squalene is an important component of human sebum (12%), a fact that justifies its role in the physiology of skin[8], its action in skin hydration, repairing of the damaged skin, and rejuvenating the aging skin was demonstrated. The emollient and hydration properties of squalene and its biocompatibility with skin make squalene an important component in cosmetic formulations (moisturizing creams, makeup, lipstick, and nail and hair products).

Furthermore, squalene appears to play an essential role in protecting skin from free radical oxidative damage. Squalene acts in skin as a quencher of singlet oxygen, protecting by this mechanism the skin surface from lipid peroxidation due to exposure to UV light.

Squalene has been known to play diverse biological roles as an antioxidant[9,10], anti-cancer agent[10,11], age defyer[12,13], chemo preventive agent[14,15,16], antibacterial agent[13,17], adjuvant for vaccines and drug carrier[18,19], and detoxifier[11,20] among others.

Squalene has proved to be a well-tolerated, non-toxic cytoprotective agent that mitigates undesirable side effects of cancer chemotherapy. Many anticancer therapies damage normal healthy tissues, even to the point of organ toxicity. These toxic secondary effects can limit the anticancer drug dosage, and even lead to treatment failure. Squalene is effective at scavenging and detoxifying free radicals produced by chemotherapeutic or radiation therapy agents.

The role of squalene is not just confined to these applications, but it is also a precursor to thousands of bioactive molecules, including steroids and hopanoids. Consequently, many chemicals, food, cosmetic, and pharmaceutical industries have started to use squalene extensively. It also acts as a boosting agent, or adjuvant, that improves the immune system and makes vaccines more effective. Over the last decade, global squalene demand has increased and gained much public and scientific attention. In 2014, the global squalene market demand was about 2.67 kilotons[21], with a projected value of 241.9 million USD by 2022, with major revenues expected from the personal care and cosmetic products[22]. In order to fulfill this ever-increasing demand of squalene, a pressing need has arisen to produce squalene in a renewable and sustainable manner.

Squalene is harvested from deep-sea sharks and exists in high concentration in shark liver. However, the intensive fishing of these sharks puts in danger the existence of these species, with many of them being close to extinction as their reproductive cycle is quite long and the growth is slow.

Most plant seed oils contain small amounts of squalene[23]. This phytosqualene has superior qualities compared to shark squalene, in that it is highly stable, generally free of heavy metal contamination, odorless, and colorless. In spite of containing significant amounts of squalene, plants oils are not ideal sources. Some plants are strictly seasonal, and squalene content varies greatly geographically. Oilseed crops require the appropriate climatic conditions, soil quality, scheduled irrigation or sufficient rainfall, fertilizer, and pest management. The process of cultivation is labor intensive and correspondingly the amount of squalene produced from plant sources is not sufficient to fulfill the increasing worldwide demand.

Several microalgae and other microorganisms accumulate comparable levels of squalene to plant oils. Short generation times and ease of genetic engineering make microalgae a better alternative for squalene production than plants.

Native biosynthetic pathways which include squalene as an intermediate are present in many microalgae, and these pathways can be transformed or extended to convert the organisms into "cellular factories" for squalene production.

*Auxenochlorella prototothecoides* is one of the most oleaginous species of microalgae and can be cultivated heterotrophically with productivity in commercial scale[24]. Metabolic engineering using genetic tools on this organism has strong potential to produce variety products including carotenoids, terpenoids, and other active ingredients, which can be an important alternative source of currently depleted natural resources.

BRIEF SUMMARY OF THE INVENTION

The inventors of the present application have developed the Trebouxiophyte alga, *Auxenochlorella prototothecoides* PB5, as a biotechnology platform for the heterotrophic production of valuable lipids, carotenoids, terpenoids, and other compounds. Efficient transformation and facile gene targeting by homologous recombination are features of this system. Targeted knockouts and knock-ins of fatty acid and lipid biosynthetic pathway genes enabled the improved synthesis of polyunsaturated fatty acids. Valuable ketocarotenoids were produced by disrupting endogenous carotenoid biosynthetic genes and expressing heterologous beta-carotene ketolase transgenes. Squalene accumulation was increased by blocking phytosterol biosynthesis. *A. prototh-*

4

*ecoides* PB5 can be employed as a general platform for the photoautotrophic, mixotrophic, or heterotrophic production of valuable biomolecules. Here the inventors of the present application demonstrate the utility of the system for the biosynthesis of modified fatty acids, lipids, carotenoids, and other terpenoids (FIG. 1).

It is an object of the present invention to provide mutant microalgae having functional oil-producing ability comprising modified profiles of fatty acids, carotenoids and/or terpenoids as proposed to solve the above problems.

Another object of the present invention is to provide a method for producing oil using the microalgal mutant.

Another object of the present invention is to provide oil prepared by the above production method.

Advantageous Effects

The present application shows that when using a microalgal mutant in which *Auxenochlorella prototothecoides* PB5 microalga genes are knocked out or knocked in by homologous recombination, an oil containing fatty acids, carotenoids and/or terpenoids of an altered profile compared to that of wild type thereof can be effectively extracted.

DESCRIPTION OF THE DRAWING

FIG. 1 shows a diagram of the Isoprenoid pathway, an essential metabolic pathway present in microalgae.

FIGS. 2A-B show the sequence of the transforming DNA from the LCYE-1 disruption construct pPB0014. (SEQ ID NO: 1)

FIGS. 3A-C show the sequence of the transforming DNA from the LCYE-2 disruption construct pPB0038. (SEQ ID NO: 2)

FIG. 4 shows spectrophotometric and HPLC analysis of carotenoid pigments from wild-type *A. prototothecoides* PB5, 14-2, and 38-25. Absorbance spectra of acetone-methanol-extracted pigments from wild-type *A. prototothecoides* PB5, LCYE-1 disruption strain 14-2, and LCYE-1/ LCYE-2 double knockout strain 38-25. Peak absorbances are indicated for each curve (A). HPLC chromatograms showing carotenoid pigments present in oil extracted from the same strains as in A (B).

FIG. 5 shows the sequence of the expression module cloned into the KpnI site of pPB0038 to generate construct pPB0120. (SEQ ID NO: 3)

FIG. 6. Nucleotide sequence of the ApSAD2tp_CrBKT1 expression module from pPB0123. (SEQ ID NO: 4)

FIG. 7A shows the amino acid sequence of native CrBKT1. The predicted plastid transit peptide is underlined. (SEQ ID NO:5)

FIG. 7B shows the amino acid sequence of chimeric ApSAD2tp_CrBKT1. The predicted ApSAD2 plastid transit peptide is underlined. (SEQ ID NO:6)

FIG. 8 shows shake flask cultures illustrating the color differences due to engineered alterations in the carotenoid profiles (A). HPLC chromatograms showing carotenoid pigments present in oil extracted from the same strains as in A (B).

FIGS. 9A-C show the sequence of the transforming construct pPB0065, targeting disruption of ApSQE-2. (SEQ ID NO: 7)

FIGS. 10A-B show the sequence of the transforming DNA from pPB0077. (SEQ ID NO: 8)

FIG. 11 shows the chromatograms of HPLC analysis of the standard squalene (A), the accumulation of squalene in SQE double knockout strain 77B-21 (B).

FIG. 12 shows the amino acid sequence of *A. protothecoides* 1-deoxy-D-xylulose 5-phosphate synthase (DXS). The predicted plastid transit peptide is underlined. (SEQ ID NO:9)

FIG. 13 shows the amino acid sequence of *A. protothecoides* 1-deoxy-D-xylulose 5-phosphate reductoisomerase (DXR). (SEQ ID NO:10)

FIG. 14 shows the amino acid sequence of *A. protothecoides* farnesyl diphosphate synthase (FDPS). (SEQ ID NO:11)

FIG. 15 shows the amino acid sequence of *A. protothecoides* squalene synthase (SQS). (SEQ ID NO:12)

FIGS. 16A-C show the sequence of the transforming construct pPB0039, targeting insertion of the ApSAD2 promoter upstream of the FAD3-1 coding sequence. (SEQ ID NO: 13)

FIG. 17 shows the nucleotide sequence of the ApFATA promoter in pPB0041 SEQ ID NO: 14)

FIGS. 18A-C show the sequence of the transforming construct pPB0118, targeting AtPDCT and ScSUC2 expression to the THI4 locus. (SEQ ID NO: 15)

FIGS. 19A-C show the sequence of the transforming construct pPB0142, targeting LuFAD3A and neoR expression to the THI4 locus. (SEQ ID NO: 16)

FIG. 20 shows the growth of strains targeting one or both alleles of THI4. Wild-type *A. protothecoides* PB5 is unable to grow without added thiamine. Thiamine prototrophy is observed in strain 118B-8, expressing AtTHIC, targeted to one allele of THI4. Disruption of the second THI4 allele by pPB0142 renders the transformants thiazole auxotrophs.

FIG. 21 shows the coding sequence of KASII from *A. protothecoides*, optimized for translation. (SEQ ID NO:17)

FIG. 22 shows the amino acid sequence of *A. protothecoides* beta-ketoacyl-ACP synthase II. (SEQ ID NO:18)

DETAILED DESCRIPTION OF THE INVENTION

Unless otherwise defined herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner like a term "comprising." The transitional terms/phrases (and any grammatical variations thereof) "comprising," "comprises," "comprise," "consisting essentially of," "consists essentially of," "consisting," and "consists of" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the value as determined by one of ordinary skills in the art, which will depend in part on how the value is measured or determined, i.e., the limitations of the measurement system. Where values are described in the application and claims unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

An "allele" refers to a version of a gene at the same place on homologous chromosomes. An allele may encode the same or similar protein.

"Exogenous gene" shall mean a nucleic acid that codes for the expression of an RNA and/or protein that has been introduced into a cell (e.g., by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Fixed carbon source" is a molecule(s) containing carbon, typically an organic molecule that is present at ambient temperature and pressure in solid or liquid form in a culture media that can be utilized by a microorganism cultured therein. Accordingly, carbon dioxide is not a fixed carbon source.

"Microalgae" are eukaryotic microbial organisms that contain a chloroplast or other plastid, and optionally that can perform photosynthesis, or a prokaryotic microbial organism capable of performing photosynthesis. Microalgae include obligate photoautotrophs, which cannot metabolize a fixed carbon source as energy, as well as heterotrophs, which can live solely off a fixed carbon source. Microalgae include unicellular organisms that separate from sister cells shortly after cell division, such as Chlamydomonas, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as Agmenellum, Anabaena, and Pyrobotrys. Microalgae also include obligate heterotrophic microorganisms that have lost the ability to perform photosynthesis.

In connection with a recombinant cell, the term "knockdown" refers to a gene that has been partially suppressed (e.g., by about 1-95%) in terms of the production or activity of a protein encoded by the gene.

Also, in connection with a recombinant cell, the term "knockout" refers to a gene that has been completely or nearly completely (e.g., >95%) suppressed in terms of the production or activity of a protein encoded by the gene. Knockouts can be prepared by ablating the gene by homologous recombination of a nucleic acid sequence into a coding sequence, gene deletion, mutation, or other methods. When homologous recombination is performed, the nucleic acid that is inserted ("knocked-in") can be a sequence that encodes an exogenous gene of interest or a sequence that does not encode for a gene of interest.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous (especially eukary-otic microalgae that store lipid). An oleaginous cell also encompasses a cell that has had some or all its lipid or other content removed, and both live and dead cells.

In connection with a functional oil, a "profile" is the distribution of species or triglycerides or fatty acyl groups within the oil. A "fatty acid profile" is the distribution of fatty acyl groups in the triglycerides of the oil without reference to the attachment to a glycerol backbone. Fatty acid profiles are typically determined by conversion to a fatty acid methyl ester (FAME), followed by gas chroma-tography (GC) analysis with flame ionization detection (FID). The fatty acid profile can be expressed as one or more percent of fatty acid in the total fatty acid signal determined from the area under the curve for that fatty acid.

"Recombinant" is a cell, nucleic acid, protein, or vector that has been modified due to the introduction of an exog-enous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of the active gene product in a cell. A "recombinant nucleic acid" is a nucleic acid originally formed in vitro, in general, by the manipu-lation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombi-nantly, although subsequently replicated intracellularly, are still considered recombinant for purposes of this invention. Similarly, a "recombinant protein" is a protein made using recombinant techniques, i.e., through the expression of a recombinant nucleic acid.

The terms "triglyceride", "triacyl glyceride" and "TAG" are used interchangeably as is known in the art.

In the present disclosure, ranges are stated in shorthand, to avoid having to set out at length and describe each value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. When ranges are used herein, combinations and sub-combinations of ranges (e.g., subranges within the disclosed range), specific embodiments therein are intended to be explicitly included.

According to one aspect of the present invention, a method for producing oil comprising a fatty acid, carote-noid, and/or terpenoid of a modified profile using a gene knockout or knock-in microalgal mutant by homologous recombination is provided.

According to one aspect of the present invention, a method for producing oil, characterized in that the weight ratio of zeaxanthin to lutein is high compared to the oil produced from wild-type microalgae, is provided.

According to one aspect of the present invention, a method for producing an oil comprising astaxanthin is provided.

According to one aspect of the present invention, a method for producing an oil comprising squalene is pro-vided.

According to one aspect of the present invention, a method for producing a functional oil, characterized in that the weight ratio of omega-6 to omega-3 is low compared to the oil produced from wild-type microalgae, is provided. Preferably, the ratio of the oil ranges between 1:1 to 5:1 compared to the oil produced from the wild type microalgae which is 7:1.

According to one aspect of the present invention, a method for producing a functional oil, characterized in that the omega-3 fatty acids increased 3-5-fold and the overall PUFA increased 2-3-fold compared to the wild-type strain.

According to one aspect of the present invention, the microalgal mutant may be a gene knockout or knock-in microalgal mutant by homologous recombination. Prefer-ably, the microalgae may be Auxenochlorella genus, more preferably, Auxenochlorella prototothecoidesPB5.

According to one aspect of the present invention, the microalgae mutant is to provide a method for producing functional oil, characterized in that one or more of the alleles LCYE-1 and LCYE-2 of the Lycopene Cyclase Epsilon gene are knocked out.

According to one aspect of the present invention, the microalgal mutant strain may be to provide a method for producing a functional oil, characterized in that one or more of the alleles SQE-1 and SQE-2 of the Squalene Epoxidase gene are knocked out.

According to one aspect of the present invention, the microalgal mutant may be to provide a method for produc-ing a functional oil, characterized in that the native FAD3 promoter is replaced with a Stearoyl-ACP Desaturase (SAD2) promoter, or the native FAD3 promoter is replaced with an acyl-ACP thioesterase (FATA) promoter.

According to one aspect of the present invention, it may be to provide the use of microalgae as a platform to produce functional oils comprising fatty acids, carotenoids, and/or terpenoids of altered profile by modification of the isopre-noid pathway.

According to an aspect of the present invention, it may be to provide a mutant microalga for the production of oil containing fatty acids, carotenoids, and/or terpenoids of an altered profile.

According to an aspect of the present invention, it may be to provide an oleaginous microalgae mutant that produce a functional oil, the microalgae comprising an ablation of one or more alleles of an endogenous polynucleotide or com-prising an exogenous gene.

According to one aspect of the present invention, the microalgal mutant is a microalgal mutant knocked out or knocked-in by homologous recombination, preferably, at least one of the alleles LCYE-1 and LCYE-2 of lycopene cyclase epsilon characterized by knocking out, or knocking out at least one of alleles SQE-1 and SQE-2 of squalene epoxidase, or replacing the native FAD3 promoter with a Stearoyl-ACP Desaturase (SAD2) promoter or a mutant strain in which the native FAD3 promoter is replaced with the promoter of the A. prototothecoides FATA gene encoding acyl-ACP thioesterase.

Hereinafter, the present invention will be explained in detail.

As an aspect for achieving the object of the present invention, the present invention provides an *Auxenochlorella prototheocoides* mutant for producing a fatty acid, a carotenoid, or terpenoid having a modified profile.

As an embodiment, the *Auxenochlorella prototheocoides* mutant may be a mutant of *A. prototheocoides* PB5.

The *Auxenochlorella prototheocoides* mutant of the present invention may be prepared using general mutation treatment methods.

In the present invention, "mutation" refers to a change in a nucleotide sequence due to the insertion, deletion, or substitution of a base into the original nucleotide sequence. As a means of mutation, the number of inserted bases may be different depending on the mutation and thus is not limited thereto. "Deletion mutation" means a mutation in which a base is removed from the original nucleotide sequence, and "substitution mutation" means that an original nucleotide is changed to another base without changing the number in the original nucleotide sequence.

In a specific embodiment of the present invention, pPB0014 has a transforming DNA with the nucleotide sequence of SEQ ID NO: 1 which is a DNA construct in which LCYE-1 encoding one allele of Lycopene Cyclase Epsilon in *Auxenochlorella prototheocoides* PB5 is prepared in order to change the ratio of lutein derived from alpha-carotene and zeaxanthin derived from beta-carotene compared to wild type. Then, strain 14-2 was prepared by introducing pPB0014. Afterward, in order to generate a double knockout strain completely lacking lutein, a carotenoid derived from alpha-carotene, pPB0038, a DNA construct having a transforming DNA with the nucleotide sequence of SEQ ID NO: 2, in which LCYE-2 encoding the second allele of Lycopene Cyclase Epsilon was prepared. The mutant strain 38-25 is prepared by transforming the strain 14-2 with said pPB0038.

It was confirmed that the above strains increased the ratio of zeaxanthin to lutein compared to the wild type.

In a further embodiment, to prepare a keto-carotenoid, an expression module for *C. reinhardtii* beta-carotene ketolase1 (CrBKT1) SEQ ID NO: 4, was introduced into the pPB0038 backbone to produce construct pPB0123, which targeted the LCYE-2 single allele. Alternatively, strains in which LCYE alleles were disrupted were prepared. In addition, when a single LCYE allele is knocked out, 4-keto-lutein and astaxanthin are produced, while when both LCYE alleles are knocked out strains almost exclusively produced astaxanthin.

In a specific embodiment of the present invention, to obtain squalene, ApSQE-2 encoding the Squalene Epoxidase allele 2 in *Auxenochlorella prototheocoides* PB5 is knocked out. DNA construct having a transforming DNA with the nucleotide sequence of SEQ ID NO: 7 pPB0065 was prepared and introduced into wild-type *Auxenochlorella prototheocoides* PB5 to prepare strain 65-4. Then, in order to generate a double knockout strain, pPB0077, a DNA construct having nucleotide sequence SEQ ID NO: 8 was constructed and transformed into the strain 65-4 in which SQE-1 encoding Squalene Epoxidase allele 1 was knocked out. The prepared mutant strain was named strain 77B-21.

It was confirmed that the above strains can accumulate squalene while the wild type cannot.

In a specific embodiment of the present invention, the native FAD3 promoter in *A. prototheocoides* PB5 is replaced with a promoter of a gene that is strongly up-regulated during lipid production, thereby activating the endogenous FAD3 gene encoding Fatty acid Desaturase 3 to reduce the ratio of omega-6 to omega-3 compared to the wild type.

Specifically, construct pPB0039 having a transforming DNA with the nucleotide sequence of SEQ ID NO: 13 was constructed in which the ApSAD2 promoter was inserted upstream of the FAD3-1 coding sequence. Alternatively, construct pPB0041 was constructed, in which the native FAD3 promoter was replaced with the promoter of the FATA gene encoding acyl-ACP thioesterase SEQ ID NO: 14. Plasmid construct pPB0039 and pPB0041 were introduced into wild-type *A. prototheocoides* PB5 to obtain strains 39-1 and 39-9 strains 41-1 and 41-3, respectively. It was confirmed that the strains increased the ratio of omega 3 to omega 6 compared to the wild type.

In a specific embodiment of the present invention, transfer of C18:1 between DAG and phospholipids was improved by transforming a construct, pPB0118 SEQ ID NO:15, encoding Arabidopsis phosphatidylchloline:diacylglycerol choline phosphotransferase (PDCT) into strain 41-3. As a result, C18:2 accumulation increased by 2.5-fold in strains 118B-8 and 118B-20, indicating that expression of AtPDCT during lipid production caused significant enhancement of FAD2 activity, and the incorporation of C18:2 into TAG was favored over desaturation by FAD3.

In a specific embodiment of the present invention, the accumulation of fatty acids C18:3 (ALA) was increased by the introduction of a construct, pPB0142 SEQ ID: NO:16, encoding heterologous (*Linum usitatissimum*) FAD3A into strain 118B-8. As a result, ALA accumulation increased about 3% in strain 142B-11.

*Auxenochlorella prototheocoides* PB5 is a superior system for generating engineered microalgae strains due to its ease of transformation and facile homologous recombination that does not require riboprotein-mediated gene editing. PB5 has a higher intrinsic capacity than non-photosynthetic heterotrophic platforms for production of carotenoids and other terpenoids due to the high flux through these biosynthetic pathways during photosynthetic growth.

The Mutants of the present invention are more industrially useful in that they may provide oils having fatty acids, carotenoids, and squalene content of a profile different from that produced in wild-type *Auxenochlorella prototheocoides*.

In some cases, the percent (w/w) of zeaxanthin in the carotenoids produced by using the microalgal mutants of the present invention is 2-3-fold higher compared to the wild-type microalgae and the zeaxanthin is present as a major carotenoid. In a specific embodiment, the percent of zeaxanthin produced ranges between 40 to 90% (w/w) of the total identified carotenoids.

In some cases, the oil produced may contain keto carotenoids, such as the mixture of keto lutein, and astaxanthin, and the astaxanthin is present as a major carotenoid. In a specific embodiment, the percent of keto carotenoids produced ranges between 20-90% (w/w) of the total identified carotenoids.

In some cases, the oil produced may contain squalene. In a specific embodiment, the amount of squalene in the oil produced ranges from 300 to 1300 ppm.

In some cases, the weight ratio of omega-6 to omega-3 in the oil produced by using the microalgal mutants of the present invention is low compared to the oil produced from wild-type microalgae which are 7:1. In a specific embodiment the percent ratio of omega-6 to omega-3 in the oil produced ranges from 1:1 to 5:1.

The mutant of the present invention may grow appropriately in a growth environment (light conditions, temperature conditions, medium, etc.) capable of culturing conventional *Auxenochlorella prototheocoides*.

The mutant of the present invention may be cultured according to the culture conditions of general *Auxenochlorella protothecoides*, and specifically, a culture medium capable of culturing algae under weak light conditions may be used. To culture a specific microorganism, it may include a nutrient material required for a culture target, that is, a microorganism to be cultured, and maybe mixed by adding material for a special purpose. The medium includes an all-natural medium, synthetic medium, or selective medium. The *Auxenochlorella protothecoides* mutant may be cultured according to a conventional culture method.

The pH of the culture medium is not particularly limited if the Auxenochlorella protothecoides may survive and grow, for example, it is viable at pH 5 or higher, specifically at pH 6 to 8.

The *Auxenochlorella protothecoides* mutant of the present invention may produce modified profiles of fatty acids, carotenoids, and terpenoids in cells, so that oils extracted from mutants of the present invention may be effectively used as raw materials for pharmaceuticals, cosmetics, food, feed, etc.

In this aspect, the present invention provides a composition comprising the oil derived from the *Auxenochlorella protothecoides* mutant. The composition may be a cosmetic composition, a food composition, a composition for a food additive, a feed composition, a composition for a feed additive, a pharmaceutical composition, a raw material composition for food, a raw material composition for feed, a raw material composition for pharmaceutics or a raw material composition for cosmetics.

The composition may be used as a raw material for food, feed or pharmaceutics, and may be used as a formulation for oral administration or parenteral administration. For example, it may be used as a formulation for oral, transdermal or injection administration. Accordingly, the composition of the present invention may be a composition for oral administration in that the composition may be orally supplied to be included in food, medicine, or feed.

In the case of compositions for oral administration may be formulated as powders, granules, tablets, pills, dragees, capsules, liquids, gels, syrups, slurries, suspensions, etc. by using methods known in the art. For example, oral preparations may be obtained by mixing the active ingredient with excipients, grinding the mixture, adding suitable additives, and processing it into a granule mixture to obtain tablets or sugar tablets. Examples of suitable excipients include sugars, including lactose, dextrose, sucrose, sorbitol, mannitol, xylitol, erythritol and maltitol, and starches, including corn starch, wheat starch, rice starch and potato starch, cellulose, including methylcellulose, sodium carboxymethylcellulose, and hydroxypropylmethyl-cellulose, and the like, fillers such as gelatin, polyvinylpyrrolidone, and the like may be included. In addition, cross-linked polyvinylpyrrolidone, agar, alginic acid, or sodium alginate may be added as a disintegrant if necessary.

The composition may be used for human and animal health promotion. Specifically, the mutant of the present invention has oil production ability with enhanced antioxidant pigment content, so it is not easily oxidized, and functionally, it is possible to provide an oil superior to conventional microalgae-derived vegetable oil in antioxidant activity, and it can be effectively used as a raw material for health functional food, feed, or medicine.

In addition, since the composition may be added to food or feed to achieve a special purpose use, in this respect it may be a food composition, a composition for food additives, a feed composition or a composition for feed additives. When the composition is used in feed or food, it is possible to maintain or enhance body health by pigments and lipids including zeaxanthin produced by the mutant and accumulated in cells.

In the present invention, "additive" is included as long as it is a material added to food or feed other than the main raw material, and specifically, it may be an effective active material having functionality in food or feed.

In the present invention, the composition for feed may be prepared in the form of fermented feed, compounded feed, pellet form, and silage. The fermented feed may include a functional oil derived from the mutant of the present invention, and additionally include various microorganisms or enzymes.

The composition is mixed with a carrier commonly used in the food or pharmaceutical field, such as tablets, troches, capsules, elixirs, syrups, powders It can be prepared and administered in the form of powder, suspension, or granules. As the carrier, binders, lubricants, disintegrants, excipients, solubilizers, dispersants, stabilizers, suspending agents, and the like may be used. The administration method may be an oral, or parenteral method, but preferably oral administration. In addition, the dosage may be appropriately selected according to the absorption of the active ingredient in the body, the inactivation rate and excretion rate, the age, sex, condition of the subject, and the like. The pH of the composition can be easily changed according to the manufacturing conditions of the drug, food, cosmetics, etc. in which the composition is used.

The composition may include 0.001 to 99.99% by weight, preferably 0.1 to 99% by weight of any one selected from the group consisting of the microalgal mutants of the present invention, the culture of the mutants, the dried product of the mutant, or the culture thereof, and the extract of the mutant or the culture thereof, and the functional oil derived from the mutant, based on the total weight of the composition, and the method of using the composition and the content of the active ingredient may be appropriately adjusted according to the purpose of use.

The mutant may be included in the composition in its own or dried form, and the culture of the mutant may be included in the composition in a concentrated or dried form. In addition, the dried product refers to the dried form of the mutant or its culture and maybe in the form of a powder prepared by freeze-drying or the like.

In addition, the extract means that obtained by extraction from the mutant of the present invention, its culture medium or its dried product, an extract using a solvent, etc. Thus, the mutant of the present invention includes those obtained by crushing the mutant of the present invention. Specifically, the oil with the modified profile accumulated in the cells of the mutant of the present invention may be extracted and separated by a physical or chemical method.

In addition, the method for producing oil with the modified profile according to the present invention may include culturing the mutant of the present invention. In addition, the production method may further include; after the culturing step, isolating the mutant of the present invention from the culture.

The culture may be performed in a medium of pH 5.0 to 8.0 conditions. In addition, it may be carried out under a weak light condition, specifically, a light intensity condition in the range of 0.1-1, 1-3, or 3-5 $\mu$mol photons/$m^2$ s.

The production method may further include, in addition to the culturing step, a concentration step to increase the content of algae after culturing, and a drying step of drying by further reducing the moisture of the algae that has undergone the concentration step. However, the concentration step or the drying step is not necessarily required, and in general, the concentration and drying method commonly used in the field to which the present invention pertains, and it can be carried out using a machine.

The production method may further include the step of purifying the material isolated from the culture, which may be performed by a conventional purification method in the art to which the present invention pertains.

DETAILED DESCRIPTION OF THE EMBODIMENTS

Hereinafter, the present invention will be explained in detail through Examples and Experimental Examples, but these Examples and Experimental Examples are presented only as of the illustration of the present invention, and the scope of the present invention is not limited thereby.

The oleaginous Trebouxiophyte alga, *Auxenochlorella protothecoides*, stores copious amounts of triacylglyceride oil under conditions where the nutritional carbon supply is in excess, but cell division is inhibited due to the limitation of other essential nutrients. Heterotrophically grown *Auxenochlorella* strains also degrade chlorophyll and down-regulate photosynthesis but maintain significant levels of the yellow carotenoids lutein and zeaxanthin. Bulk biosynthesis of fatty acids with carbon chain lengths up to C18 occurs in the plastids; fatty acids are then exported to the endoplasmic reticulum where incorporation into triacylglycerides (TAGs) occurs. Lipids are stored in large cytoplasmic organelles called lipid bodies until environmental conditions change to favor growth, whereupon they are rapidly mobilized to provide energy and carbon molecules for anabolic metabolism. Wild-type *A. protothecoides* storage lipid is comprised mainly of oleic (~68%), palmitic (~12%), and linoleic (~13%) acids, with minor amounts of stearic, myristic, α-linolenic, and palmitoleic acids. This fatty acid profile results from the relative activities and substrate affinities of the enzymes of the endogenous fatty acid biosynthetic pathway. *A. protothecoides* is amenable to manipulation of fatty acid and lipid biosynthesis using molecular genetic tools, enabling the production of oils with fatty acid profiles that are very different from the wild-type composition. Similarly, the carotenoid and phytosterol profile of the lipid fraction can be altered by genetic engineering of terpenoid biosynthesis pathways.

We have demonstrated efficient transformation and facile nuclear gene targeting via homologous recombination in *A. protothecoides*, PB5. In the following examples, we leverage our ability to perform gene knockouts and knock-ins to produce algal oils with modified fatty acid, carotenoid, and terpenoid profiles.

Wild type *A. protothecoides* PB5 was obtained from the University of Texas Culture Collection of Algae (UTEX catalog number 250), and it is available to the public to purchase via webpage www.utex.org.

Example 1. Production of Strains with Altered Carotenoid Profiles

Lutein is the predominant carotenoid that accumulates in heterotrophic *A. protothecoides* cells. To alter the ratio of lutein (derived from alpha-carotene) to zeaxanthin (derived from beta-carotene) we made a DNA construct to disrupt LCYE-1, encoding one allele of lycopene cyclase epsilon in *A. protothecoides* PB5. In general, flanking regions, promoters, and terminator sequences were PCR amplified from PB5 genomic DNA, and codon-optimized synthetic genes were amplified from plasmid DNA. Herculase II Fusion Enzyme (Agilent, USA) was used for PCR amplification. 50 ml amplification reactions contained 100-500 ng genomic DNA template, 250 micromolar dNTPs, 0.25 micromolar primers, and 0.5 ml Herculase II fusion DNA polymerase. Initial denaturation was at 95° C. for 2 minutes or at 98° C. for 4 minutes for highly GC-enriched templates. PCR products were amplified using 30-35 cycles of 95° C. or 98° C., 20 seconds, 55-65° C. annealing for 20 seconds, and extension at 72° C. for 30 seconds per kb. The sequence of the transforming DNA from the LCYE-1 disruption construct pPB0014 is shown below in FIG. 2.

Relevant restriction sites used to generate linear DNA and for cloning are indicated in lowercase, bold, and are from 5'-3' HindIII, KpnI, SalI, and HindIII. Underlined sequences at the 5' and 3' flanks of the construct represent genomic DNA from *A. protothecoides* PB5 that enable targeted integration of the transforming DNA via homologous recombination at the LCYE-1 locus. Proceeding in the 5' to 3' direction, the *Chlamydomonas reinhardtii* TUB2 promoter (CrTUB2) driving the expression of the *Saccharomyces cerevisiae* SUC2 gene (ScSUC2, codon-optimized for expression in *A. protothecoides* and encoding sucrose invertase, thereby enabling the strain to utilize exogenous sucrose) is indicated by lowercase, boxed text. The initiator ATG and terminator TGA for ScSUC2 are indicated by uppercase italics, while the coding region is indicated with lowercase italics. The terminator region of the *A. protothecoides* enolase gene (ApPGH) gene is indicated by small capitals.

Construct pPB0014 was introduced into *A. protothecoides* PB5 using a modified lithium acetate transformation procedure. Briefly, 50 mL of seed growth medium containing 2% glucose in 250 mL Erlenmeyer flask was inoculated with a loop of cells from a plate. Cultures were grown for 2 days at room temperature on an orbital shaker at 140 rpm, to an OD 750 nm 2-4. 50 ml of cell culture was harvested in a Falcon tube and centrifuged for 5 minutes at 3750 rpm. The cell pellet was washed once with 5 ml wash solution (0.1M Lithium acetate (LiAc) and 1× TE (10 mM Tris, 0.1 mM EDTA) buffer and centrifuged to discard the supernatant. The cells were resuspended in 500 μl wash solution, transferred to a sterile Eppendorf tube, and incubated for 1 hour on a rotary shaker at room temperature at 150 rpm. For each transformation, 150 μl of cell suspension was aliquoted into a 1.5 ml Eppendorf tube. 5-20 μg of linearized DNA was added to the cell suspension, then incubated for 30 minutes at room temperature at 150 rpm. 750 μl of PEG solution (0.1M LiAc, 1× TE, 40% PEG-4000) was added to the Eppendorf tube, and transformations were incubated overnight on the shaker at room temperature at 150 rpm. Cells were harvested by centrifugation at 5000 rpm for 30 seconds and resuspended in 250 μl of 1M sorbitol. About 180 μl of the transformation was spread on growth media plates with 1.5% agar with selection, using glass beads, and incubated at room temperature for 1 to 2 weeks. Single colonies were observed on the agar plate after 5-6 days of plating.

Primary transformants were selected for heterotrophic growth on media with sucrose as the sole carbon source. Colonies were clonally purified, and integration of pPB0014 at the LCYE-1 locus was verified for 11 strains by PCR amplification of the regions flanking the 5' and 3' ends of the integration site. Strain 14-2 was selected as the parent strain for subsequent modifications. Next, we disrupted LCYE-2, encoding the second allele of lycopene cyclase epsilon, with the goal of generating double knockout strains completely lacking in alpha-carotene-derived carotenoids. The sequence of the transforming DNA from the LCYE-2 disruption construct pPB0038 is shown below in FIG. 3. Relevant restriction sites used to generate linear DNA and for cloning are indicated in lowercase, bold, and are from 5'-3' HindIII, KpnI, SacI, and HindIII. Underlined sequences at the 5' and 3' flanks of the construct represent genomic DNA from *A. protothecoides* that enable targeted integration of the transforming DNA via homologous recombination at the LCYE-2 locus. Proceeding in the 5' to 3' direction, the *A. protothecoides* HUP1 promoter (ApHUP1) driving the expression of the Arabidopsis thaliana THIC gene (AtTHIC, codon-optimized for expression in *A. protothecoides* and encoding 4-amino-5-hydroxymethyl-2-methylpyrimidine synthase activity, thereby permitting the strain to grow in the absence of exogenous thiamine) is indicated by lowercase, boxed text. The initiator ATG and terminator TGA for AtTHIC are indicated by uppercase italics, while the coding region is indicated with lowercase italics. The terminator region of the *A. protothecoides* heat shock protein 90 (ApHSP90) gene is indicated by small capitals.

Construct pPB0038 was transformed into LCYE-1 disruption strain 14-2. Primary transformants were selected for heterotrophic growth on media without thiamine, and with sucrose as the sole carbon source. Colonies were clonally purified, and double knockout of both LCYE-1 and LCYE-2 was verified in strain 38-25 by PCR amplification of the regions flanking the 5' and 3' ends of the pPB0014 and pPB0038 integrations. Spectrophotometric, and HPLC analysis of carotenoid pigments from wild-type *A. protothecoides* PB5, 14-2, and 38-25 is shown in FIG. 4A and B. Pigments for spectrophotometric analysis were extracted by mechanical disruption of cell pellets mixed with 0.5 mm glass beads (BioSpec Products, Inc.) suspended in 80:20 acetone:methanol, using a Mini-Beadbeater-16 (BioSpec Products, Inc.). Absorption spectra were acquired using a Thermo Scientific GeneSys 10uv spectrophotometer. Lutein is the predominant pigment extracted from the wild-type strain. Reduction of lycopene cyclase epsilon activity by disrupting the LCYE-1 allele in 14-2 increases the ratio of zeaxanthin to lutein. Lutein accumulation is abolished in the 38-25 double knockout strain, and zeaxanthin is the major carotenoid.

Cell cultivation—Cells were grown in a growth medium composed of the following chemicals in 1 L deionized water. 0.025 g NaCl, 0.25 g NaNO$_3$, 0.074 g MgSO$_4$·7H$_2$O, 0.025 g CaCl$_2$·2H$_2$O, 0.075 g K$_2$HPO$_4$, 0.176 g KH$_2$PO$_4$, 2.38 g HEPES, 3 g Yeast extract, 5 ml stock vitamin solutions, and 20 g glucose. pH was adjusted to 6.8 with 20% NaOH. Stock vitamin solution contained the following in 200 ml HEPES solution (50 mM HEPES, pH7.8); 0.005 g Biotin, 0.44 g Thiamine HCl, 0.027 g B12, and 0.619 g D-Pantothenic acid hemicalcium. The stock vitamin solution was filtered, sterilized, and stored at 4° C. refrigerator.

Seed flask cultivation—in 250 ml Erlenmeyer flask containing 95 ml growth medium and 5 ml 40% stock glucose solution, loopful of cells were inoculated from the agar plate and grown for 2 days on an orbital shaker at 115 rpm at 28° C. under 0.1-1 µmol photons/m$^2$ s low intensity LED light.

Main flask cultivation—in 1 L Erlenmeyer flask containing 332.5 ml growth medium and 17.5 ml 40% stock glucose solution, inoculate cells from seed flask so that initial optical density (OD) at 750 nm wavelength was 0.5-0.6. Incubate the flask on the orbital shaker under 0.1-1 µmol photons/m$^2$ s low intensity LED light at 115 rpm at 28° C. for 4-5 days until all glucose is exhausted. Harvest the cells via centrifugation and freeze dry the cell pellet. Store the freeze-dried cell pellet at −20° C. freezer.

The lipid extraction method and HPLC parameters are described below.

About 3-5 g lyophilized PB5 and modified strain cell powders were finely ground in a mortar using a pestle. 30 ml of ether was added to the milled microalga powders then vortexed for about 30 seconds to extract oil and carotenoids. 30 ml of additional ether was used if necessary to complete the extraction of all the oil and carotenoids. The remaining ether was evaporated using an evaporator at room temperature. The extracted oil was dissolved and diluted at a 1:10 ratio with a mixed Hexane:Ethyl Acetate (70:30, v/v) solvent. 10 µl of the diluted solution was injected into an HPLC (Agilent 1260 Infinity II, Agilent, USA) and separation of analytes was conducted on a Luna silica 100A column (25 cm×4.6 mm; 5 µm, Phenomenex, USA). The mobile phase consisted of hexane: ethyl acetate (70:30, v/v) at a flow rate of 1.5 ml/min. The column temperature was set at 30° C. and lutein, zeaxanthin, and standards were detected at 446 nm. The lutein standard eluted at a retention time of 12.6 minutes and the zeaxanthin standard eluted at a retention time of 13.5 minutes. Table 1 summarized the results of carotenoid analysis of each genetically modified strain and wild-type strain PB5 (control).

TABLE 1

| Carotenoids identified in extracted oil from PB5 and modified strains via HPLC. | | | |
|---|---|---|---|
| Strains | Carotenoids | Retention time | Percent (%) |
| PB5 (Control) | Lutein | 12.689 | 67.0392 |
| | Zeaxanthin | 13.548 | 27.9272 |
| 14-2 | Lutein | 12.685 | 50.1228 |
| | Zeaxanthin | 13.55 | 45.4815 |
| 38-25 | Zeaxanthin | 13.554 | 87.8917 |

Next, we sought to express beta-carotene ketolase activity in *A. protothecoides* cells, allowing them to make keto-carotenoids with high value as antioxidants. To achieve this, we introduced an expression module for the *C. reinhardtii* beta-carotene ketolase gene 1 (CrBKT1) into the pPB0038 backbone. The sequence of the expression module cloned into the KpnI site of pPB0038 to generate construct pPB0120 is shown below in FIG. 5. KpnI and SpeI sites flanking the expression module and used for cloning are indicated in lowercase, bold. Proceeding in the 5' to 3' direction, the *A. protothecoides* SAD2 promoter (ApSAD2) driving the expression of the CrBKT1 gene is indicated by lowercase, boxed text. The initiator ATG and terminator TGA for CrBKT1 are indicated by uppercase italics, while the coding region is indicated with lowercase italics. The sequence encoding the predicted plastid transit peptide is underlined. The terminator region of *A. protothecoides* SAD2 is indicated by small capitals.

We considered that the heterologous CrBKT1 protein might not be imported efficiently into *Auxenochlorella* plastids, so we also made a version of the CrBKT1 expression module that replaced the sequence encoding the native plastid transit peptide with the corresponding sequence from the endogenous Auxenochlorella SAD2 gene. The sequence of the chimeric ApSAD2tp_CrBKT1 coding sequence in construct pPB0123 is shown below in FIG. 6. pPB0123 was otherwise identical to pPB0120 and targeted the AtTHIC transformation marker and the CrBKT1 expression module to the LCYE-2 locus. The sequences of the native CrBKT1 protein and the ApSAD2tp_CrBKT1 chimeric proteins are shown in FIGS. 7A and 7B, respectively.

Constructs pPB0120 and pPB0123 were both transformed into wild-type *A. protothecoides*PB5 to make LCYE-2 single allele knockouts expressing CrBKT1, and into LCYE-1 disruption strain 14-2 to make LCYE double knockouts expressing CrBKT1. Primary transformants made in the wild-type *A. protothecoides* background were selected for heterotrophic growth on glucose-containing media without thiamine, while transformants generated in the 14-2 parent strain were selected on media without thiamine, supplemented with sucrose. Primary transformants were clonally purified and shake flask cultures of representative strains are shown in FIG. 8A. Strains transformed with pPB0123, expressing chimeric ApSAD2tp_CrBKT1 produced more red-colored ketocarotenoids than pPB0120 transformants that expressed native CrBKT1, suggesting that the chimeric protein was imported and processed more efficiently than the native protein. HPLC analysis, shown in FIG. 8B, showed that the predominant ketocarotenoids in LCYE-2 single allele knockouts (A strains, wild-type *A. protothecoides* parent) were 4-keto-lutein and astaxanthin, derived from lutein and zeaxanthin, respectively. The strains that expressed CrBKT1 with both LCYE alleles disrupted (B strains) made astaxanthin almost exclusively.

The lipid extraction method and HPLC parameters for keto-carotenoids analysis-Ether extraction of oil and carotenoids was performed as described above. The extracted oil was dissolved and diluted at a 1:100 ratio with a solvent mixture of Hexane:Acetone (82:18, v/v). 20 μl of the diluted solution was injected into an HPLC (Agilent 1260 Infinity II, Agilent, USA) and separation of analytes was conducted on a Luna silica column (15 cm×4.6 mm; 3 μm, Phenomenex, USA). The mobile phase consisted of Hexane:Acetone (82:18, v/v) ran at a flow rate of 1.2 ml/min. The column temperature was not set and astaxanthin and standards were detected at 474 nm. The astaxanthin standard was eluted at a retention time of 7.6 minutes. Table 2 summarized HPLC analysis results of genetically modified strains producing different carotenoids.

TABLE 2

Carotenoids identified in extracted oil from modified strains via HPLC.

| Strains | Carotenoids | Retention time | Percent (%) |
|---|---|---|---|
| 120A-2 | Astaxanthin | 7.638 | 29.8938 |
| | Keto Lutein | 9.258 | 39.4228 |
| | Lutein | 12.682 | 11.5903 |
| 123A-5 | Astaxanthin | 7.634 | 30.0058 |
| | Keto Lutein | 9.254 | 39.9874 |
| | Lutein | 12.685 | 7.5039 |
| 120B-2 | Astaxanthin | 7.631 | 71.5094 |
| | Zeaxanthin | 13.571 | 3.3719 |
| 123B-24 | Astaxanthin | 7.632 | 77.876 |
| | Zeaxanthin | 13.582 | 2.5516 |

Example 2. Production of Strains with Accumulating Squalene

Squalene is used extensively in cosmetics as an emollient and moisturizer, while its antioxidant properties are exploited in sunscreens and anti-aging products. There are numerous pharmacological applications, including use in formulations as a chemoprotective agent, an anti-bacterial and anti-fungal agent, an adjuvant for vaccines, and a drug carrier. In vivo studies have demonstrated its value as a food supplement with benefits for weight and cholesterol control. Squalene is also a valuable precursor for the chemical synthesis of steroids and other bioactive molecules.

We have enhanced the value of *A. protothecoides*, PB5, storage lipid by engineering strains to accumulate squalene during the lipid production phase by targeted disruption of the squalene epoxidase (SQE) gene. Squalene epoxidase catalyzes the squalene cyclization step in phytosterol biosynthesis. Knockout of the equivalent ERG1 gene in *S. cerevisiae* led to squalene accumulation. Similar metabolic engineering strategies have been applied in cyanobacteria and purple non-sulfur bacteria, and elevated squalene levels were observed in *C. reinhardtii* strains where RNAi was used to knock-down SQE gene expression. In this example, we describe genetically engineered *A. protothecoides*, PB5 strains in which we have disrupted both alleles of SQE. These modifications block downstream phytosterol biosynthesis and cause the accumulation of squalene in cellular lipids. The sequence of the transforming construct pPB0065, targeting disruption of ApSQE-2 is provided in FIG. 9. Restriction sites are indicated with bold, lowercase text. HindIII sites delimit the 5' and 3' ends of the transforming DNA. EcoRI and SacI sites flank the selection cassette. Underlined sequences represent SQE-2 genomic DNA targeting integration at the SQE-2 locus via homologous recombination. Proceeding from 5' to 3', the selection cassette contains the ApHUP1 promoter (lowercase, boxed text), driving the expression of codon-optimized AtTHIC. The initiator ATG and terminator TGA for AtTHIC are indicated by uppercase italics, while the coding region is indicated with lowercase italics. The ApHSP90 terminator region is indicated by small capitals.

SQE-2 knockout strains were generated by transformation of pPB0065 into *A. protothecoides* PB5. Primary transformants were selected on glucose-containing growth media without thiamine. Colonies were clonally purified, and targeted disruption of SQE-2 was verified by PCR amplification and sequencing of the regions flanking the integration site. Transformant 65-4 was selected as the parent strain for subsequent transformation with construct pPB0077, targeting ApSQE-1. The sequence of the transforming DNA from pPB0077 is shown below in FIG. 10. Restriction sites are indicated with bold, lowercase text. HindIII sites delimit the 5' and 3' ends of the transforming DNA. EcoRI and SacI sites flank the selection cassette. Underlined sequences represent ApSQE-1 genomic DNA targeting integration at the ApSQE-1 allele via homologous recombination. Proceeding from 5' to 3', the selection cassette contains the CrTUB2 promoter (lowercase, boxed text), driving the expression of codon-optimized ScSUC2. The initiator ATG and terminator TGA for ScSUC2 are indicated by uppercase italics, while the coding region is indicated with lowercase italics. The ApPGH terminator region is indicated by small capitals.

Primary transformants from the introduction of pPB0077 into strain 65-4 were selected on growth media with sucrose and without thiamine. Colonies were clonally purified and targeted disruption of both ApSQE-1 and ApSQE-2 was verified by PCR amplification and sequencing of the regions flanking the integration site.

A representative strain, 77B-21, was grown in lipid production media and the squalene content of crude lipid extracts was measured by HPLC (FIG. 11).

Cell cultivation conditions—Cells were grown in a growth medium containing the followings in 1 L deionized water: 4.2 g $K_2HPO_4$, 3.57 g $NaH_2PO_4 \cdot H_2O$, 0.24 g $MgSO_4 \cdot 7H_2O$, 0.025 g $CaCl_2 \cdot 2H_2O$, 0.25 g citric acid, 2 micromolar thiamine-HCl, and 10 mL of trace metal solution. 1 L of trace metal solution contained 2.75 g citric acid, 0.011 g $CuSO_4 \cdot 5H_2O$, 0.081 g $CoCl_2 \cdot 6H_2O$, 0.33 g $H_3BO_3$, 1.4 g $ZnSO_4 \cdot 7H_2O$, 0.9485 g $MnCl_2 \cdot 4H_2O$, 0.039 g $Na_2MoO_4 \cdot 2H_2O$, 0.11 g $FeSO_4 \cdot 7H_2O$, 0.0144 g $NiSO_4 \cdot 6H_2O$. Pre-seed and seed medium contained 0.991 g/L of $(NH_4)_2SO_4$, and lipid production media contained 0.248 g of $(NH_4)_2SO_4$. The pre-seed medium was supplemented with 5 g/L glucose; seed medium contained 20 g/L glucose and lipid production contained 40 g/L glucose.

The lipid extraction method and HPLC parameters for squalene analysis—About 3 g of lyophilized PB5 and modified strain cell powders were finely ground in a mortar using a pestle. 30 ml of ether was added to the ground PB5 powder and the resulting suspension was vortexed for about 30 seconds to extract oil. An additional 30 ml of ether was used to complete oil extraction. The remaining ether was evaporated at room temperature using an evaporator. The extracted oil was dissolved and diluted at a 1:10 ratio with a solvent mixture solvent of Acetonitrile:Methanol (8:2, v/v), which was also used as the mobile phase. 30 μl of the diluted solution was injected into an HPLC (Agilent 1260 Infinity II) and separation of analytes was conducted on a C18 reverse column (15 cm×4.6 mm; Shiseido, Japan). The mobile phase's flow rate was 1.5ml/min. The column temperature was set at 35° C. and squalene and the standard was detected at 195 nm. Squalene standard eluted at a retention time of 18.090.

Squalene accumulated to 1222 ppm in oil from strain 77B-21, a level that is on par with the squalene content of olive oil, a common commercial source.

The value of *A. protothecoides* oil would be enhanced by further increases in squalene levels. This may be achieved through overexpression of key enzymes in the isoprenoid biosynthesis pathway to increase flux. The amino acid sequences of *A. protothecoides* 1-deoxy-D-xylulose 5-phosphate synthase (DXS), 1-deoxy-D-xylulose 5-phosphate reductoisomerase (DXR), farnesyl diphosphate synthase (FDPS), and squalene synthase are provided in FIGS. 12-15. Overexpression of the native *A. protothecoides* enzymes, or of heterologous enzymes from plants or other algae, in the SQE double knockout background may improve squalene accumulation.

Example 3. Production of Strains with Increased Levels of Omega-3 and Omega-6 Fatty Acids The fatty acid composition of *A. protothecoides* storage lipid is typical for Trebouxiophyte algae, consisting mainly of oleic (~68%), palmitic (~12%), and linoleic (~13%) acids, with minor amounts of stearic, myristic, α-linolenic, and palmitoleic acids. We sought to improve the nutritional quality of *A. protothecoides* triacylglyceride oils by increasing the polyunsaturated fatty acid (PUFA) content. First, we activated the endogenous FAD3 gene, encoding fatty acid desaturase 3, by swapping the native FAD3 promoter with promoters from genes that are strongly upregulated during lipid production. FAD3 introduces a double bond at the Δ15 position of linoleic acid (C18:2) to make α-linolenic acid. The sequence of the transforming construct pPB0039, targeting insertion of the ApSAD2 promoter upstream of the FAD3-1 coding sequence is provided in FIG. 16. Restriction sites are indicated with bold, lowercase text. HindIII sites delimit the 5' and 3' ends of the transforming DNA. KpnI and SpeI sites flank the selection cassette. Underlined sequences represent FAD3-1 genomic DNA targeting integration at the FAD3-1 locus via homologous recombination. Proceeding from 5' to 3', the selection cassette contains the ApHUP1 promoter (lowercase, boxed text), driving the expression of codon-optimized AtTHIC. The initiator ATG and terminator TGA for AtTHIC are indicated by uppercase italics, while the coding region is indicated with lowercase italics. The ApHSP90 terminator region is indicated by small capitals. Lowercase, boxed text delineates the ApSAD2 promoter.

We also made a version of the FAD3 integration construct expression module that replaced the native FAD3 promoter with the promoter from the *A. protothecoides* FATA gene, encoding the acyl-ACP thioesterase. Construct pPB0041 was identical to pPB0039 except that ApFATA promoter shown below in FIG. 17 in lowercase, boxed text, was used to drive the expression of FAD3.

pPB0039 and pPB0041 were transformed into *A. protothecoides* PB5 and primary transformants were selected on glucose-containing growth media without thiamine. Colonies were clonally purified and insertion of the constructs at the FAD3 locus was verified by PCR amplification and sequencing of the regions flanking the integration site.

Cell cultivation conditions-Cells were grown in a growth medium composed of the following chemicals in 1 L of deionized water: 4.2 g $K_2HPO_4$, 3.57 g $NaH_2PO_4 \cdot H_2O$, 0.24 g $MgSO_4 \cdot 7H_2O$, 0.025 g $CaCl_2 \cdot 2H_2O$, 0.25 g citric acid, 2 micromolar thiamine-HCl, and 10 mL of trace metal solution. 1 L of trace metal solution contained 2.75 g citric acid, 0.011 g $CuSO_4 \cdot 5H_2O$, 0.081 g $CoCl_2 \cdot 6H_2O$, 0.33 g $H_3BO_3$, 1.4 g $ZnSO_4 \cdot 7H_2O$, 0.9485 g $MnCl_2 \cdot 4H_2O$, 0.039 g $Na_2MoO_4 \cdot 2H_2O$, 0.11 g $FeSO_4 \cdot 7H_2O$, 0.0144 g $NiSO_4 \cdot 6H_2O$. Pre-seed and seed medium contained 0.991 g/L of $(NH_4)_2SO_4$, and lipid production media contained 0.248 g of $(NH_4)_2SO_4$. The pre-seed medium was supplemented with 5 g/L glucose; seed medium contained 20 g/L glucose and lipid production contained 40 g/L glucose.

Freeze-dried microalgal samples were sent to Microbial ID Inc., (Delaware, USA) for fatty acid methyl ester analysis (FAME). Microbial ID Inc. utilized standardized gas chromatographic analysis of fatty acid methyl esters method developed by MIDI Inc., (Delaware, USA) and the reference could be found in their technical note #101, published and revised in 2006. The fatty acid profiles of lipids from shake flask assays of representative strains are shown in Table 3. Strains driving expression of one allele of FAD3 with the ApSAD2 promoter (39-1 and 39-9 strains) or the ApFATA promoter (41-1 and 41-3 strains) showed a slight increase in α-linolenic acid (ALA, omega-3) from 2% in the wild-type (PB5) to about 3%. The increase in ALA came at the expense of linoleic acid (omega-6), improving the omega-6: omega-3 ratio from 7 to about 4 (lower is better).

TABLE 3

Fatty acid profiles as a percentage of total fatty acids for *A. protothecoides* strains transformed with pPB0039 or pPB0041.

| strain | PB5 | 39-1 | 39-9 | 41-1 | 41-3 |
|---|---|---|---|---|---|
| C14:0 myristic | 1.7 | 1.6 | 1.7 | 1.6 | 1.7 |
| C16:0 palmitic | 12.7 | 13.0 | 12.6 | 12.0 | 12.6 |
| C16:1n-7 palmitoleic | 0.3 | 0.3 | 0.3 | 0.3 | 0.3 |
| C18:0 stearic | 2.5 | 2.5 | 2.6 | 2.4 | 2.3 |
| C18:1n-9 oleic | 66.3 | 68.9 | 67.8 | 68.5 | 67.5 |
| C18:2n-6 linoleic LA | 14.2 | 10.5 | 11.1 | 11.7 | 11.9 |

TABLE 3-continued

| | | | | | |
|---|---|---|---|---|---|
| Fatty acid profiles as a percentage of total fatty acids for A. protothecoides strains transformed with pPB0039 or pPB0041. | | | | | |
| strain | PB5 | 39-1 | 39-9 | 41-1 | 41-3 |
| C18:3n-3 α-linolenic | 2.0 | 2.9 | 3.3 | 3.0 | 3.1 |
| omega-6:omega-3 | 6.9 | 3.6 | 3.4 | 4.0 | 3.9 |
| % PUFA | 16.2 | 13.4 | 14.4 | 14.6 | 15.0 |

The Δ9 double bond in C18:1 is introduced by the stearoyl-ACP desaturases (SADs) in the plastid. Formation of the Δ12 and Δ15 double bonds, catalyzed by FAD2 and FAD3, respectively, occurs in the endoplasmic reticulum, and these enzymes use membrane lipids as their substrate. The relatively low abundance of C18:2 and C18:3 α in wild-type A. protothecoides storage lipid results from the competition between the acyltransferases of the Kennedy pathway for the formation of TAG, and the enzymes of the Lands cycle, which control the exchange of fatty acids between diacylglycerol (DAG) and membrane phospholipids. We considered that increasing the transfer of C18:1 between DAG and phospholipids might improve PUFA production, so we introduced a construct to overexpress Arabidopsis PDCT, encoding phosphatidylchloline:diacylglycerol choline phosphotransferase into strain 41-3. The sequence of the transforming construct pPB0118, targeting AtPDCT and ScSUC2 expression to the THI4 locus is provided in FIG. 18. Restriction sites are indicated with bold, lowercase text. HindIII sites delimit the 5' and 3' ends of the transforming DNA. KpnI, SpeI, and XhoI sites separate the AtPDCT expression module and the ScSUC2 expression cassette. Underlined sequences represent THI4 genomic DNA targeting integration at the THI4 locus via homologous recombination. Proceeding from 5' to 3', the selection cassette contains the ApSAD2 promoter (lowercase, boxed text), driving the expression of codon-optimized AtPDCT. The initiator ATG and terminator TGA for AtPDCT are indicated by uppercase italics, while the coding region is indicated with lowercase italics. The ApSAD2 terminator region is indicated by small capitals. Lowercase, boxed text delineates the CrTUB2 promoter, driving the expression of codon-optimized ScSUC2. The initiator ATG and terminator TGA for ScSUC2 are indicated by uppercase italics, while the coding region is indicated with lowercase italics. The ApPGH terminator region is indicated by small capitals.

pPB0118 was transformed into strain 41-3, and primary transformants were selected on sucrose-containing growth media without thiamine. Colonies were clonally purified and insertion of the constructs at the THI4 locus was verified by PCR amplification and sequencing of the regions flanking the integration site. Freeze-dried microalgal cell samples were sent to Microbial ID inc. (Delaware, USA) for fatty acid methyl ester analysis and the profiles of lipids from shake flask assays of representative strains containing the pPB0118 construct are shown in Table 4. C18:2 accumulation increased by 2.5-fold in strains 118B-8 and 118B-20, indicating that expression of AtPDCT during lipid production caused significant enhancement of FAD2 activity. ALA levels only increased by about 1% compared to the 41-3 parent strain, suggesting that incorporation of C18:2 into TAG was favored over desaturation by FAD3. The omega-6: omega-3 ratio increased from 3.8 in 41-3 to above 8, due to the increase in C18:2 without a concomitant increase in ALA.

TABLE 4

| | | | | |
|---|---|---|---|---|
| Fatty acid profiles as a percentage of total fatty acids for strain 41-3 transformed with pPB0118. | | | | |
| strain | PB5 | 41-3 | 118B-8 | 118B-20 |
| C14:0 myristic | 1.7 | 1.8 | 2.1 | 2.1 |
| C16:0 palmitic | 12.3 | 12.5 | 12.4 | 13.3 |
| C16:1n-7 palmitoleic | 0.3 | 0.3 | 0.3 | 0.4 |
| C18:0 stearic | 2.4 | 2.3 | 1.8 | 2.2 |
| C18:1n-9 oleic | 67.9 | 67.5 | 45.4 | 46.4 |
| C18:2n-6 linoleic LA | 13.1 | 12.0 | 33.3 | 30.8 |
| C18:3n-3 α-linolenic | 1.8 | 3.1 | 4.0 | 3.9 |
| omega-6:omega-3 | 7.2 | 3.8 | 8.3 | 8.0 |
| % PUFA | 15.0 | 15.1 | 37.3 | 34.7 |

Upregulation of the endogenous FAD3 gene and overexpression of AtPDCT only resulted in small improvements in ALA accumulation, so we tested whether ALA biosynthesis could be further improved by the expression of heterologous FAD3. We chose to test FAD3A from *Linum usitatissimum* (flax), which has been shown previously to have desaturase activity in *Prototheca moriformis*. The sequence of the transforming construct pPB0142, targeting LuFAD3A and neoR expression to the THI4 locus is provided in FIG. 19. Restriction sites are indicated with bold, lowercase text. HindIII sites delimit the 5' and 3' ends of the transforming DNA. KpnI, SpeI, and BamHI sites separate the LuFADA expression module and the neoR expression cassette. Underlined sequences represent THI4 genomic DNA targeting integration at the THI4 locus via homologous recombination. Proceeding from 5' to 3', the selection cassette contains the ApSAD2 promoter (lowercase, boxed text), driving the expression of codon-optimized LuFAD3A. The initiator ATG and terminator TGA for LuFAD3A are indicated by uppercase italics, while the coding region is indicated with lowercase italics. The ApFBA1 terminator region is indicated by small capitals. Lowercase, boxed text delineates the ApPGK1 promoter, driving the expression of codon-optimized neoR, which confers resistance to the antibiotic G418. The initiator ATG and terminator TGA for neoR are indicated by uppercase italics, while the coding region is indicated with lowercase italics. The ApPGK1 terminator region is indicated by small capitals.

pPB0142 was transformed into strain 118B-8, and primary transformants were selected on G418-containing growth media supplemented with sucrose and without thiamine. Colonies were clonally purified and insertion of the constructs at the THI4 locus was verified by PCR amplification and sequencing of the regions flanking the integration site. We also verified that strains containing both constructs pPB0118 and pPB0142 disrupted both alleles of the THI4 locus, rendering them unable to grow without supplementation with hydroxymethyl thiazole (FIG. 20).

As shown in FIG. 20, Thiamine prototrophy is observed in strain 118B-8, expressing AtTHIC, targeted to one allele of THI4. Disruption of the second THI4 allele by pPB0142 renders the transformants thiazole auxotrophs.

Freeze-dried microalgal cell pellets were sent to Microbial ID (Delaware, USA) for fatty acid methyl ester analysis (FAME) and the profiles of lipids from shake flask assays of representative strains containing the pPB0142 construct are shown in Table 5. ALA accumulation increased from 5.4% in the 118B-8 parent to up to 8.7% in strain 142B-11, indicating that expression of LuFAD3A during lipid production enhanced desaturation of C18:2. The omega-6: omega-3 ratio was reduced to 4, similar to the original ratio observed in the parent strain 41-3 (see Table 4), but with a 5-fold increase in omega-3 fatty acids and a 3-fold improvement in overall PUFA compared to the wild-type strain.

TABLE 5

Fatty acid profiles as a percentage of total fatty acids for strain 118B-8 transformed with pPB0142.

| strain | PB5 | 118B-8 | 142B-8 | 142B-11 |
| --- | --- | --- | --- | --- |
| C14:0 myristic | 2.0 | 2.5 | 2.3 | 2.2 |
| C16:0 palmitic | 12.0 | 11.8 | 12.5 | 12.0 |
| C16:1n-7 palmitoleic | 0.4 | 0.3 | 0.4 | 0.4 |
| C18:0 stearic | 2.5 | 1.8 | 1.9 | 1.8 |
| C18:1n-9 oleic | 67.9 | 44.1 | 39.9 | 39.2 |
| C18:2n-6 linoleic LA | 13.5 | 34.0 | 34.4 | 34.6 |
| C18:3n-3 α-linolenic | 1.8 | 5.4 | 8.2 | 8.7 |
| omega-6:omega-3 | 7.6 | 6.3 | 4.2 | 4.0 |
| % PUFA | 15.3 | 39.4 | 42.6 | 43.3 |

We aim to produce a nutritionally superior oil from *A. protothecoides* PB5, with very low saturates and a 1:1 ratio of omega-6: omega-3 fatty acids. Optimization of C18:2 and C18:3 α levels may be achieved by modulating the expression of AtPDCT and LuFAD3A. The main saturated fatty acids in wild-type *A. protothecoides* oil are C14:0, C16:0, and C18:0 (see Tables 3, 4 & 5). Levels of C14:0 and C16:0 can be reduced by over-expressing the native KASII gene, encoding beta-ketoacyl-ACP synthase II, which extends C16:0 to C18:0. The coding sequence of the *Auxenochlorella* KASII gene, optimized for translation, is shown in FIG. 21 and the corresponding amino acid sequence is detailed in FIG. 22.

REFERENCES

1. Single cell oils. (AOCS Press, 2010).
2. Zaimes, G. G. & Khanna, V. Environmental sustainability of emerging algal biofuels: A comparative life cycle evaluation of algal biodiesel and renewable diesel. Environ. Prog. Sustain. Energy 32, 926-936 (2013).
3. Bhujade, R., Chidambaram, M., Kumar, A. & Sapre, A. Algae to Economically Viable Low-Carbon-Footprint Oil. Annu. Rev. Chem. Biomol. Eng. 8, 335-357 (2017).
4. Huang, Y.-S. & Sinclair, A. Lipids in Infant Nutrition. (AOCS Publishing, 1998). doi:10.1201/9781439831953.
5. Naguib, Y. M. A. Antioxidant Activities of Astaxanthin and Related Carotenoids. J. Agric. Food Chem. 48, 1150-1154 (2000).
6. Schmidt, I. et al. Biotechnological production of astaxanthin with Phaffia rhodozyma/Xanthophyllomyces dendrorhous. Appl. Microbiol. Biotechnol. 89, 555-571 (2011).
7. Elwan, H. a. M., Elnesr, S. S., Abdallah, Y., Hamdy, A. & El-Bogdady, A. H. Red yeast (Phaffia rhodozyma) as a source of Astaxanthin and its impacts on productive performance and physiological responses of poultry. Worlds Poult. Sci. J. 75, 273-284 (2019)
8. Nicolaides, N. (1974). Skin lipids: their biochemical uniqueness. Science 186, 19-26
9. Amarowicz, R. (2009). Squalene: a natural antioxidant? Eur. J. Lipid Sci. Technol. 111, 411-412
10. Günes, F. E. (2013). Medical use of squalene as a natural antioxidant. Clin. Exp. Health Sci. 3, 220-228
11. Kim, S. K., and Karadeniz, F. (2012). "Biological importance and applications of squalene and squalane," in Advances in Food and Nutrition Research, Vol. 65. ed S. K. Kim (Walthum, MA: Academic Press), 223-233
12. Huang, Z. R., Lin, Y. K., and Fang, J. Y. (2009). Biological and pharmacological activities of squalene and related compounds: potential uses in cosmetic dermatology. Molecules 14, 540-554
13. Popa, O., Băbeanu, N. E., Popa, I., Niță, S., and Dinu-Pârvu, C. E. (2015). Methods for obtaining and determination of squalene from natural sources. Biomed. Res. Int. 2015:367/202
14. Aioi, A., Shimizu, T., and Kuriyama, K. (1995). Effect of squalene on superoxide anion generation induced by a skin irritant, lauroylsarcosine. Int. J. Pharm. 113, 159-164
15. Budiyanto, A., Ahmed, N. U., Wu, A., Bito, T., Nikaido, O., Osawa, T., et al. (2000). Protective effect of topically applied olive oil against photocarcinogenesis following UVB exposure of mice. Carcinogenesis 21, 2085-2090
16. Smith, T. J. (2000). Squalene: potential chemopreventive agent. Expert Opin. Invest. Drugs 9, 1841-1848
17. Kopicová, Z., and Vavreinová, S. (2007). Occurrence of squalene and cholesterol in various species of Czech freshwater fish. Czech. J. Food Sci. 25, 195-201
18. Del Giudice, G., Fragapane, E., Bugarini, R., Hora, M., Henriksson, T., Palla, E., et al. (2006). Vaccines with the MF59 adjuvant do not stimulate antibody responses against squalene. Clin. Vaccine Immunol. 13, 1010-1013
19. Pasquale, A. D., Preiss, S., Silva, F. T. D., and Garçon, N. (2015). Vaccine adjuvants: from 1920 to 2015 and beyond. Vaccines 3, 320-343
20. Ivanova, S., Tonchev, V., Yokoi, N., Yappert, M. C., Borchman, D., and Georgiev, G. A. (2015). Surface properties of squalene/meibum films and NMR confirmation of squalene in tears. Int. J. Mol. Sci. 16, 21813-21831
21. Rosales-Garcia, T., Jimenez-Martinez, C., and Dávila-Ortiz, G. (2017). Squalene extraction: Biological sources and extraction methods. Int. J. Environ. Agric. Biotechnol. 2, 1662-1670
22. Global Market Insights (2016). Squalene Market Size by Source, by Application, Industry Analysis Report, Regional Outlook, Application Potential, Price Trends, Competitive Market Share & Forecast, 2015-2022
23. Czaplicki, S., Ogrodowska, D., Zadernowski, R., and Derewiaka, D. (2012). Characteristics of biologically-active substances of amaranth oil obtained by various techniques. Pol. J. Food Nutr. Sci. 62, 235-239
24. Xiao Y, Lu Y, Dai J and Wu Q (2015) Industrial fermentation of Auxenochlorella protothecoides for production of biodiesel and its application in vehicle diesel engines. Front. Bioeng. Biotechnol. 3:164.

What is claimed is:

1. A mutant *Auxenochlorella protothecoides* to produce oil with modified profiles of omega-3 fatty acids, omega-6 fatty acids, lutein, zeaxanthin, astaxanthin, 4-keto-lutein, or squalene, comprising a knock-out of at least one allele of lycopene cyclase epsilon LCYE-1, lycopene cyclase epsilon LYCE-2, squalene epoxidase SQE-1, or squalene epoxidase SQE-2, or a replacement of a native FAD3 promoter by a FATA gene promoter from *Auxenochlorella protothecoides* or a stearoyl-ACP desaturase (SAD2) promoter from *Auxenochlorella protothecoides*.

2. The mutant *Auxenochlorella protothecoides* of claim 1, wherein the mutant *Auxenochlorella protothecoides* is characterized in that one or more of the alleles of exogenous beta-ketolase 1 gene (CrBKT1) is knocked in.

3. An oil produced by the mutant *Auxenochlorella protothecoides* of claim 1.

4. Composition comprising a mutant *Auxenochlorella protothecoides* of claim 1, a culture thereof, or an oil from the mutant *Auxenochlorella protothecoides*.

5. The composition of claim 4, wherein the composition is a cosmetic composition, a food composition, a composition for a food additive, a feed composition, a composition for a feed additive, a raw material composition for food, a raw material composition for feed, or a raw material composition for cosmetics.

6. The mutant *Auxenochlorella protothecoides* of claim 1, wherein a zeaxanthin has a percent (w/w) of zeaxanthin 2-3-fold higher compared to the wild-type microalgae and the zeaxanthin is present as a major carotenoid.

7. The mutant *Auxenochlorella protothecoides* of claim 6, wherein the percent (w/w) of zeaxanthin produced ranges between 40 to 90% of total identified carotenoids.

8. The mutant *Auxenochlorella protothecoides* of claim 1, wherein the oil contains a mixture of 4-keto lutein and astaxanthin, and wherein the astaxanthin is present as a major carotenoid.

9. The mutant *Auxenochlorella protothecoides* of claim 8, wherein the keto carotenoids produced have a range of between 20-90% (w/w) of total identified carotenoids.

10. The mutant *Auxenochlorella protothecoides* of claim 1, wherein the oil contains squalene.

11. The mutant *Auxenochlorella protothecoides* of claim 1, wherein an omega-6 fatty acids and an omega-3 fatty acids have a weight ratio of omega-6 fatty acids to omega-3 fatty acids in the oil that is low compared to the oil produced from wild type microalgae.

12. The mutant *Auxenochlorella protothecoides* of claim 11, wherein the weight ratio of omega-6 to omega-3 in the oil ranges from 1:1 to 5:1 compared to the oil produced from wild type microalgae which is 7:1.

13. The mutant *Auxenochlorella protothecoides* of claim 1, wherein the omega-3 fatty acids increased 3-5-fold and the overall polyunsaturated fatty acids increased 2-3-fold compared to the wild-type strain.

14. The mutant *Auxenochlorella protothecoides* of claim 1, wherein the microalgal mutant is characterized in that one or more of the alleles of the lycopene cyclase epsilon LCYE-1 gene, lycopene cyclase epsilon LYCE-2 gene are knocked out.

15. The mutant *Auxenochlorella protothecoides* of claim 1, wherein the microalgal mutant is characterized in that one or more of the alleles of the squalene epoxidase SQE-1 gene, or squalene epoxidase SQE-2 gene are knocked out.

16. The mutant *Auxenochlorella protothecoides* of claim 1, wherein the microalgal mutant is characterized in that the native FAD3 promoter is replaced with a stearoyl-ACP desaturase (SAD2) promoter or a promoter from the *Auxenochlorella protothecoides* FATA gene encoding acyl-ACP thioesterase.

\*    \*    \*    \*    \*